(12) United States Patent
Francois et al.

(10) Patent No.: US 8,198,020 B2
(45) Date of Patent: Jun. 12, 2012

US008198020B2

(54) COMPOSITIONS AND METHODS FOR ENHANCING PHAGOCYTOSIS OR PHAGOCYTE ACTIVITY

(75) Inventors: Cedric Francois, Louisville, KY (US); Pascal Deschatelets, Louisville, KY (US); Paul Olson, Louisville, KY (US); Alec Machiels, New York, NY (US)

(73) Assignee: Potentia Pharmaceuticals, Inc., Crestwood, KY (US)

( * ) Notice: Subject to any disclaimer, the term of this patent is extended or adjusted under 35 U.S.C. 154(b) by 520 days.

(21) Appl. No.: 10/923,940

(22) Filed: Aug. 23, 2004

(65) Prior Publication Data

US 2005/0113297 A1 May 26, 2005

Related U.S. Application Data

(60) Provisional application No. 60/497,086, filed on Aug. 22, 2003, provisional application No. 60/514,941, filed on Oct. 28, 2003, provisional application No. 60/523,611, filed on Nov. 19, 2003, provisional application No. 60/524,126, filed on Nov. 21, 2003, provisional application No. 60/524,730, filed on Nov. 24, 2003, provisional application No. 60/547,951, filed on Feb. 26, 2004.

(51) Int. Cl.
| | |
|---|---|
| *C12Q 1/70* | (2006.01) |
| *C12Q 1/00* | (2006.01) |
| *G01N 33/53* | (2006.01) |
| *G01N 33/567* | (2006.01) |
| *G01N 33/574* | (2006.01) |

(52) U.S. Cl. ............... 435/4; 435/5; 435/7.1; 435/7.231; 435/7.23

(58) Field of Classification Search ........................ None
See application file for complete search history.

(56) References Cited

U.S. PATENT DOCUMENTS

| | | | | |
|---|---|---|---|---|
| 5,972,337 | A * | 10/1999 | Ceriani et al. | ............. 424/185.1 |
| 6,217,869 | B1 * | 4/2001 | Meyer et al. | ................ 424/178.1 |
| 6,300,308 | B1 | 10/2001 | Schroit | |
| 7,511,124 | B2 * | 3/2009 | Thorpe et al. | .................. 530/402 |
| 2003/0105000 | A1 * | 6/2003 | Pero et al. | ........................ 514/12 |

FOREIGN PATENT DOCUMENTS

| | | |
|---|---|---|
| WO | WO-2004004667 A2 | 1/2004 |
| WO | WO-2005019429 A2 | 3/2005 |

OTHER PUBLICATIONS

Neth et al., The Journal of Immunology, 2002, 169: 4430-4436.*
Shiratsuchi and Nakanish, 1999, J. Biochem. vol. 126, pp. 1101-1106.*
Schrolt et al (1982) Cancer Research vol. 42, pp. 161-167.*
Raguraman et al. (Biochim. Biophys. Acta 2007,1768:1258-1267).*
Bowie et al. (Science, 1990, 247:1306-1310).*
Skolnick et al. (TIBTECH 18:34-39, 2000).*
Ibragimova and Eade (Biophysical Journal, Oct. 1999, vol. 77, pp. 2191-2198).*
Burgess et al. (J. of Cell Bio. 111:2129-2138, 1990).*
Lazar et al. (Molecular and Cellular Biology, 1988, 8:1247-1252).*
Borisenko et al. (2003) "Macrophage recognition of externalized phosphatidylserine and phagocytosis of apoptotic Jurkat cells—existence of a threshold," Arch. Biochem Biophys., 413(1):41-52.
Chiu et al. (2003) "Targeting of antibody conjugated, phosphatidylserine-containing liposomes to vascular cell adhesion molecule 1 for controlled thrombogenesis," Biochim. Biophys Acta, 1613:115-121.
Fadok et al. (1992) "Exposure of phosphatidylserine on the surface of apoptotic lymphocytes triggers specific recognition and removal by macrophages," J. Immunol., 148:2207-2216.
Fadok et al. (2001) "Loss of phospholipid asymmetry and surface exposure of phosphatidylserine is required for phagocytosis of apoptotic cells by macrophages and fibroblasts," J. Biol. Chem., 276:1071-1077.
Gutheil et al. (2000) "Targeted antiangiogenic therapy for cancer using Vitaxin: a humanized monoclonal antibody to the integrin alphavbeta3," Clin. Cancer Res., 6:3056-3061.
Hanayama et al. (2002) "Identification of a factor that links apoptotic cells to phagocytes," Nature, 417:182-187.
Hoffmann et al. (2001) "Phosphatidylserine (PS) induces PS. receptor-mediated macropinocytosis and promotes clearance of apoptotic cells," J. Cell Biol., 155(4):649-659.
International Search Report for PCT/US04/27245 (Jan. 2006).
Kagan et al. (2002) "A role for oxidative stress in apoptosis: Oxidation and externalization of phosphatidylserine is required for macrophage clearance of cells undergoing Fas-mediated apoptosis," J. Immunol., 169(1):487-499.
Kini et al. (2003) "Phosphatidylserine is required along with oxidized phospholipids on cell surface for synergistic enhancement of phagocytosis by macrophages," Toxicol. Sci., 72(S1):355.
Kumar, C. C. (2003) "Integrin alpha v beta 3 as a therapeu is target for blocking tumor-induced angiogenesis," Curr. Drug Targets, 4:123-131.
Martin et al. (1995) "Early redistribution of plasma membrane phosphtidylserine is a general feature of apoptosis regardless of the initiating stimulus: inhibition by overexpression of Bcl-2 and Abl.," J. Exp. Med., 182:1545-1556.
Moodley et al. (2003) "Macrophage recognition and phagocytosis of apoptotic fibroblasts is critically dependent on fibroblast-derived thrombospondin 1 and CD36," Am. J. Pathol., 162(3):771-9.
Pasqualini et al. (1996) "Organ targeting in vivo using phage display peptide libraries," Nature, 380:364-366.
Pasqualini et al. (2002) "Probing the structural and molecular diversity of tumor vasculature," Trends Mol. Med., 8:563-571.

(Continued)

*Primary Examiner* — Peter J Reddig
(74) *Attorney, Agent, or Firm* — Choate Hall & Stewart, LLP

(57) ABSTRACT

The present invention provides a system for enhancing clearance or destruction of undesirable cells or noncellular molecular entities by tagging such cells or noncellular molecular entities with a marker that targets the cells or noncellular molecular entities for phagocytosis (phagocytic marker). The target cells can be, for example, endothelial cells, tumor cells, leukocytes, or virus-infected cells. In certain embodiments of the invention the tagging is accomplished by administering a composition comprising an antibody or ligand linked to the phagcytotic marker, wherein the antibody or ligand binds to a cell type specific marker present on or in the cell surface of a target cell. In preferred embodiments of the invention, the phagocytic marker comprises phosphatidylserine or a group derived from phosphatidylserine, thrombospondin-1, annexin I, or a derivative of any of these.

59 Claims, 23 Drawing Sheets

OTHER PUBLICATIONS

Pradhan et al. (1997) Multiple systems for recognition of apoptotic lymphocytes by macrophages, Mol. Biol. Cell, 8(5):767-78.

Ran et al. (2002) "Phosphatidylserine is a marker of tumor vasculature and a potential target for cancer imaging and therapy," International Journal of Radiation Oncology Biology Physics, 54(5)1479-1484.

Schroit et al. (1985) "In vivo recognition and clearance of red blood cells containing phosphatidylserine in their plasma membranes," J. Biol. Chem. 260(8):5131-8.

Schroit et al. (1983) "Synthesis and properties of radioiodinated phospholipids analogues that spontaneously undergo vesicle-vesicle and vesicle-cell transfer," Biochemistry, 22:3617-3623

St. Croix, B. (2000) "Genes expressed in human tumor endothelium," Science, 289(5482):1197-202.

Tanaka et al. (1983) "Insertion of fluorescent phosphatidylserine into the plasma membrane of red blood cells. Recognition by autologous macrophages," J. Biol. Chem., 258(18):11335-43.

Written Opinion for PCT/US04/27245 (Jan. 2006).

Wu et al. (2004) "A novel small peptide as a targeting ligand for receptor tyrosine kinase Tie2," Biochem. Biophys. Res. Commun., 315(4):1004-10.

* cited by examiner

Phosphatidyl serine

= Ligand or Antibody

= Ligand or Antibody antibody or ligand

PSG = group derived from phosphatidylserine

PSG = group derived from phosphatidylserine

Reacting proteins with imidothiolane to generate free thiols.

Coupling of a thiol-reactive PS derivative with a protein containing free thiols.

COMPOSITIONS AND METHODS FOR ENHANCING PHAGOCYTOSIS OR PHAGOCYTE ACTIVITY

CROSS-REFERENCE TO RELATED APPLICATIONS

This application claims priority to provisional application 60/497,086, filed Aug. 22, 2003; 60/514,941, filed Oct. 28, 2003; 60/523,611, filed Nov. 19, 2003; 60/524,126, filed Nov. 21, 2003; 60/524,730, filed Nov. 24, 2003, and 60/547,951, filed Feb. 26, 2004, all of which are herein incorporated by reference.

Sequence Listing

In accordance with 37 CFR § 1.52(e)(5), the present specification makes reference to a Sequence Listing (submitted electronically as a .txt file named "SeqListing3.txt" on Dec. 29, 2011). The .txt file was generated on Dec. 29, 2011 and is 7 kb in size. The entire contents of the Sequence Listing are herein incorporated by reference.

BACKGROUND OF THE INVENTION

The body has a number of mechanisms by which to rid itself of undesirable cells, and many diseases result from defects or deficiencies in these processes. For example, although the immune system is believed to play an important role in preventing the development of tumors or curtailing their growth or spread, it is clear that in many cases immune surveillance is not sufficient to prevent cancer. Particular populations of cells can also cause or contribute to a variety of other diseases. For example, white blood cells of various types may cause rejection of a transplanted organ, auto-immune disease, or allergies. Proliferation of vascular tissue in the eye can lead to vision loss. Molecules and other entities that are not properly removed or disposed of can also cause disease. Examples of such entities are calcium, fatty acids, lipids, uric acid, bilirubin, etc. Thus it is evident that the body's own mechanisms for detecting and removing cells and harmful noncellular molecular entities are frequently insufficient. There is a need for improved methods to remove such undesirable cells or noncellular molecular entities.

Despite significant advances, cancer continues to be an extremely difficult disease to treat, claiming ~550,000 lives annually in the United States alone (49). In addition, many currently available pharmaceutical agents target dividing cells generally rather than being selective for cancer cells. This feature is responsible for numerous side effects that frequently limit the acceptable dose that can be delivered to a patient. New therapeutic strategies are urgently needed. In particular, there is a need for therapeutic strategies that would more specifically target cancerous cells. In addition, there is a need for strategies that would synergize with or enhance existing methods of treating cancer.

SUMMARY OF THE INVENTION

The present invention addresses the foregoing needs, among others. The invention provides a system for tagging cells or noncellular molecular entities that may occur in or on biological systems such as living cells, tissues, organs, organisms, body fluids, etc., with molecules that increase the likelihood that a target cell or noncellular molecular entity will be phagocytosed, e.g., that make the tagged cells or noncellular molecular entities better targets for phagocytosis. In particular, the present invention provides the recognition that cells can be tagged or coated with molecules that incite phagocytes to phagocytose them, similarly to the manner in which display of certain markers on apoptotic cells contributes to, enhances, or incites phagocytosis. According to certain embodiments of the present invention, the level and/or density of a phagocytic marker, such as phosphatidylserine or a group derived from phosphatidylserine, is increased on or at cell surfaces or on or at the surface of noncellular molecular entities. A variety of phagocytic markers can be used, including both markers found on apoptotic cells and markers found in various other contexts such as on the surface of bacteria.

Phosphatidylserine is an anionic phospholipid that provides a signal for macrophages and possibly other phagocytic cells to initiate phagocytosis. Thrombospondin, e.g., thrombospondin-1, is another molecule that provides a signal for macrophages and possibly other phagocytic cells to initiate phagocytosis. Thus, according to the present invention, increasing the level and/or density of phosphatidylserine or thrombospondin or a group derived therefrom on or at the cell surface will increase the likelihood that it will be a target for phagocytosis. Similarly, increasing the level or density of a phagocytic marker on or at the surface of a molecular entity will make phagocytes more likely to attack and engulf the entity than would otherwise be the case. Thus in one aspect the invention provides a method of making a target cell or molecular entity prone to, i.e., more susceptible to, phagocytosis comprising increasing the level or density of a phagocytic marker on or at the surface of the target cell or molecular entity. In another aspect the invention provides a method of making a target cell or molecular entity prone to, i.e., more susceptible to, immune destruction comprising increasing the level or density of a phagocytic marker on or at the surface of the target cell or molecular entity.

In preferred embodiments of the present invention, the level and/or density of phosphatidylserine or thrombospondin, or a phagocytosis-enhancing portion of either, on the cell surface may be increased by attaching the phosphatidylserine, thrombospondin, or a derivative of either to the membrane of the cells by means of an antibody or ligand, for example an antibody or ligand that interacts with a specific target (e.g., a cellular marker such as a cell type specific marker) on the cell membrane. Such specific targets may include any transmembrane or membrane protein, any protein with an extracellular domain, lipid, carbohydrate or proteoglycan elements on the cell surface, etc. Alternatively or additionally, the level and/or density of phosphatidylserine or thrombospondin or a phagocytosis-enhancing portion of either is increased by inserting phosphatidylserine or a derivative (e.g., anionic phospholipids) or thrombospondin or a derivative thereof such as a fragment into the membrane of cells, e.g., endothelial cells, tumor cells, leukocytes, or virus-infected cells, for example through the use of fusogenic vesicles.

Unless otherwise stated, the invention makes use of standard methods of molecular biology, cell culture, animal maintenance, etc., and uses art-accepted meanings of terms. This application refers to various patents and publications. The contents of all of these are incorporated by reference. In addition, the following publications are incorporated herein by reference: *Current Protocols in Molecular Biology, Current Protocols in Immunology, Current Protocols in Protein Science, and Current Protocols in Cell Biology*, all John Wiley & Sons, N.Y., edition as of July 2002; Sambrook, Russell, and Sambrook, *Molecular Cloning: A Laboratory Manual*, 3$^{rd}$ ed., Cold Spring Harbor Laboratory Press, Cold Spring Harbor, 2001; *Kuby Immunology*, 4$^{th}$ ed., Goldsby, R.

A., Kindt, T. J., and Osborne, B. (eds.), W. H. Freeman, 2000, *Goodman and Gilman's The Pharmacological Basis of Therapeutics*, 10th Ed. McGraw Hill, 2001, and Katzung, B. (ed.) *Basic and Clinical Pharmacology*, McGraw-Hill/Appleton & Lange; 8th edition (Sep. 21, 2000), Devita, V. T., Hellman, S., and Rosenberg, S. A., *Cancer: Principles and Practice of Oncology*, 6th ed., Lippincott Williams & Wilkins (Jul. 1, 2001). In the event of a conflict between any of the incorporated references and the instant specification, the specification shall control.

The term "comprising" is used herein in a general sense. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. Where ranges are given, endpoints are included. Where figures either in the Drawing or in the specification or claims depict molecules comprising a phosphatidylserine derivative, it is to be understood that the protonation state of various atoms (e.g., the N and O in the amino and carboxylic acid portions, respectively of the serine moiety, the O atoms attached to a P in a PS head group) may differ depending on the pH, as will be understood by one of ordinary skill in the art. All ionized and nonionized forms are included in various embodiments of the invention, and the depiction of a molecule with particular atoms in a charged or uncharged, protonated or unprotonated state is not intended to indicate that the molecules are necessarily in such a state. Furthermore, salts of the compounds are included, as further discussed below.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, the replacement of a carbon by a $^{13}$C- or $^{14}$C-enriched carbon, the replacement of nitrogen, phosphorus, or sulfur with an isotope thereof, etc., are within the scope of this invention. Such compounds are useful, for example, as analytical tools or probes in biological assays.

DEFINITIONS

Figure 1A:
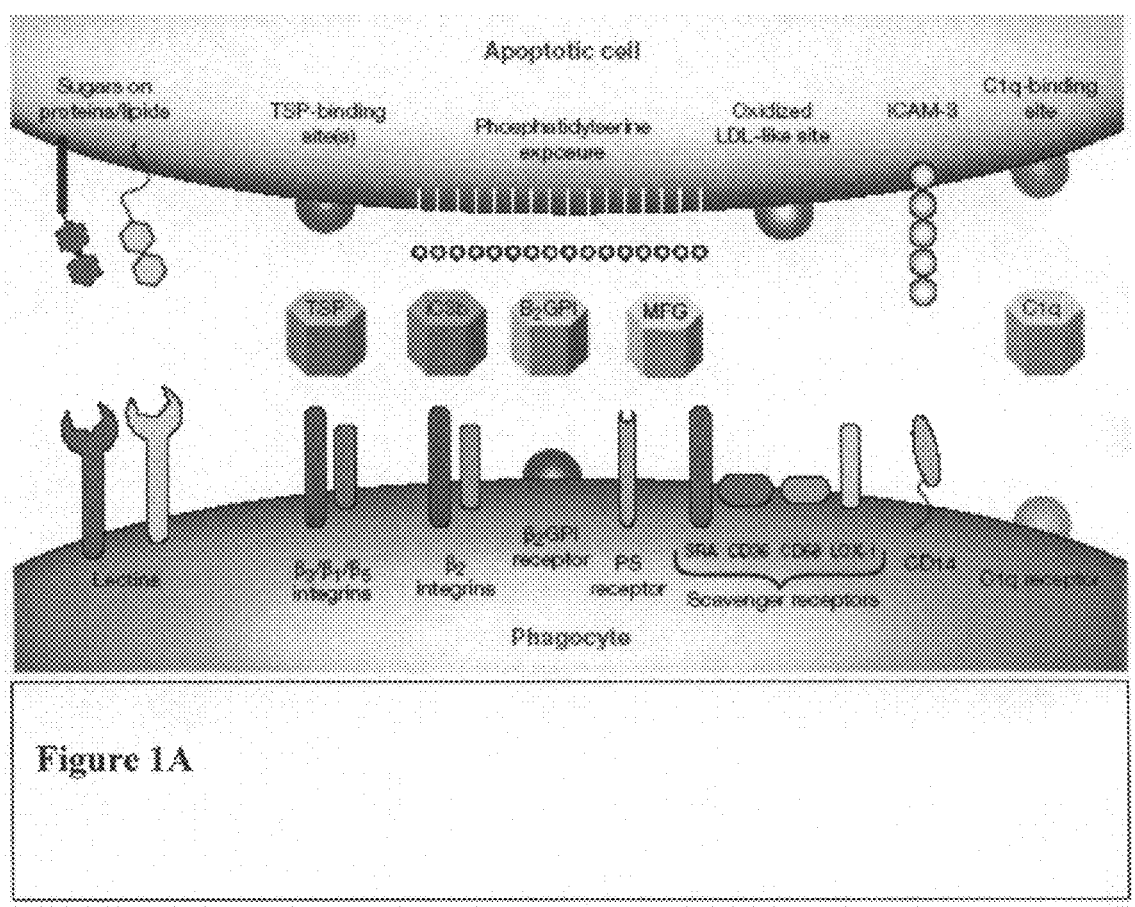
FIG. 1A shows a schematic representation of molecules and mechanisms involved in phagocyte recognition of apoptotic cells.

Angiogenesis is the promotion or development of new capillary blood vessels resulting in an increased vascularization, often associated with a particular organ or tissue, or with a tumor.

$\beta_2$-glycoprotein, also known as apolipoprotein H (apoh) (GenBank entry for the complete human beta-2-glycoprotein is NP_000033), is considered to be an essential cofactor for the binding of certain antiphospholipid autoantibodies to anionic phospholipids. This binding usually triggers the production of a subset of autoantibodies against phospholipids present in patients with autoimmune diseases (149). It is also believed to be a normal bridging molecule between phosphatidylserine and the macrophage scavenger receptor.

Concurrent administration of two or more agents, e.g., therapeutic agents, is administration performed using doses and time intervals such that the administered agents are present together within the body over a time interval in less than de minimis quantities. The time interval can be minutes, hours, days, weeks, etc. Accordingly, the agents may, but need not be, administered together as part of a single composition. In addition, the agents may, but need not be, administered simultaneously (e.g., within less than 5 minutes, or within less than one minute) or within a short time of one another (e.g., less than an hour, less than 30 minutes, less than 10 minutes, approximately 5 minutes apart). According to various embodiments of the invention agents administered within such time intervals may be considered to be administered at substantially the same time. One of ordinary skill in the art will be able to readily determine appropriate doses and time interval between administration of the agents so that they will each be present at more than de minimis levels within the body or, preferably, at effective concentrations within the body. When administered concurrently, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

Effective amount of an active agent refers to the amount sufficient to elicit a desired biological response. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. For example, in the case of anti-neoplastic agents, the effective amount may be the amount of agent needed to reduce the size of a primary tumor, to reduce the size of a secondary tumor, to reduce the number of metastases, to reduce the growth rate of a tumor or the cell division rate, to increase the time before relapse, to reduce the ability of a primary tumor to metastasize, to increase life expectancy, to reduce the number of circulating cancer cells (e.g., in the case of cancers of the hematopoietic system) to reduce one or more tumor-related symptoms, etc.

Endothelial cell is to be given its meaning as generally accepted in the art, i.e., the layer of squamous epithelium that lines the cavities of the heart, blood vessels (including capillaries), and lymph vessels. The terms "endothelium" and "vascular endothelium" are used interchangeably herein. Endothelial cell precursors are cells that have the potential to develop into endothelial cells and display at least one marker characteristic of endothelial cells but do not possess the full range of functional properties possessed by mature endothelial cells. Endothelial cells typically display a characteristic set of markers including, for example, von Willebrand factor. In addition to pan-endothelial markers, endothelial cells in different vascular beds or organs may display markers that are specific to endothelial cells in that type of vascular bed or organ.

Fusogenic vesicles are liposomes whose outer wall contains molecules (such as but not restricted to the F protein) that promotes their fusion with cellular membranes.

Group derived from phosphatidylserine or phosphatidylserine head group derivative refers to a molecule that constitutes a portion of a complete PS molecule, including at least a PS head group as described below, with the proviso that in certain embodiments of the invention one or more of the O atoms attached to P, preferably one of the non-bridging O atoms, may be replaced with S. Thus in certain preferred embodiments of the invention the term refers to moieties that comprise the structure shown in FIG. 1E, wherein Y=O. In other embodiments the term refers to moieties that comprise the structure shown in FIG. 1E, wherein at least one Y=S (i.e., 1, 2, 3, or 4). Where one or more Y=S, preferably Y is a non-bridging (i.e., connected only to P) Y atom. The group need not have been obtained from naturally occurring phosphatidylserine but instead may be obtained through any available means including chemical synthesis.

Isolated, as used herein, means 1) separated from at least some of the components with which it is usually associated in nature; 2) prepared or purified by a process that involves the hand of man; and/or 3) not occurring in nature.

Linked, as used herein with respect to two or more moieties, means that the moieties are physically associated or connected with one another to form a molecular structure that is sufficiently stable so that the moieties remain associated under the conditions in which the linkage is formed and, preferably, under the conditions in which the new molecular structure is used, e.g., physiological conditions. In certain preferred embodiments of the invention the linkage is a covalent linkage. In other embodiments the linkage is noncovalent. Moieties may be linked either directly or indirectly. When two moieties are directly linked, they are either covalently bonded to one another or are in sufficiently close proximity such that intermolecular forces between the two moieties maintain their association. When two moieties are indirectly linked, they are each linked either covalently or noncovalently to a third moiety, which maintains the association between the two moieties. In general, when two moieties are referred to as being linked by a "linker" or "linking moiety" or "linking portion", the linkage between the two linked moieties is indirect, and typically each of the linked moieties is covalently bonded to the linker. The linker can be any suitable moiety that reacts with the two moieties to be linked within a reasonable period of time, under conditions consistent with stability of the moieties (which may be protected as appropriate, depending upon the conditions), and in sufficient amount, to produce a reasonable yield.

Liposomes are artificial microscopic spherical particles in an aqueous medium, formed by a lipid bilayer (or multilayers) enclosing an aqueous compartment. Liposomes are commonly used in molecular biology as a delivery vector for various types of molecules (such as proteins, small molecules, DNA, and RNA), including a number of different drugs. They are also used to study cell membranes and membrane proteins.

Markers for the purpose of the description of the invention may be any molecular moiety (e.g., protein, peptide, mRNA or other RNA species, DNA, lipid, carbohydrate) that characterizes, indicates, or identifies a particular diseased or physiological state (e.g., apoptotic, cancerous, normal) or characterizes, indicates, or identifies one or more cell type(s), tissue type(s), or embryological origin. The presence or absence of certain marker(s), or the amount of certain marker(s), may indicate a particular physiological or diseased state of a patient, organ, tissue, or cell. A cellular marker may, but need not be, cell type specific. For example, a cell type specific marker is generally a protein, peptide, mRNA, lipid, or carbohydrate that is present at a higher level on or in a particular cell type or cell types of interest than on or in many other cell types. In some instances a cell type specific marker is present at detectable levels only on or in a particular cell type of interest. However, it will be appreciated that useful markers need not be absolutely specific for the cell type of interest. For example, certain CD molecules are present on the cells of multiple different types of leukocytes. In general, a cell type specific marker for a particular cell type is expressed at levels at least 3 fold greater in that cell type than in a reference population of cells which may consist, for example, of a mixture containing cells from a plurality (e.g., 5-10 or more) of different tissues or organs in approximately equal amounts. More preferably the cell type specific marker is present at levels at least 4-5 fold, between 5-10 fold, or more than 10-fold greater than its average expression in a reference population. Preferably detection or measurement of a cell type specific marker makes it possible to distinguish the cell type or types of interest from cells of many, most, or all other types. In general, the presence and/or abundance of most markers may be determined using standard techniques such as Northern blotting, in situ hybridization, RT-PCR, sequencing, immunological methods such as immunoblotting, immunodetection, or fluorescence detection following staining with fluorescently labeled antibodies, oligonucleotide or cDNA microarray or membrane array, protein microarray analysis, mass spectrometry, etc.

MFG-E8 (milk fat globule-EGF factor 8) (GenBank accession number is AAH03610 for the complete protein) is a factor that serves to bridge apoptotic cells and phagocytes. Milk fat globule-EGF-factor 8 (MFG-E8) is a secreted glycoprotein, which is normally produced by macrophages, particularly under conditions of stimulation (e.g., thioglycolate-elicited macrophages), and under certain conditions by various other cell types. It binds specifically to apoptotic cells by recognizing aminophospholipids such as phosphatidylserine. MFG-E8, when engaged by phospholipids, binds to cells via its RGD (arginine-glycine-aspartate) motif and binds particularly strongly to cells expressing alpha(v)beta(3) integrin (68). Cells expressing high levels of alpha(v)beta(3) integrin can engulf apoptotic cells when MFG-E8 is added.

Phagocytosis is the process by which particulate material (such as microorganisms, cells, cellular debris, tissue deposits, small foreign objects, etc.) is ingested by cells. All cells are phagocytic to a certain degree. However, neutrophils and monocytes/macrophages are quantitatively much more able to ingest particulates. Therefore, they are sometimes referred to as "professional" phagocytes. The process consists of recognition of the particle, ingestion of the particle by flowing over and engulfing it whole, and digestion of the particle. Phagocytic vacuoles (phagosomes) are formed by invagination of the plasma membrane. Phagosomes fuse with lysosomes, to produce phagolysosomes in which the killing (if applicable) and digestion of particulate material are accomplished.

Phagocytic markers for the purpose of the description of the invention are any molecular moieties that, when present on or at the surface of a cell or, in certain embodiments of the invention when present on or at the surface of a noncellular molecular entity, can enhance phagocytosis, e.g., can increase the likelihood that the cell or noncellular molecular entity will be a target for phagocytosis by phagocytic cells (such as macrophages) and preferably will be phagocytosed by such cells. These phagocytic markers can be, but are not restricted to phosphatidylserine, a group derived from phosphatidylserine, thrombospondin, MFG-E8, $\beta_2$-glycoprotein, protein S, annexin I, GAS-6, and portions or derivatives of any of the foregoing. In certain embodiments of the invention a phagocytic marker is, or comprises or consists of, a portion of a naturally occurring molecule. By "can enhance phagocytosis" is meant that under appropriate conditions, e.g., typical physiological conditions such as exist in cell culture and/or within the body of a subject, the presence of the phagocytic marker does enhance phagocytosis. Similarly, by "can increase the likelihood that the cell or noncellular molecular entity will be a target for phagocytosis" is meant that under appropriate conditions, e.g., typical physiological conditions such as exist in cell culture and/or within the body of a subject, the presence of the phagocytic marker does increase the likelihood that the cell or noncellular molecular entity will be a target for phagocytosis.

Figure 1B:
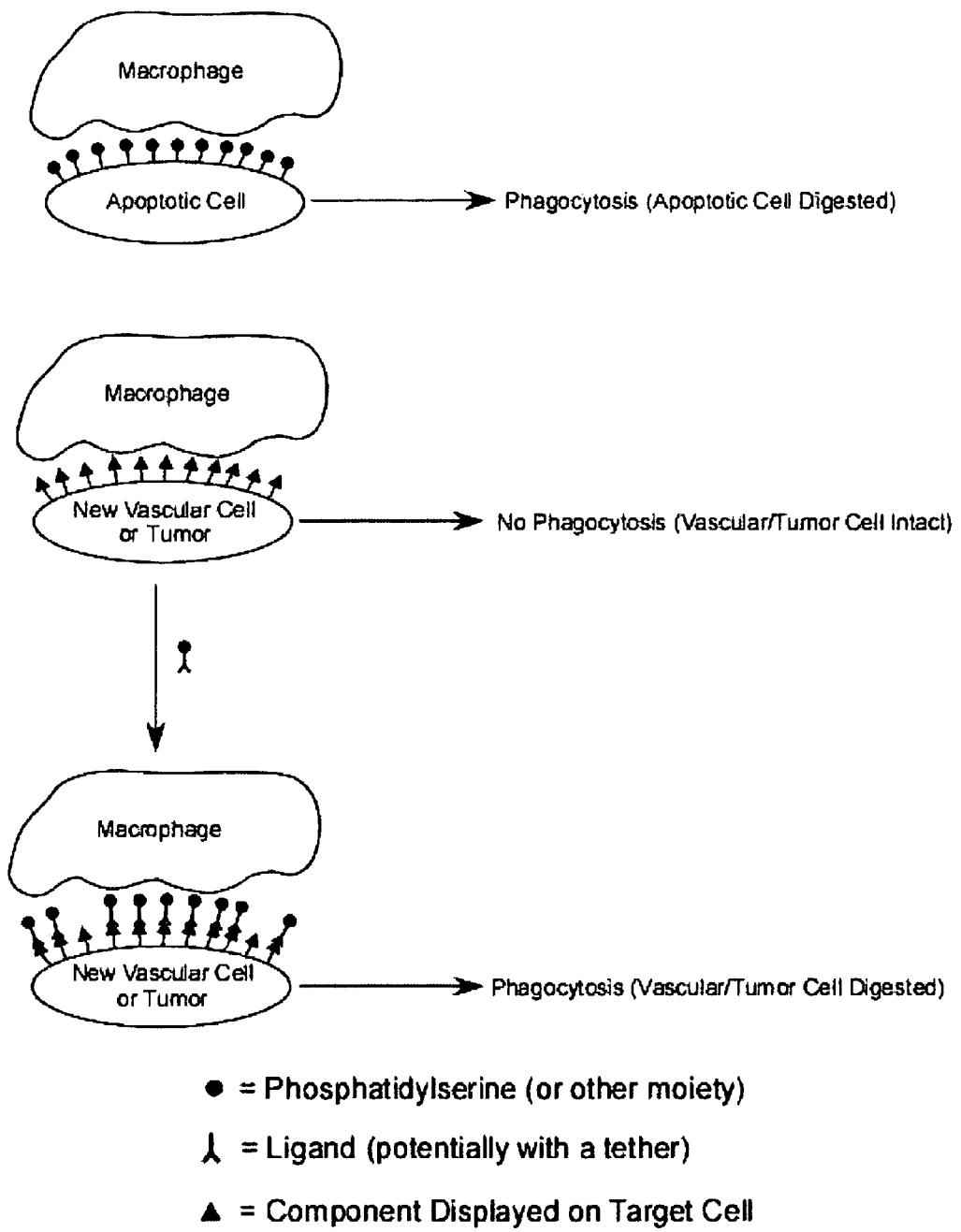
FIG. 1B shows a schematic representation of one embodiment of an inventive system for tagging cells to make them appear apoptotic. As depicted, the level or density of a phagocytic marker (in this case phosphatidylserine) is increased on the cell surface, so that the cells are targeted for phagocytosis by macrophages.
Figure 1C:
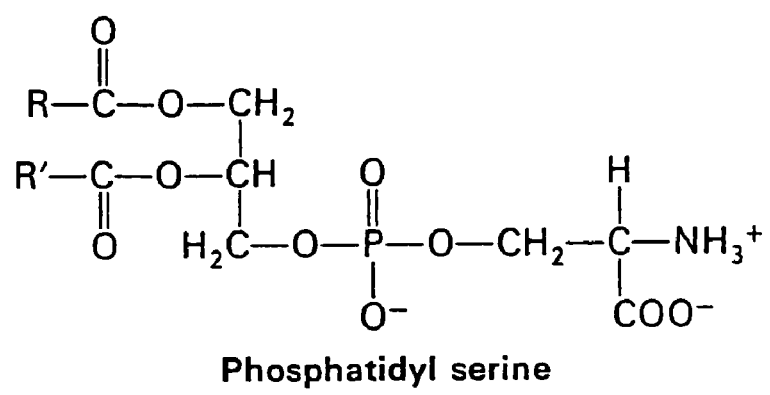
FIG. 1C shows the structure of naturally occurring phosphatidylserine.
Figure 1D:
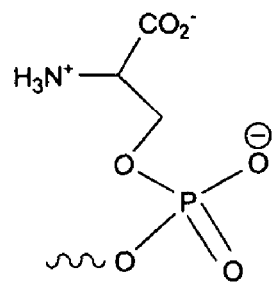
FIG. 1D shows the structure of a PS head group. The wavy line indicates a position where a bond may be formed to another atom.

Phosphatidylserine head group, for purposes of the present invention, refers to the portion of a phosphatidylserine molecule shown in FIG. 1D, i.e., the serine-derived group, the phosphorus atom, and the oxygen atoms attached to the phosphorus atom.

Polypeptide, as used herein, is a chain of amino acids. A protein is a molecule composed of one or more polypeptides. A peptide is a relatively short polypeptide, typically between about 2 and 60 amino acids in length.

Purified, as used herein, means separated from many other compounds or entities. A compound or entity may be partially purified, substantially purified, or pure, where it is pure when it is removed from substantially all other compounds or entities, i.e., is preferably at least about 90%, more preferably at least about 91%, 92%, 93%, 94%, 95%, 96%, 97%, 98%, 99%, or greater than 99% pure.

Sequential administration of two or more agents refers to administration of two or more agents to a subject such that the agents are not present together in the subject's body at greater than de minimis concentrations. Administration of the agents may, but need not, alternate. Each agent may be administered multiple times.

Small molecule: As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

Specific binding generally refers to a physical association between a target polypeptide (or, more generally, a target molecule) and a binding molecule such as an antibody or ligand. The association is typically dependent upon the presence of a particular structural feature of the target such as an antigenic determinant or epitope recognized by the binding molecule. For example, if an antibody is specific for epitope A, the presence of a polypeptide containing epitope A or the presence of free unlabeled A in a reaction containing both free labeled A and the binding molecule that binds thereto, will reduce the amount of labeled A that binds to the binding molecule. It is to be understood that specificity need not be absolute but generally refers to the context in which the binding occurs. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies or ligands having a sufficient degree of specificity to perform appropriately in any given application (e.g., for detection of a target molecule, for therapeutic purposes, etc). It is also to be understood that specificity may be evaluated in the context of additional factors such as the affinity of the binding molecule for the target versus the affinity of the binding molecule for other targets, e.g., competitors. If a binding molecule exhibits a high affinity for a target molecule that it is desired to detect and low affinity for nontarget molecules, the antibody will likely be an acceptable reagent. Once the specificity of a binding molecule is established in one or more contexts, it may be employed in other, preferably similar, contexts without necessarily re-evaluating its specificity.

Subject, as used herein, refers to an individual to whom an agent is to be delivered, e.g., for experimental, diagnostic, and/or therapeutic purposes. Preferred subjects are mammals, particularly domesticated mammals (e.g., dogs, cats, etc.), primates, or humans.

Treating, as used herein, can generally include reversing, alleviating, inhibiting the progress of, preventing, or reducing the likelihood of the disease, disorder, or condition to which such term applies, or one or more symptoms or manifestations of such disease, disorder or condition.

Tumor, as used herein, refers to an abnormal mass of tissue or collection of cells that results from excessive and abnormal cell division. They may be either benign (not cancerous) or malignant (cancerous). As used herein, the term includes malignancies of the hematopoietic system even if they do not result in a discrete mass.

DETAILED DESCRIPTION OF CERTAIN PREFERRED EMBODIMENTS OF THE INVENTION

The present invention provides methods and reagents for tagging cells or noncellular molecular entities with moities that enhance their phagocytosis. The compositions of the invention increase the likelihood that a target cell will be phagocytosed, i.e., make the target cell prone to phagocytosis, facilitate efficient phagocytosis, etc. Such compositions will be said to enhance phagocytosis. In certain embodiments of the invention the molecules make the cells appear apoptotic. In general, cells of any type (e.g., prokaryotic or eukaryotic) can be tagged. Noncellular molecular entities include calcium, fatty acids, lipids, uric acid, bilirubin, viruses or portions of viruses, and other pathogenic microorganisms such as bacteria or parasites. For purposes of the present invention, atoms or ions (such as Ca or $Ca^{++}$) are considered molecules.

Some particularly useful applications of the inventive tools are in the treatment of cancer, macular degeneration, diabetic retinopathy, allergies, autoimmune diseases and rejection of transplanted organs. Tumor growth can be inhibited by inhibiting the new growth of vessels through tagging the endothelial cells in these vessels with phagocytic markers. Tissues that are in need of oxygen or other nutrients secrete a variety of factors (e.g., vascular endothelial growth factor (VEGF), hypoxia-inducible factor (HIF), etc.) that promote the growth of blood vessels to support the needy tissue by increasing blood flow toward them. The present invention provides tools for inhibiting this process.

One particularly useful application of the inventive tools is in the treatment of cancer, as new growth of vessels is particularly important for tumors. However, many other diseases result at least in part from and/or are characterized by excessive or abnormal angiogenesis (64). Examples of such angiogenesis-associated diseases are psoriasis, arthritis, osteomyelitis, synovitis, osteophyte formation, obesity, warts, allergic dermatitis, asthma, polyps, atherosclerosis, hemangiomas, vascular malformations, DiGeorge syndrome, hereditary hemorrhagic telangiectasia, transplant arteriopathy, warts, scar keloids, pyogenic granulomas, blistering disease, Kaposi's sarcoma (e.g., in AIDS patients), primary pulmonary hypertension, inflammatory bowel disease, periodontal disease, ascites, peritoneal adhesions, endometriosis, uterine bleeding, ovarian cysts and hyperstimulation, various additional autoimmune diseases, etc. For further discussion and references see *Nature Medicine*; Vol 9(6) page 654 (June 2003). Tumors can also be targeted directly and tagged individually with phagocytic markers. Many forms of macular degeneration, as well as diabetic retinopathy, retinopathy of prematurity, persistent hyperplastic vitreous syndrome, and choroidal neovascularization are also at least in part the result of unwanted vessel growth. By tagging newly formed endothelial cells with phagocytic markers, this process can also be inhibited.

Other cells that can be tagged with phagocytic markers include leukocytes such as T cells, B cells, monocytes, granulocytes, neutrophils, and megakaryocytes. Such cells are frequently involved in autoimmune diseases (e.g., rheumatoid arthritis, lupus, psoriasis, Sjogren's syndrome, scleroderma, arteritis, vasculitis, Graves disease, multiple sclerosis, dermatomyositis, ankylosing spondylitis, polymyalgia rheumatica, etc.). Various autoimmune diseases that may be treated using the methods and compositions disclosed herein are described in *Textbook of the Autoimmune Diseases*, Lahita, R. G., Chiorazzi, N., Reeves, W. (eds.), Lippincott, Williams, and Wilkins, $1^{st}$ Ed. (May 15, 2000). In addition, the recognition of non-self antigens present on transplanted organs by leukocytes can result in an immune response directed against the organ, which can result in either acute or chronic rejection of the organ. (See, e.g., *Transplantation*, Ginns, L. C., Morris, P. J., Cosimi, A. B. (eds.), Blackwell Publishers, 1998, for further details of this phenomenon. By tagging leukocytes with phagocytic markers, the number of such cells will be reduced, thereby reducing the undesirable immune system response that contributes to autoimmune disease or organ rejection. Cellular markers also include major histocompatibility class I (MHC I) and class II (MHC II) molecules. In general, MHC II molecules are found on various immune system cells. In the case of MHC I molecules, which are found on most or all cell types, the MHC I molecule may serve as a target in conjunction with another molecule, e.g., a peptide displayed in association with the MHC I molecule. Erythrocytes can also be tagged, which can be useful for treating diseases such as polycythemia or various tumors in which excessive production of red cells occurs.

Additional cell types that can be tagged with phagocytic markers include, but are not limited to, osteoclasts, endothelial precursor cells, hematopoietic precursor cells, fibroblasts, and platelets (which are fragments of megakaryocytes and are considered cells for the purposes of the present invention). Diseases or conditions associated that may be treated or prevented by enhancing clearance of certain cell types include osteoporosis or osteopenia (for both of which osteoclasts are tagged), fibrosis, scar formation, or peritoneal adhesions (for each of which fibroblasts and/or smooth muscle cells are tagged), and vascular stenosis of native vessels or stenosis or restenosis of natural or synthetic vascular grafts (for all of which fibroblasts, smooth muscle cells, and/or endothelial cells are tagged). In addition, excessive platelet counts (e.g., in cancer patients or in any prothrombotic state, by which is meant any state associated with an increased risk of thrombosis) may be treated or prevented by tagging platelets. Appropriate cellular markers, e.g., cell type specific markers for these cell types are known in the art. For example, platelet fibronectin receptor, alpha and beta subunits, also called platelet glycoprotein IIb/IIIa can be used as markers for platelets. The alpha subunit (GPIIb) has GenBank accession number NP_000410. The beta subunit (GPIIIa) has GenBank accession number NP_000203. Antibodies that can be used to target GPIIb/IIIa include, abciximab, a mouse-human chimeric monoclonal antibody Fab fragment (150). Additional markers for platelets include platelet glycoprotein VI (GenBank: NP_057447) and platelet glycoprotein IX (GenBank: NP_000165).

Adipocytes may also be tagged with a phagocytic marker in accordance with the invention. Enhancing removal of adipocytes by tagging them with phagocytic markers is useful for the treatment or prevention of obesity and other conditions associated with undesired accumulations of fat. Obesity predisposes to, contributes to, or causes a large number of diseases and pathological conditions including, but not limited to, diabetes and its complications, cardiovascular disease, hypertension, atherosclerosis, stroke, the metabolic syndrome, polycystic ovary disease, and sleep apnea (128). In addition, obesity has been associated with various cancers such as breast cancer, colon cancer, etc.(129). The compositions of the invention, in which a phagocytic marker is targeted to adipocytes, are useful to prevent or treat these diseases and conditions that are associated with obesity.

In additional embodiments of the invention tumor cells are tagged with phagocytic markers. In yet other embodiments of the invention cells infected with a pathogen such as a virus, intracellular bacterium, or parasite, are tagged, e.g., cells that express a molecule indicative of infection such as a viral, bacterial, or parasite polypeptide, or a host protein that is induced following infection by the pathogen, on or at their surface.

In other embodiments of the invention, noncellular molecular entities are tagged with phagocytic markers, making them a target for phagocytosis. Examples of such entities include, but are not limited to fatty acids, uric acid, lipids, prions, calcium, bilirubin, viruses or viral particles, etc.

In accordance with the invention cells, e.g., endothelial cells, leukocytes, tumor cells, pathogen-infected cells, or noncellular molecular entities, are labeled, or tagged, with a molecule that attracts phagocytotic cells and/or contributes to or enhances the engulfment of cells by phagocytes. Such molecules are referred to herein as phagocytic markers, as defined above. In certain preferred embodiments of the invention, the phagocytic marker is a molecule, complex, or moiety that is associated with apoptosis, e.g., a molecule, complex, or moiety that is selectively expressed or exposed by cells that are undergoing apoptosis or are in a pre-apoptotic state. For example, the marker may be a molecule, complex, or moiety that is typically present at higher levels in or on cells that are destined to undergo apoptosis or are actually undergoing apoptosis than in or on comparable non-apoptotic cells. As is known in the art, apoptosis is a physiological process for killing cells that is critical for the normal development and function of multicellular organisms. Apoptosis involves cell destruction that is accomplished by proteolysis of cellular constituents, DNA degradation, and phagocytosis. (For more information on apoptosis see Strasser, A, et al., *Annual Review of Biochemistry*, 69, pp. 217-245.) Phagocytic markers may also enhance killing of destruction of target cells by phagocytes through mechanisms other than phagocytosis, e.g., via induction of apoptosis (which may then be followed by apoptosis).

FIG. 1A shows a schematic representation of molecules and mechanisms that are believed to be involved in phagocytosis of apoptotic cells. A repertoire of cell surface molecules displayed by apoptotic cells (top) interact with receptors on the phagocyte (bottom), either directly or via serum-derived bridging molecules (middle), serving as signals that trigger or enhance recognition and/or engulfment of the apoptotic cell. A number of these markers and bridging molecules are discussed further below.

A method of the invention, and its relationship to normally occurring phagocytosis, is depicted in FIG. 1B. As mentioned above and shown in the upper panel of the figure, cells that have entered the apoptotic pathway frequently express molecules on their cell surface (indicated as circles in the figure) that are not found on the surface of non-apoptotic cells, or are present at much lower levels on non-apoptotic cells. These markers are recognized by phagocytic cells such as macrophages, leading to their engulfment and ultimately digestion. As shown in the middle panel of the figure, cells such as vascular cells (e.g., endothelial cells), tumor cells, pathogen-infected cells, etc., express cellular markers on their cell surface (indicated as triangles in the figure). In general, such cellular markers are typically not recognized by phagocytic cells if they are molecules normally found in the body, such as growth factor receptors, etc. (It will be appreciated that foreign antigens or tumor antigens may be recognized by phagocytic cells, but the extent of expression or the degree of recognition may not be optimal to trigger phagocytosis.) In addition, cancer can inhibit the complement cascade, which may normally play a role in phagocytosis. This feature and others may reduce the efficiency at which phagocytes recognize and phagocytose cancer cells.

Figure 2A:
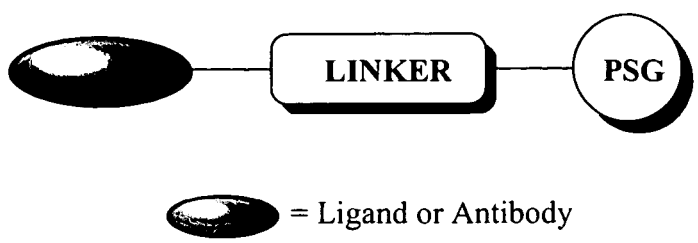
FIG. 2A shows the structure of various compounds of the invention.
Figure 2C:
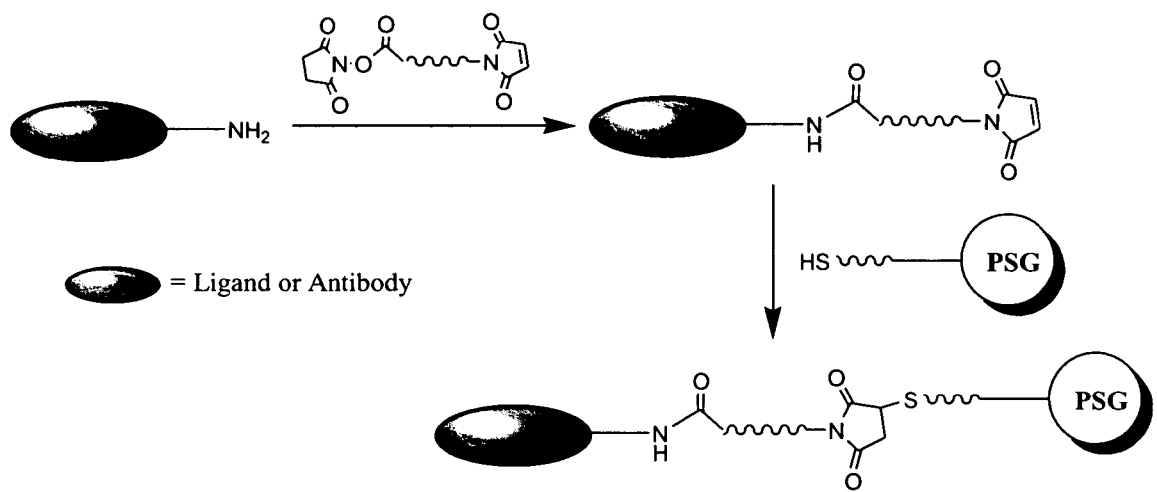
FIG. 2C shows another linkage strategy to form a conjugates in which a protein such as an antibody or a ligand that binds to a molecular target, e.g., a cellular marker on or at the surface of a target cell, is covalently linked to PS or to a group derived from PS.

According to certain embodiments of the invention a bifunctional molecule is provided. The bifunctional molecule includes a portion (indicated in the figure) that binds to a cellular marker present on a target cell such as an endothelial cell or tumor cell. The cell binding portion is typically an antibody or ligand that binds to the cellular marker. The cellular marker is typically, but need not be, a cell type specific marker. The bifunctional molecule also comprises a phagocytic marker (indicated by circles). Binding of the bifunctional molecule to the cell, as shown in the lower panel of the figure, increases the level and/or density of the phagocytic marker on the surface of the cell, leading to its recognition and engulfment by the macrophage. FIG. 2A shows an exemplary molecule of the invention in which the phagocytic marker is a group derived from phosphatidylserine (PSG).

The present invention provides a system for increasing the level and/or density of a phagocytic marker such as phosphatidylserine or a group derived from phosphatidylserine, or other phagocytic markers such as thrombospondin-1, on the surface of cells or noncellular molecular entities. The invention provides compounds, pharmaceutical compositions, and methods of their use including treatment of a variety of diseases and conditions. As described in Example 1, the inventors have shown that treating target cells with a compound of the invention significantly increased the level of phagocytosis of the target cells by macrophages. The following sections provide more details regarding certain aspects of the invention.

Phagocytic Markers

Figure 1E:
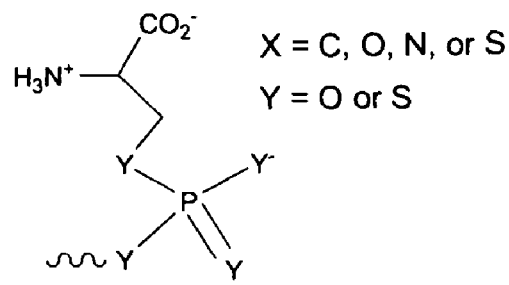
FIGS. 1E-1O show the structures of various groups derived from PS. The wavy line in each figure indicates a position where a bond may be formed to another atom.
Figure 1F:
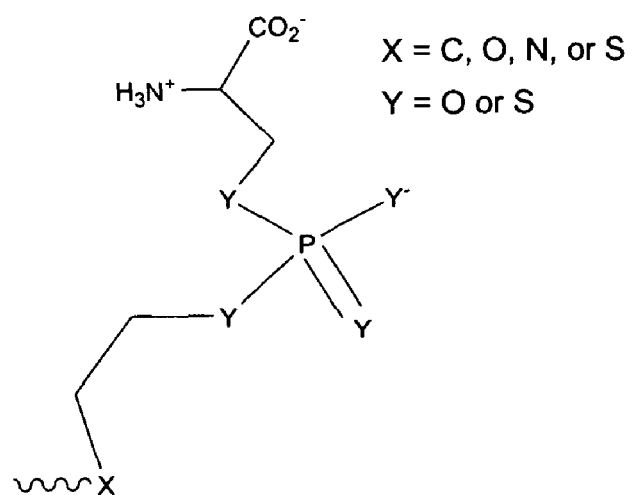
Figure 1G:
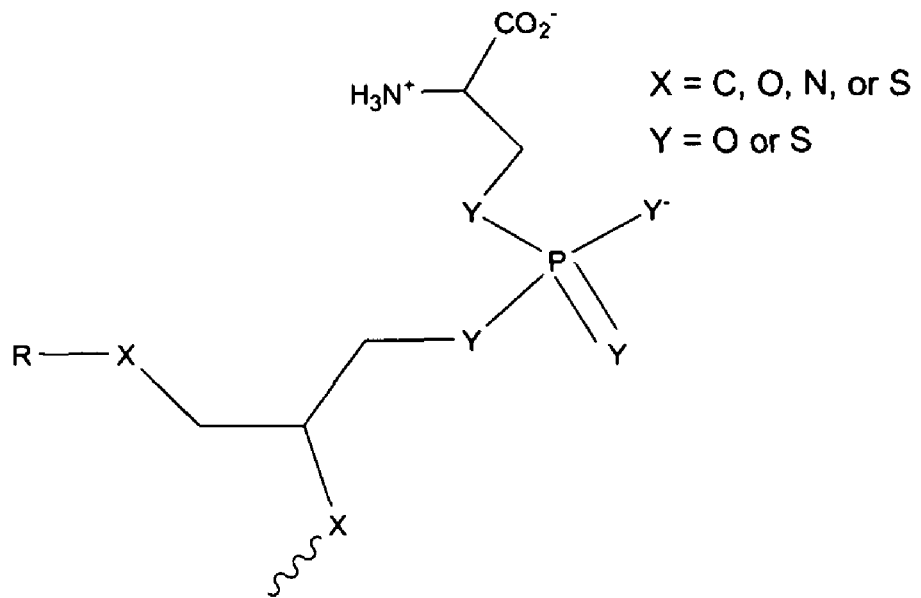
Figure 1H:
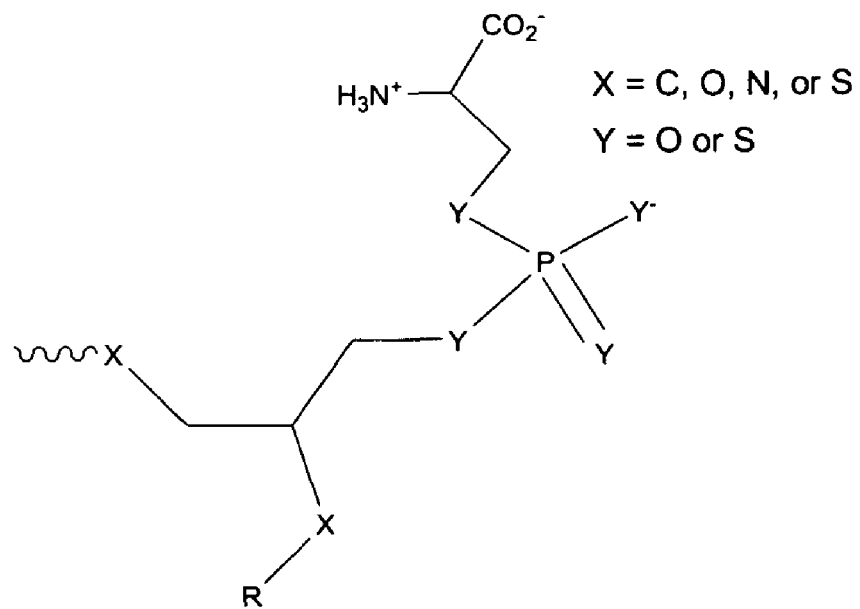
Figure 1I:
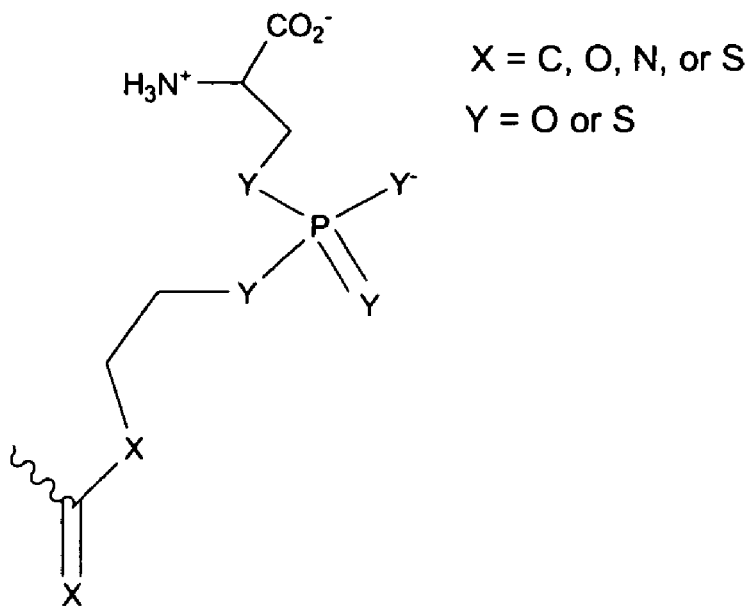
Figure 1J:
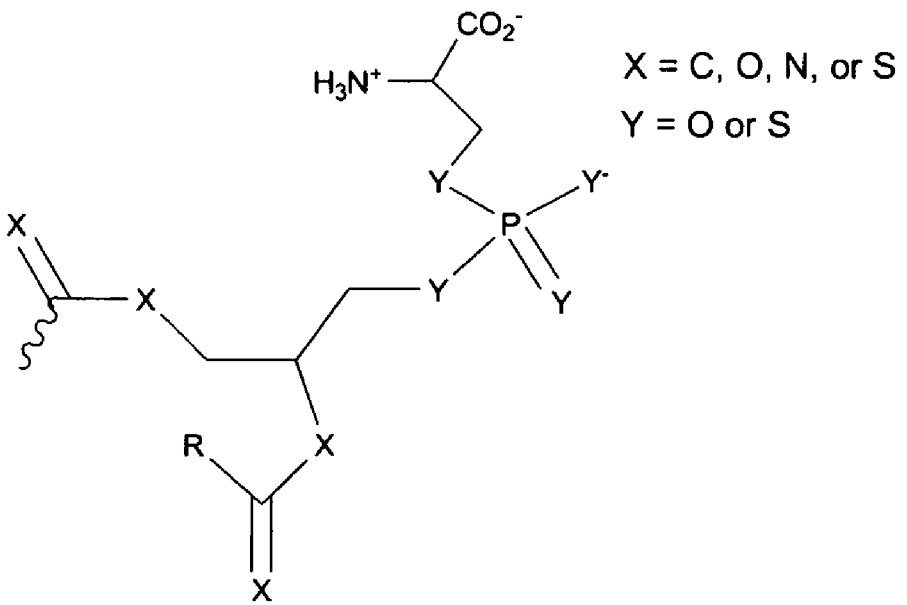
Figure 1K:
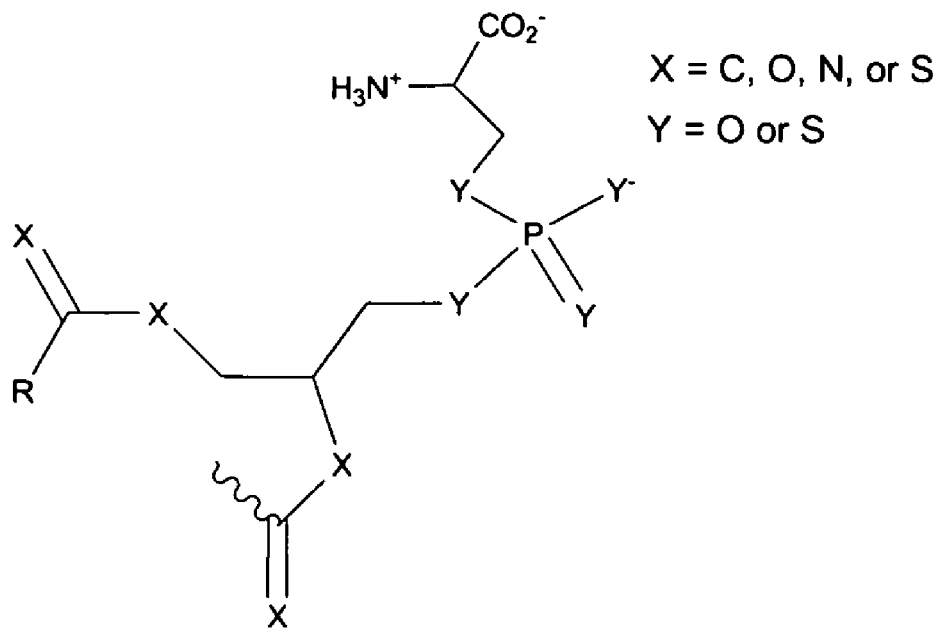
Figure 1L:
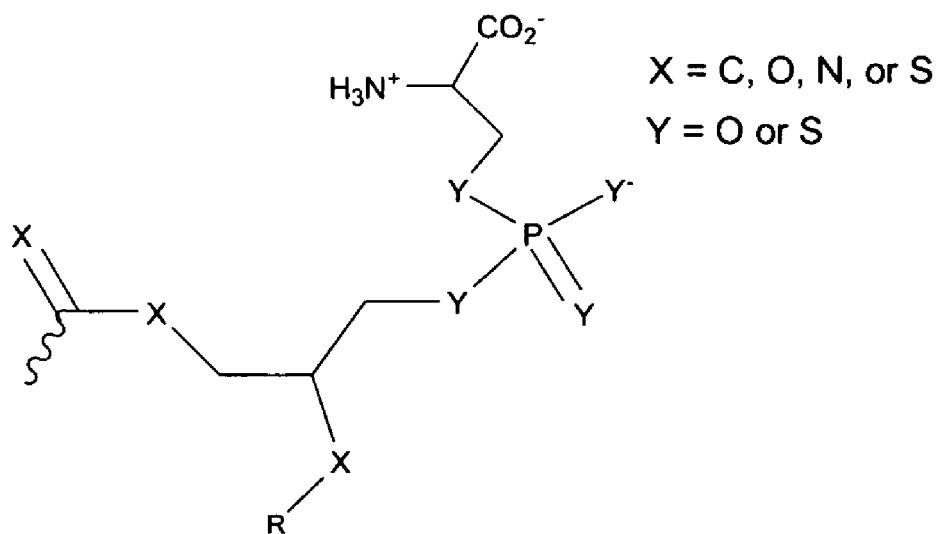
Figure 1M:
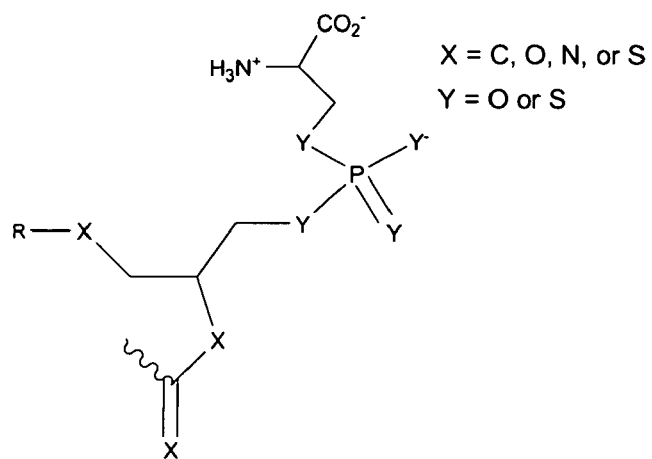
Figure 1N:
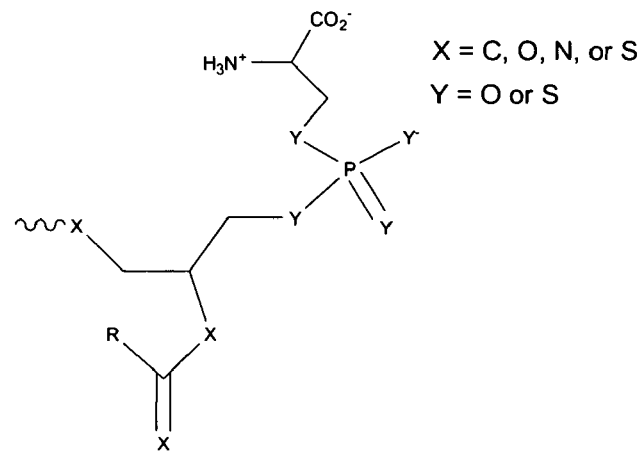
Figure 1O:
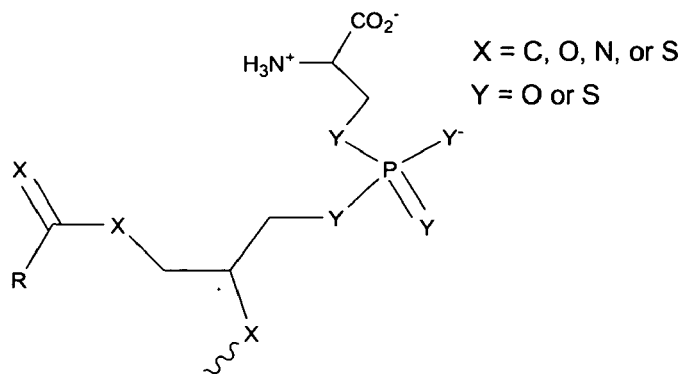

In certain particularly preferred embodiments of the invention, the phagocytic marker comprises phosphatidylserine or a group derived from phosphatidylserine, as indicated in FIGS. 1D and 1E, although any other phagocytic marker may be used.

Phosphatidylserine is a phospholipid that is naturally produced by normal, healthy cells. In such cells, it is usually present in the inner layer of the plasma membrane lipid bilayer (~15% of phospholipids in the inner layer). Occasionally, it is present on the outer layer, but typically is rapidly flipped to the inner layer. In certain abnormal cells, and particularly in apoptotic cells, phosphatidylserine becomes present on the outer layer, and therefore on the surface of cells (34). Phosphatidylserine on a cell surface acts as a signal for phagocytotic cells to initiate phagocytosis of the cell (34). Thus in accordance with the invention, increasing the level or density of phosphatidylserine on cell surfaces enhances phagocytosis.

The structure of naturally occurring phosphatidylserine is shown in FIG. 1C, in which $R_1$ and $R_2$ represent hydrocarbon chains, typically containing between 14 and 24 carbons, derived from fatty acids such as palmitic acid, oleic acid, arachidonic acid, etc. The molecule contains (i) a hydrophilic polar portion, which includes a serine-derived moiety linked to a phosphorus containing moiety derived from phosphoric acid, and (ii) a hydrophobic portion comprising the fatty acid chains, which are joined to a glycerol derived backbone through an ester linkage. In lipid bilayers such as that of the cell plasma membrane, the hydrophilic portions are typically exposed to the aqueous environment (either the extracellular or intracellular fluid), while the hydrophobic portions are buried in the interior.

While not wishing to be bound by any theory, the inventors have recognized that the role of the long hydrophobic chains in mediating recognition of PS by phagocytic cells is likely to be limited, e.g., the complete hydrocarbon chains typically found in naturally occurring PS may not be needed for recognition since much of the hydrophobic portion is buried within the plasma membrane lipid bilayer and may not be accessible. However, the interaction likely involves the hydrophilic portion, which is present at the surface of the cell membrane. Therefore, in certain embodiments of the invention, rather than delivering a complete PS molecule to cells or molecules to enhance their phagocytosis, a group derived from phosphatidylserine that contains only a portion of the PS molecule is delivered. In particular, the invention encompasses compositions that increase the level or density of a PS head group on or at the surface of a cell or molecule. FIG. 1D depicts a PS head group. FIGS. 1E-1O show a variety of other groups derived from PS, where R represents hydrogen or an aliphatic, alicyclic, heteroalicyclic, heteroaromatic moiety. In certain embodiments, R is a substituted or unsubstituted aliphatic or heteroaliphatic chain between 1 and 30 carbon atoms in length, e.g., between 6 and 14 carbon atoms in length. In certain embodiments of the invention R is a substituted or unsubstituted aliphatic or heteroaliphatic chain having a length of 5 or fewer carbon atoms, e.g., 1, 2, 3, 4, or 5 carbon atoms. In certain preferred embodiments of the invention Y=0. In certain preferred embodiments of the invention X=0. In FIGS. 1D-1O, and in other figures and formulas herein, the wavy line in each figure or formula represents a point at which another atom may be attached, e.g., to form any of the PS derivatives described herein.

The PS head group may be delivered as a portion of a derivative of PS, as further described herein. Preferably the derivative retains the ability to interact with, e.g., bind to, one or more PS receptors on a phagocytic cell. Such receptors may include, but are not limited to, CD36, CD68, CD14, LOX-1, and PS specific receptor (33, 85-90). For purposes of the present invention, a PS derivative is a molecule that comprises group derived from PS, as defined above. The derivative may consist only of a group derived from PS, e.g., a PS head group. However in general, as used herein, the term PS derivative refers to a molecule in which a group derived from PS is linked to another molecular species, e.g., covalently attached. The molecular species may be a linking molecule, such as an antibody or ligand, that facilitates attachment of the group derived from PS to a cell binding moiety or to a molecule binding moiety. The term PS derivative also refers to species in which such attachment has occurred, i.e., the molecule comprises both a group derived from PS and a cell binding moiety or molecule binding moiety. Such species are also referred to as conjugates or bifunctional molecules. The derivative may or may not be synthesized from naturally occurring phosphatidylserine.

In certain embodiments of the invention the PS derivative comprises a linker portion that is reactive with sulfhydryl (SH) groups. In certain embodiments of the invention the PS derivative comprises a linker portion that is reactive with azole, azide, imine, imide, maleimide, iodoacetamide, amide, carbamide, amine, cyano, urethane, isocyanate, lactone, lactam, oxazoline, oxazole, oxaziazole, oxazinone, isoimide, nitro, diazo, imino ester, pyridyl, aniline, quinine, quinone, imine, acyl halide quinoxaline, sulfamide, ketone, aldehyde, imidazole, carbonate, epoxide, peroxide, alkene, alkyne, carboxylic acid, anhydride, ester, hydroxyl, phenol, aromatic, halogenated, silazane, hydrazide, azo, azoxy, thioether, thioester, triazine, triazole, thiazole, silane, siloxane, or carbonyl groups or is reactive with any other chemical groups found on amino acids or small molecules.

In certain preferred embodiments of the invention, an activated ester (e.g. a succinimidyl ester or a benzotriazole ester), a carboxylic acid, an acyl chloride, an acyl bromide, or an acyl iodide on either the linker or the molecule to which is it be linked (e.g., antibody, ligand, or phagocytic marker) reacts with an hydroxyl or an amine on the other molecule (i.e., the molecule to which the linker is to be linked, or the linker, respectively), resulting in an ester or an amide, respectively. In other preferred embodiments, an iodoacetamide, an alkene, or a maleimide on either the linker or the molecule to which is it be linked (e.g., antibody, ligand, or phagocytic marker) reacts with a sulfhydryl on the other molecule (i.e., the molecule to which the linker is to be linked, or the linker, respectively), resulting in an C—S bond. In yet other preferred embodiments, a pyridyl disulfide on either the linker or the molecule to which is it be linked (e.g., antibody, ligand, or phagocytic marker) reacts with a sulfhydryl on the other molecule (i.e., the molecule to which the linker is to be linked, or the linker, respectively), resulting in a —S—S— bond. In yet other preferred embodiments, an iodo-, bromo-, or chlorosubstituted carbon on either the linker or the molecule to which is it be linked (e.g., antibody, ligand, or phagocytic marker) reacts with an hydroxyl or an amine on the other molecule (i.e., the molecule to which the linker is to be linked, or the linker, respectively), resulting in an ether or an amine (2°, 3°, or 4°), respectively.

In certain embodiments of the invention the PS derivative comprises (i) a group derived from PS; (ii) a linker portion that has reacted with a sulfhydryl azole, azide, imine, imide, maleimide, iodoacetamide, amide, carbamide, amine, cyano, urethane, isocyanate, lactone, lactam, oxazoline, oxazole, oxaziazole, oxazinone, isoimide, nitro, diazo, imino ester, pyridyl, aniline, quinine, quinone, imine, acyl halide quinoxaline, sulfamide, ketone, aldehyde, imidazole, carbonate, epoxide, peroxide, alkene, alkyne, carboxylic acid, anhydride, ester, hydroxyl, phenol, aromatic, halogenated, silazane, hydrazide, azo, azoxy, thioether, thioester, triazine, triazole, thiazole, silane, siloxane, or carbonyl group on an antibody or ligand; and (iii) an antibody or ligand bearing such a group, with which the linker has reacted so as to covalently link the group derived from PS with the antibody or ligand.

In certain embodiments of the invention an isomer of phosphatidylserine or a group derived from an isomer of phosphatidylserine, e.g., the L or D isomer, is used, of which the L isomer is generally preferred.

In certain embodiments of the invention one or both of the nonbridging oxygen atoms of the PS head group (i.e., the O atoms that are connected only to the P atom in FIG. 1D) is replaced with a sulfur atom, resulting in a thiophosphate or diothiophosphate analog. Methods for synthesizing PS analogs in which one or more of the bridging oxygens is replaced by S are known in the art (130). Other methods known to one of ordinary skill in the art can also be used. Since the sulfur may not be directly compatible with the presence of a thiol-reactive group elsewhere on the molecule, the amine on the serine may be protected by a protective group, and an amine-reactive group used effect the coupling with the ligand or antibody. Such a strategy would require an additional step to deprotect the amine of the serine, e.g., an acid treatment, prior to using the molecule.

In certain embodiments of the invention the PS derivative comprises a moiety such as an antibody or ligand that binds to a component present on or at the surface of the cell or molecular entity. By "on or at the surface of the cell or molecular entity" is meant that the component is accessible to molecules present in the extracellular environment so that it can be recognized and bound by the moiety. The component may be entirely extracellular. The component may be inserted into the cell membrane. In certain embodiments of the invention the component may be partly or entirely within the membrane, in which case the entity must partially penetrate the membrane to gain access. In general, the component is not located in the cytoplasm of a cell. For example, protein kinase C (PKC) is not considered a cellular marker. As long as a sufficient portion of the component is exposed or accessible so that it can be recognized and bound, it will be said to be present on or at the surface. In preferred embodiments of the invention the component is a cellular marker, e.g., a cell type specific marker. Where the target is a molecular entity other than a cell, the component can be any chemical entity present on or at the surface of the molecule that is recognizable by an antibody or ligand.

The component can be, e.g., a protein, peptide, mRNA or other RNA species, DNA, lipid, carbohydrate, or portion of any of the foregoing. Other molecular structures, e.g., various cellular metabolites not falling within any of the preceding categories can also be used as targets. The component can be or comprise various organic groups such as those listed above. The component can be an inorganic atom or a group containing an inorganic atom. For example, the component can be an phosphate group, sulfate group, etc.

In certain embodiments of the invention PS, or a derivative of PS comprising a PS head group, is incorporated into the lipid bilayer of a liposome, which also comprises a moiety such as an antibody or ligand that binds to a component present on or at the surface of the cell or molecule. Binding of a targeted liposome via an antibody or ligand involves specific recognition of a molecule on or at the cell surface, following which the bilayer of the liposome fuses with the lipid bilayer of a plasma membrane. The PS derivative may or may not include one or more hydrocarbon chains. If included, the hydrocarbon chain(s) may or may not be joined to a 3 carbon backbone such as the glycerol backbone in naturally occurring PS. In general, the chain(s) may be saturated or unsaturated and may optionally be substituted with and/or terminated by one or more functional groups containing a heteroatom such as O, N, S, Br, Cl, I, or P. The substitution can comprise an aromatic group. The term "unsaturated", as used herein, means that a moiety has one or more units or degrees of unsaturation.

Figure 6:
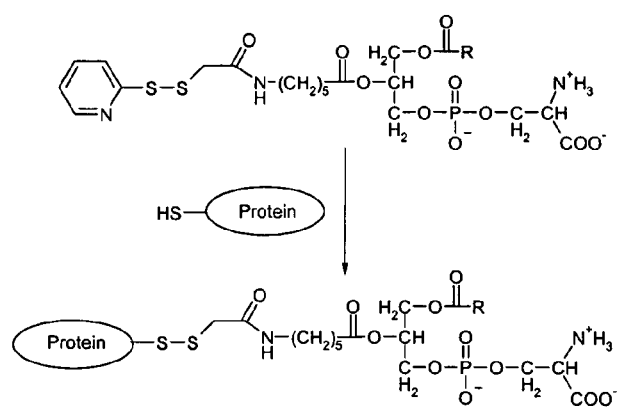
FIG. 6 shows the coupling of a thiol-reactive PS derivative with a protein containing free thiols via an S—S bond.

In certain embodiments of the invention oxidized phosphatidylserine or a derivative thereof is used (96). For example, a PS derivative comprising one or more oxidized hydrocarbon chains can be used, e.g., $R_1$ in the structures shown in FIGS. 2-3, or R in the structures shown in FIGS. 4, 6, or 12 can contain or be an oxidized hydrocarbon chain, e.g., a chain comprising between 4 and 30 carbon atoms, between 6 and 14 carbon atoms, between 14 and 24 carbon atoms, etc. Oxidation can be performed using methods known in the art, e.g., by treatment with oxidizing agents such as hydrogen peroxide, etc., or by incubation with an azo-initiator of peroxyl radicals such as 2,2'-azo-bis-(2-aminopropane) hydrochloride (96). Oxidation can be performed following synthesis of the PS derivative or a phospholipid intermediate (e.g., a phosphatidylcholine derivative) can be oxidized and used for synthesis of the oxidized PS derivative. In certain embodiments of the invention liposomes comprising oxidized PS or an oxidized PS derivative are used. These liposomes may be administered together with PS derivatives in which a group derived from PS is linked, e.g., covalently linked, to a cell-binding moiety.

In addition to PS, various other anionic phospholipids such as phosphatidylcholine and phosphatidylethanolamine are also found in living systems. In certain embodiments of the invention such anionic phospholipids, or a group derived from such an anionic phospholipid, is used as a phagocytic marker. Preferably the anionic phospholipid is one that is found naturally in or on cells, e.g., apoptotic cells. By "anionic" is meant that the phospholipid bears a net negative charge at physiological pH, e.g., at about pH 7.4.

Thrombospondins are a family of extracellular proteins that participate in cell-to-cell and cell-to-matrix communication. They regulate cellular phenotype during tissue genesis and repair. In addition, thrombospondin-1 (TSP-1) is expressed on apoptotic cells and is involved in their recognition by macrophages (33). Thrombospondin-1 is therefore another phagocytic marker that can be used to enhance phagocytosis in accordance with the invention. Macrophages recognize TSP-1 on apoptotic cells via the CD36 molecule, which is present on the surface of macrophages and may also be present on apoptotic cells (33, 44). While not wishing to be bound by any theory, it is possible that CD36/TSP1 complex on the surface of an apoptotic cell may form a ligand bridging the cell to a complex consisting of alpha(v)beta 3/CD36/ TSP1 on macrophages (33). It is possible that binding of TSP-1 to CD36 is mediated by interaction of the TSR-1 domain of TSP-1 with a conserved domain called CLESH-1 in CD36 (44). Thus in certain embodiments of the invention phagocytosis is enhanced by increasing the level or density of TSP-1, CD36, or a TSP-1/CD36 complex on the surface of a cell or molecule, e.g., by delivering the TSP-1, CD36, or TSP-1/CD36 complex to the cell. In certain embodiments of the invention a TSP-1/CLESH domain complex is delivered to the cell.

Alternatively or additionally, the phagocytic marker may comprise a molecule (e.g., MFG-E8, β2-glycoprotein, etc.) that serves as a bridging agent between macrophages and their targets, or a portion of such a molecule. Such markers may, for example, facilitate recognition of PS by macrophages or be independently recognized. Other markers that are also known to enhance phagocytosis include protein S (35), the growth arrest specific gene product GAS-6 (36), and various complement components including, but not limited to, factor B, C1q, and C3 (37). As mentioned above, MFG-E8 is a secreted glycoprotein, which is produced by stimulated macrophages and binds specifically to apoptotic cells by recognizing aminophospholipids such as phosphatidylserine. MFG-E8, when engaged by phospholipids, binds to cells via its RGD (arginine-glycine-aspartate) motif and binds particularly strongly to cells expressing alpha(v)beta(3) integrin, such as macrophages. At least two splice variants of MFG-E8 are known, of which the L variant is believed to be active for stimulating phagocytosis (68). In certain embodiments of the invention the phagocytic marker comprises the L splice variant of MFG-E8 (MFG-E8-L). In certain embodiments of the invention the phagocytic marker comprises an N-terminal domain of MFG-E8. For example, the phagocytic marker may comprise or consist essentially of amino acids 2-57 of the mature protein (signal peptide removed), or amino acids 11-66 of the unprocessed protein. In particular, the phagocytic marker may comprise or consist essentially of a polypeptide having the following sequence: CGALL-CAPSLLVALDICSKNPCHNGGLCEE-ISQEVRGDVFPSYTCTCLKGYAGNHC (SEQ ID NO: 1)

Annexin I is another phagocytic marker that may be used according to the present invention. Briefly, the 37 kDa protein annexin I (Anx-1; lipocortin 1) is a glucocorticoid-regulated protein that has been implicated in the regulation of phagocytosis, cell signaling and proliferation, and is postulated to be a mediator of glucocorticoid action in inflammation and in the control of anterior pituitary hormone release (38). Annexin I expression is elevated in apoptotic cells and appears to play a role in bridging PS on apoptotic cells to phagocytes and to enhancing recognition of apoptotic cells by phagocytes such as macrophages (39, 40). While not wishing to be bound by any theory, it is possible that the PS receptor on macrophages recognizes either annexin I or a complex containing annexin I and PS, or that annexin I facilitates recognition by aggregating PS into clusters.

In addition to phagocytosing apoptotic cells, phagocytes such as macrophages also play a role in defense against infection by engulfing certain bacterial cells. Various components present on or at bacterial cell surfaces are involved in recognition of bacteria by phagocytes and/or serve to trigger or enhance phagocytosis of the bacteria. For example, lipopolysaccharide (LPS), lipid A, and peptidoglycan moieties are known to contribute to efficient phagocytosis of bacteria. Therefore, LPS, lipid A and peptidoglycan moieties are useful as phagocytic markers in accordance with the invention. Other components present on the surface of bacteria, parasites, etc., that contribute to phagocytosis are also of use. For example, zymosan, a polysaccharide fraction found on yeast cell walls, can be used as a phagocytic marker. It is recognized by the mannose receptor and the B-glucan receptor (146).

Lipoproteins such as tripalmitylated cysteine also enhance phagocytosis as does lipoteichoic acid, and such molecules can therefore be used as phagocytic markers (146).

Various carbohydrate groups that are not typically present on the surface of mammalian cells can also serve as phagocytic markers. Phagocytes recognize glycoproteins containing mannose groups (e.g., mannans) and/or a variety of other carbohydrate groups such as fucose, N-acetylglucosamine, and glucose residues via the macrophage mannose receptor (131). The human macrophage mannose receptor (MMR) is also referred to as CD206 and has a GenBank accession number of P22897. This receptor is believed to mediate phagocytosis of yeast and other pathogenic microorganisms that have a high density of mannose at their cell surfaces. Thus carbohydrates including, but not limited to, mannose, fucose, N-acetylglusosamine, and glucose, may be used as phagocytic markers. In certain embodiments of the invention, where the phagocytic marker is a naturally occurring protein, it will be appreciated that it is frequently not necessary to use the full-length protein and that the sequence of the protein used need not be identical to that of the naturally occurring counterpart, i.e., fragments and variants of the protein can be used, provided that such fragments or variants retain their ability to enhance phagocytotic activity, which typically means that they retain their ability to be recognized by phagocytotic cells. Such fragments and variants are considered equivalents of their naturally occurring counterparts. In particular, the invention encompasses the use of phagocytic marker proteins discussed herein that differ from their naturally occurring counterparts by one or more amino acid substitutions, additions, or deletions. Each amino acid added, deleted, or altered is considered to constitute an amino acid difference. In certain embodiments of the invention a phagocytic marker protein contains 5 or fewer amino acid differences, 10 or fewer amino acid differences, 25 or fewer amino acid differences, 50 or fewer amino acid differences, or 100 or fewer amino acid differences with respect to its naturally occurring counterpart. In certain embodiments of the invention the number of amino acid differences between a naturally occurring phagocytic marker protein and a fragment or variant thereof for use in the invention is 5% or less, 10% or less, or 25% or less of the total number of amino acids in the naturally occurring protein.

In certain embodiments of the invention a fragment or derivative of a naturally occurring phagocytic marker protein is at least 70% identical, at least 80% identical, at least 90% identical, at least 95% identical, over an amino acid portion that constitutes at least 5%, at least 10%, at least 20%, at least 30%, at least 40%, at least 50%, at least 60%, at least 70%, at least 80%, or at least 90%, or 100% of the length of the naturally occurring counterpart. By at least X % identical is meant that when the protein sequences are aligned so as to produce maximum identity, allowing the insertion of gaps in either sequence where necessary to maximize identity, the number of identical residues divided by the length of the naturally occurring counterpart, and multiplied by 100, is at least X. By gap is meant a portion of a sequence that is not occupied by a residue. For example, the sequence A K L - - - S I G (SEQ ID NO: 2) contains a gap of 3 residues. The amino acid portion is preferably at least 20 amino acids in length, more preferably at least 50 amino acids in length.

Generally a fragment or variant of a naturally occurring phagocytic marker possesses sufficient structural similarity to its naturally occurring counterpart that it is recognized by a polyclonal antibody that recognizes the naturally occurring counterpart. Preferably a fragment or variant of a naturally occurring phagocytic marker possesses sufficient structural similarity to its naturally occurring counterpart that it retains the ability to bind to the surface of macrophages.

Determining whether any particular variant or fragment of a naturally occurring phagocytic marker retains the ability to enhance phagocytosis either when expressed by target cells or when incorporated into a conjugate of the invention requires only routine experimentation. For example, the variant or fragment can be introduced into or expressed in target cells, e.g., human umbilical vein endothelial cells (HUVECs), endothelial precursor cells (EPCs), etc., and phagocytosis can be assayed as described in Example 1 or using other methods known in the art. The degree of phagocytosis can be compared with the degree of phagocytosis in comparable cells not expressing the variant or fragment (which cells may, but need not, express the naturally occurring counterpart of the variant or fragment). If the degree of phagocytosis of cells expressing the variant or fragment is greater than the degree of phagocytosis of cells not expressing the variant or fragment then the variant or fragment is said to retain its ability to enhance phagocytosis.

Alternately, the variant or fragment can be used to produce a bifunctional molecule of the invention by linking (e.g., covalently linking) it to a moiety (e.g., an antibody or ligand) that binds to a cellular marker. Target cells are contacted with the conjugate and with phagocytotic cells, and the degree of phagocytosis is compared with the degree of phagocytosis that occurs when the target cells are contacted with either a conjugate that comprises the naturally occurring counterpart of the variant or fragment and a cell-binding moiety, or with the cell-binding moiety alone, or are not contacted with an exogenous compound. If the degree of phagocytosis of cells that have been contacted with the conjugate comprising the variant or fragment is greater than the degree of phagocytosis that occurs when cells are not contacted with an exogenous compound or are contacted with only the cell-binding moiety, then the then the variant or fragment is said to retain its ability to enhance phagocytosis.

Preferred variants or fragments are able to enhance phagocytosis by at least 10%, at least 20%, at least 30%, at least 40%, or at least 50% as much as their naturally occurring counterpart, more preferably by at least 60%, at least 70%, at least 80%, at least 90%, or 100% as much as the naturally occurring counterpart. It is possible that variants or fragments with greater phagocytosis-enhancing activity than the naturally occurring counterpart may be identified (132, 133).

In general, the present invention encompasses the use of peptide derivatives (e.g., peptide fragments) of the various polypeptide phagocytic markers described herein, where such peptide derivatives retain their ability to enhance phagocytosis or bind to their binding partner, respectively. For example, according to certain embodiments of the invention a derivative of annexin I, e.g., an annexin I-derived peptide is used. For example a 12 or 26 amino acid annexin I peptide has been shown to mediate many of the biological effects of annexin 1 (41,42,43). Such peptides, having the sequences Ala-Met-Val-Ser-Glu-Phe-Leu-Lys-Gln-Ala-Trp (SEQ ID NO: 3) and Ala-Met-Val-Ser-Glu-Phe-Leu-Lys-Gln-Ala-Trp-Phe-Ile-Glu-Asn-Glu-Glu-Gln-Glu-Tyr-Val-Gln-Thr-Val-Lys (SEQ ID NO: 4), respectively, can be used in the practice of the invention as can derivatives thereof (e.g., acylated derivatives) or other annexin I peptides (e.g., annexin I fragments). Certain of these peptides are commercially available (see, e.g., the web site having URL http://www.phoenix-peptide.com/cat_pep.html.

Increasing the Level or Density of a Phagocytic Marker

According to the present invention, any available strategy may be utilized to increase the level (i.e., absolute number) and/or density of phosphatidylserine or a group derived from phosphatidylserine, thrombospondin-1, or any other phagocytic marker such as annexin I, or derivatives of any of these on cells or molecules. In certain embodiments of the invention for cells, fusogenic vesicles are prepared that carry the phagocytic marker and fuse with cell membranes. Various methods have been developed in the past to make lipid vesicles fusogenic. These include, but are not limited to: coating liposomes with polyethylene glycol, polyvinyl alcohol (or other polymers), combining liposomes with viral proteins to enhance fusion (e.g. fusion protein encoded by the hemagglutinating virus of Japan), etc. Finally, lipid vesicles can be sonicated or exposed to other forms of mechanical energy to reduce their size to nanometer diameters. This will increase the surface tension of the vesicles and make them highly fusogenic.

Liposomes in which the lipid bilayer comprises phosphatidylserine can be made simply by mixing PS (or a derivative of PS comprising a PS head group and a sufficiently hydrophobic portion) with other liposome-forming lipids (34, 48). The liposome bilayer fuses spontaneously with the lipid bilayer in cell plasma membranes in a non-specific manner, and PS or the PS derivative is thus incorporated into the plasma membrane (34, 97, 98). Incorporation of a molecule into the plasma membrane in a manner akin to that of naturally occurring phospholipids in the lipid bilayer (i.e., with a hydrophilic portion exposed to the intracellular or extracellular environment and a hydrophobic portion within the interior of the bilayer), is referred to as being added or incorporated as a lipid. Liposomes containing PS or a PS derivative in their lipid bilayer may be used for the various in vitro and in vivo methods described herein. However, in preferred embodiments of the invention, the liposomes are modified to enhance their ability to specifically fuse with target cell populations, e.g., endothelial cells. This can be achieved by coating vesicles with antibodies or ligands, e.g., antibodies or ligands that bind to markers present on the target cell, by linking antibodies or ligands to the liposome, as well as by the use of viral protein components that are attached to or used to coat the liposome. Methods for making targeted liposomes (e.g., immunoliposomes, ligand-targeted liposomes) are well known in the art (91-94 and references therein). See also articles in *Advanced Drug Delivery Reviews* 56 (2004).

In certain embodiments of the invention, in addition to comprising a lipid that contains a PS head group in the liposome lipid bilayer, the liposome also contains one or more additional therapeutic agents, which may be present within an inner aqueous compartment of the liposome, partly or entirely within the lipid bilayer, or on the outer or inner surface of the liposome. The therapeutic agent(s) are delivered to the interior of target cells or to its surface. For example, to treat a tumor it may be desirable to administer a liposome comprising a lipid with a PS head group in the liposome bilayer and a standard chemotherapeutic agent in the inner aqueous compartment. The liposome is preferably targeted to tumor cells.

In other embodiments of the invention, phosphatidylserine or a group derived from PS, thrombospondin-1, or other phagocytic markers such as annexin I are delivered via association with a cellular marker, e.g., a cell type specific marker. For example, the phagocytic marker may be coupled with an antibody or ligand that binds to a marker found on the surface of target cells (cellular marker), e.g., a component such as a portion of a transmembrane protein that is present on or in the cell membrane, or a component of the cell membrane itself. Such markers include, but are not limited to, (i) receptors such as a VEGF receptor, a Tie receptor, other growth factor receptors, (ii) integrins, (iii) selectins, or (iv) any of various CD molecules. (See, e.g., the web site with URL www.ncbi.nlm.nih.gov/prow for an up-to-date description of the CD molecules, including their patterns of expression.) Various suitable cellular markers are discussed below, but the invention is not limited to use of these molecules.

In yet other embodiments of the invention a bifunctional molecule is provided that comprises a cell binding moiety and a moiety that binds to a phagocytic marker. The cell binding moiety binds to a component present on or at the surface of target cells, e.g., a cell type specific marker. The moiety that binds to a phagocytic marker binds to a phagocytic marker that is present in an extracellular fluid such as blood or interstitial fluid and/or is present on or at the surface of phagocytic cells. In the former case, phagocytes subsequently recognize and/or bind to the phagocytic marker either before or after the bivalent molecule has bound to the target cell. The phagocytic marker may be an endogenously expressed molecule or may be delivered to a subject. Multivalent molecules may also be used. Any of the cellular markers and phagocytic markers described herein can be used.

In the case of a phagocytic marker that is endogenous to a cell, the level or density of a phagocytic marker on or at the cell surface can be increased by contacting the cell with a compound that causes translocation or flipping of the phagocytic marker from the interior of the cell (e.g., from the inner leaflet of the plasma membrane), to a location on or at the surface of the cell, e.g. a phosphatidylserine translocase (141). In certain embodiments of the invention the level or density of a phagocytic marker on or at the cell surface can be increased by contacting the cell with a compound that inhibits an endogenous protein that would otherwise cause the phagocytic marker to be internalized, flipped to the inner leaf of the plasma membrane, or otherwise prevented from reaching the cell surface. The endogenous protein can, for example, be inhibited using antisense or short interfering RNAs that contain a nucleic acid complementary to a portion of the mRNA that encodes the protein. In either case, the compound can be targeted to particular cell types by linking (e.g., covalently linking) it to a cell binding moiety such as an antibody or ligand that binds to the target cells, in a similar manner to the targeting of phagocytic markers described herein. Other approaches include contacting cells with compounds (optionally targeted to particular cell types) that cause increased expression of endogenous phagocytic markers. However, in certain embodiments of the invention none of these methods (i.e., methods that involve controlling the expression or localization of endogenous phagocytic markers) is used. Instead, various other methods described herein are employed.

Cellular Markers

According to certain embodiments of the invention the cellular marker can be any marker that is expressed on or at the surface of a cell. In certain embodiments of theh invention the cellular marker is a cell type specific marker. In certain embodiments of the invention the cellular marker is selected from the group consisting of adhesion receptors integrin $\alpha_V\beta_3$, integrin $\alpha_5\beta_1$, integrin $\alpha_1\beta_1$, integrin $\alpha_1\beta_5$, integrin $\alpha_3\beta_1$, integrin $\alpha_4\beta_1$ (1-3) the family of vascular cell adhesion molecules (VCAMs) and intracellular adhesion molecules (ICAMs) (4-6) the family of P-selectins, L-selectins and E-selectins, the Tie-1 receptor, Tie-2 receptor (7, 8), VEGF receptors such as VEGFR-1, VEGFR-2, VEGFR-3, (9), EphA family members, EphB family members, ephrin A family members, ephrinB family members such as ephrinB1, ephrinB2, and ephrinB3 (10, 11), VEGF co-receptors such as neuropilin-1 and neuropilin-2 (78), laminin (12), platelet endothelial cell adhesion molecules (PECAM-1 or CD31) (13), vascular endothelial cadherin (VE-cadherin) (14, 15), fibroblast growth factor receptors (e.g. FGF-1, FGF-2) (16-18), epidermal growth factor receptor family members (e.g., EGFR, HER-2, HER-3, HER-4, HER-2/neu), other integrins than those already mentioned, other selectins than those already mentioned, CD34 (19-22), P1H12 (CD146) (46), other CD molecules, T-cell receptor chains, Major Histocompatibility Complex I and II, prominin-I (AC133) (26, 27), glypican (28, 29), proline (collagen-specific), the family of platelet-derived growth factor receptors (PDGFR) (30), tissue factor (TF) (32), endoglin (CD105), and annexin I (70). The anti-angiogenic peptide angiostatin binds to ATP synthase, angiomotin, and annexin II on endothelial cell surfaces (50-52). Thus ATP synthase, angiomotin, and annexin II are useful cell type specific markers for targeting to endothelial cells.

Additional cellular markers include angiotensin converting enzyme, aminopeptidase P, aquaporin 1, carbonic anhydrase, dipeptidyl peptidase IV, endothelin converting enzyme receptor, OX-45/CD48, PV-1, receptor for advanced glycation end products, seven transmembrane receptor, and thrombomodulin. These markers were identified as being specific for lung endothelium and are predicted to be expressed at the cell surface and thus be accessible using a technique in which subtractive proteomic mapping of the endothelial cell surface in lung and solid tumors was performed to identify cellular markers suitable for tissue-specific therapy (70). Annexin-1, annexin-8, ephrin A5, ephrin A7, myeloperoxidase, nucleolin, transferrin receptor, and vitamin D binding protein were identified as tumor-induced vascular proteins expressed in tumor-associated endothelial cells and likely to be present at the plasma membrane (70). These cellular markers may be particularly useful in the practice of the invention. Transferrin receptor is upregulated on rapidly dividing cells as a result of their increased need for iron (134) and is thus useful in particular for targeting to proliferating cells, e.g., tumor cells. Transferrin can be used as a targeting ligand for transferrin receptor (135).

Preferred markers include integrin $\alpha_V\beta_3$, integrin $\alpha_5\beta_1$, integrin $\alpha_1\beta_1$, integrin $\alpha_1\beta_5$, integrin $\alpha_3\beta_1$, integrin $\alpha_4\beta_1$, Tie-2 and CD3. Tissue factor (TF), a molecule involved in hemostasis, is another preferred marker. Briefly, tissue factor is a cell membrane-bound glycoprotein (MW 46 kDa) and a member of the class 2 cytokine receptor family. It is composed of a hydrophilic extracellular domain, a membrane-spanning hydrophobic domain, and a cytoplasmic tail of 21 residues, including a non-disulfide-linked cysteine. Upon exposure to blood, perivascular cell-bound TF binds to factor VII, a vitamin K-dependent serine protease. TF is expressed on endothelial cells lining the luminal surface of various forms of pathological neovasculature (e.g., associated with cancers such as solid tumors, diabetic retinopathy, and the exudative (wet) form of age-related macular degeneration) but typically is not expressed (or is expressed at a much lower level) in normal vasculature, thus providing a specific and accessible therapeutic target. In those embodiments of the invention in which the cell type specific marker is TF, Factor VII (or a derivative thereof) is a suitable ligand that can be used to deliver a phagocytic marker to cells expressing TF. As mentioned above, TF binds to factor VII that is normally present in the blood. By linking a phagocytic marker such as phosphatidylserine, thrombospondin-1, or a group derived from PS or thrombospondin-1 to factor VII, the phagocytic marker is targeted to cells that express TF, e.g., endothelial cells in pathological neovasculature.

Certain preferred markers include molecules that are expressed preferentially on endothelial cells and/or endothelial cell precursors, e.g., newly developing endothelial cells, angioblasts, etc. Increasing the level or density of a phagocytic marker on endothelial cells, particularly newly formed or proliferating endothelial cells, and thereby enhancing their clearance is useful for treating diseases and conditions associated with excessive or inappropriate angiogenesis or excessive or inappropriate vasculature. Such diseases and conditions include, but are not limited to, cancer, diabetic retinopathy, macular degeneration, choroidal neovascularization, atherosclerosis, restenosis, psoriasis, rheumatoid arthritis, endometriosis, menorrhagia, hemangiomas, and vascular malformations. Thus the invention provides a method of treating a condition associated with inappropriate or excessive vascular endothelial growth or angiogenesis comprising steps of (i) providing a subject at risk of or in need of treatment for a condition associated with inappropriate or excessive vascular endothelial growth or angiogenesis; and (ii) increasing the level or density of a phagocytic marker on the surface of endothelial cells. According to preferred embodiments of the invention step (ii) comprises administering a pharmaceutical composition comprising an effective amount of a moiety that binds to a component present on or in the surface of endothelial cells, wherein a molecule that is a phagocytic marker is linked to the moiety. The linkage can be covalent or noncovalent and can be direct or indirect in various embodiments of the invention.

Preferred cell type specific markers for delivering a phagocytic marker to endothelial cells include a variety of the cell type specific markers listed above, e.g., integrin $\alpha_V\beta_3$, integrin $\alpha_5\beta_1$, integrin $\alpha_1\beta_1$, integrin $\alpha_1\beta_5$, integrin $\alpha_3\beta_1$, integrin $\alpha_4\beta_1$, the family of VCAM and ICAM receptors, the family of P-selectins, L-selectins and E-selectins, Tie-1 receptor, Tie-2 receptor, VEGFR-1, VEGFR-2, VEGFR-3, Ephrin-A1, Ephrin-B2, EphB4, laminin, platelet endothelial cell adhesion molecules (PECAM-1 or CD31), vascular endothelial cadherin (VE-cadherin), CD34, tissue factor, and annexin I.

Normal microvasculature exhibits significant structural heterogeneity, and this feature is reflected by differences in gene expression and/or post-translational protein processing (e.g., glycosylation). It is possible to take advantage of these differences to target the compositions of the invention selectively to endothelial cells in particular organs or vascular beds, or to endothelial cells in different types of capillaries (e.g., continuous, fenestrated, discontinuous) (81).

In addition, tumor blood vessels differ from those found in normal organs and from newly formed blood vessels in healing wounds, inflamed tissues, and other sites of angiogenesis in a number of respects. For example, tumor vasculature displays a number of structural and functional abnormalities such as leakiness and irregular diameter. Tumor vasculature also exhibits differences in gene expression and/or post-translational protein processing with respect to vessels found elsewhere. Some molecules, e.g., aminopeptidase N (CD13), proteoglycan N2, and matrix metalloproteinases 2 and 9 are overexpressed in tumor vasculature as well as in vessels associated with other angiogenic states such as arthritis and retinal neovascularization (81).

PPARγ is a molecule that is highly expressed on tumor endothelium and is a useful cellular marker to target the compositions of the invention to endothelial cells, particularly endothelial cells present in tumor vasculature (106). Antibodies to PPARγ can be used. Numerous small molecule ligands of PPARγ are known. In particular, a number of small molecules of the thiazolidinedione class (e.g., troglitazone and rosiglitazone), are PPARγ ligands. Rosiglitazone and other thiazolidinediones have been approved for the treatment of diabetes. PPARγ ligands can be used as cell-binding moieties in composition of the invention to target a phagocytic marker to endothelial cells.

A number of other endothelial cell specific markers are known and are of use in the practice of certain embodiments of the invention. Comparison of gene expression patterns using a modification of the sequential analysis of gene expression (SAGE) technique identified a number of transcripts, referred to as pan-endothelial markers (PEMs) that were expressed at substantially higher levels in both normal and tumor-associated endothelium compared with other tissues (45). In addition, a number of markers whose expression was specifically elevated in tumor endothelium relative to normal endothelium were identified and are referred to as tumor endothelial markers (TEMs) (45).

The PEMS, listed at p. 1199 of reference 45, may be used to target phagocytic markers to endothelial cells, preferably endothelial cells in pathological neovasculature such as that which occurs in tumors or in macular degeneration. However, in certain embodiments of the invention it is preferred to employ markers that are specific for pathological neovasculature, e.g., the TEMs listed at p. 1201 of reference 45, which include TEM1-TEM9 as well as a number of previously identified proteins. In particular, TEM1, TEM5, TEM7, and TEM8 are preferred in certain embodiments of the invention as they have predicted transmembrane domains, indicating that at least a portion of the molecule is located on the cell surface (46).

Transcriptional profiling using a combined database mining, virtual subtraction, and microarray analysis approach revealed a number of genes that are differentially expressed in endothelial cells (79). Genes that were selectively expressed in endothelial cells from different vascular types were identified. Proteins encoded by such genes can be used to selectively target molecules to different subsets of endothelial cells. A number of the genes were expressed under angiogenic conditions, suggesting that they may be particularly good cellular markers to which to target the compositions of the invention for angiogenesis inhibition (79).

In vivo phage display has been used to identify peptides that bind selectively to normal endothelium in a variety of organs and also to identify peptides that bind selectively to abnormal vasculature in tumors, arthritis, and atherosclerosis (80, 81). The cell surface molecules to which the peptides bound were also identified. For example, aminopeptidase N was identified as a marker selectively expressed in tumor vasculature. These vascular "zip codes" can be used as cell type specific cellular markers in the compositions of the invention, and peptides that bind to them can be used as cell-binding moieties.

Thus a variety of different cellular markers that are specific for endothelial cells in a variety of physiological or developmental states, disease states, or locations (e.g., organs or vascular beds) within the body are known. In particular, markers are known that are specific for endothelial cells present within tumor vasculature, i.e., markers that are overexpressed in endothelial cells within tumors relative to their expression in vasculature that is not associated with a tumor (e.g., non-proliferating endothelial cells or proliferating endothelial cells in nontumor associated vasculature). Markers are also known that are specific for proliferating endothelial cells, e.g., angiogenic endothelial cells, i.e., markers that are overexpressed in endothelial cells that are actively proliferating and/or are in the process of giving rise to new vessels, relative to their expression in endothelial cells that are not proliferating and are not giving rise to new vessels. Certain markers are specific for both proliferating endothelial cells in nontumor associated vasculature and for endothelial cells in tumor vasculature.

Markers are known that are specific for endothelial cells located in vascular beds in a variety of different organ types, e.g., lung, pancreas, etc., and peptides or antibodies that bind to these markers are also known. For example, apeptides that home specifically to vasculature in brain, kidney, lung, skin, pancreas, intestine, uterus, prostate, adrenal gland, and retina have been identified (127 and references therein, all of which are incorporated herein by reference).

Thus in certain embodiments of the invention the cellular marker to which a cell-binding moiety binds can be (i) a tumor-specific endothelial cell marker; (ii) an angiogenesis-specific endothelial cell marker; (iii) an organ specific endothelial cell marker; or (iv) a marker specific for tumor vasculature or angiogenesis.

In those embodiments of the invention in which adipocytes are tagged, an adipocyte specific marker can be used. One example of a suitable marker for adipocytes is cathepsin K (31).

One of ordinary skill in the art will be able select appropriate CD molecules that are markers for a particular cell type whose phagocytosis is desired in those embodiments of the invention in which the cell type specific marker is a CD molecule. For example, according to certain embodiments of the invention CD1, CD3, CD4, CD8, CD25, CD40, CD80, CD86 is used as a cell type specific marker. CD molecules are generally present on the cell membrane of particular types of leukocytes, e.g., leukocytes that mount an immune response against transplanted organs or cause or contribute to autoimmune diseases and allergies. Increasing the level of a phagocytic markers on such cells will enhance their phagocytosis, thereby treating or preventing the afore-mentioned conditions. It is known that certain subsets of T or B cells selectively mount an immune response against particular self antigens, and these T or B cells express particular TCRs or Ig idiotypes. These particular TCRs or Ig idiotypes may also serve as cell type specific markers to enhance phagocytosis of only those T or B cell subsets that contribute to the undesirable immune response while avoiding destruction of other T or B cells.

Thus the invention provides a method of treating or preventing a condition associated with an inappropriate immune system response comprising steps of (i) providing a subject at risk of or in need of treatment for a condition associated with an inappropriate immune system response; and (ii) increasing the level or density of a phagocytic marker on the surface of leukocytes. According to preferred embodiments of the invention step (ii) comprises administering a pharmaceutical composition comprising an effective amount of a moiety that binds to a component (e.g., a marker such as a cell type specific marker) present on or in the surface of leukocytes, wherein a molecule that is a phagocytic marker is linked to the moiety. The moiety can be, for example, an antibody that binds to the component or a ligand that binds to the component. The linkage can be covalent or noncovalent and can be direct or indirect in various embodiments of the invention.

It is well known that many types of tumor cells express antigens that are not typically found on normal cells in the body, or that are found on such cells only during early stages of development, e.g., during embryogenesis. Such tumor markers or antigens are suitable cell type specific markers for purposes of targeting compositions of the invention to enhance phagocytosis of tumor cells. These markers include, but are not limited to, carcinoembryonic antigen (CEA); α-fetoprotein (AFP); MAGE family proteins (e.g., MAGE-1, MAGE-2, MAGE-3, BAGE, GAGE-1, GAGE-2); MART-1/Melan A; WNT-2; gp75; gp100; tyrosinase; mutated or overexpressed gene products such as p53, Ras, Her2/Neu, EGF receptor; viral gene products such as human papilloma virus proteins (e.g., E6 or E7), Epstein-Barr virus proteins, or hepatitis B or C virus proteins; Ig idiotypes or TCR idiotypes found on B-cell lymphoma, T-cell lymphoma, or multiple myeloma; prostate specific antigen (PSA); gangliosides such as GD2 and GD3, etc. Many such tumor specific antigens are under consideration as targets for cancer vaccines. See, e.g., Armstrong, A. C., et al., *Br. J. Radiol.,* 74: 991-1002 (2001); Finn, O., *Nat Rev Immunol.* 2003 August; 3(8):630-41, and references cited in these articles. In addition, detection of these tumor antigens forms the basis for diagnostic tests to detect the presence or recurrence of tumors.

Mucin-1 (MUC1) is a particularly interesting cellular marker. MUC1 is a heavily glycosylated protein expressed on a variety of epithelial cells which becomes overexpressed on malignant cells in a high proportion of cancers from various organs (most tumors of the lungs, breast, prostate, and pancreas) (136-138). When it is overexpressed on rapidly dividing cells, it is underglycosylated, exposing a portion of its protein sequence on malignant cells that is covered on normal cells. By developing mAbs to this exposed protein sequence of 7 amino acids, mAbs that react only with tumor cells and not with normal epithelial cells were obtained. MUC1 can be used as a marker for tumor cells or other rapidly dividing cells and/or for epithelial cells. Monoclonal antibodies that bind to the portion of the protein sequence that is exposed on rapidly dividing cells can be used for targeting specifically to those cells. Monoclonal antibodies that bind to other portions of the molecule may be used for targeting to epithelial cells. Nucleolin, which is normally a nuclear protein, is expressed on the surface of a variety of tumor cells. Nucleolin binds to GRO (g-rich oligonucleotides), which can be used as a ligand to target the bifunctional molecules of the invention to cells that express nucleolin on their surface.

In general, the association between a given tumor antigen and the particular tumor type is known in the art. For example, CEA is frequently expressed by gastrointestinal tumors, AFP is frequently expressed in hepatocellular carcinoma, and MAGE family proteins are often expressed by melanomas. Increasing the level or density of a phagocytic marker on cells that express these tumor antigens enhances their removal from the body. This approach may be particularly helpful to prevent recurrence of tumors after initial therapy, and to prevent micrometastases. In certain embodiments of the invention a phagocytic marker is linked to an antibody or ligand that is itself used for tumor therapy and also binds to a tumor marker (e.g., an antibody that binds to Her2/Neu, which is expressed by certain breast tumors). The antibody thus provides two distinct therapeutic functions. In general, the compositions of the invention may be administered together with any conventional chemotherapeutic agent, either in a single combination or separately.

Thus the invention provides a method of treating a tumor comprising steps of (i) providing a subject at risk of or in need of treatment for a tumor; and (ii) increasing the level or density of a phagocytic marker on the surface of tumor cells. According to preferred embodiments of the invention step (ii) comprises administering a pharmaceutical composition comprising an effective amount of a moiety that binds to a component present on or in the surface of tumor cells, wherein a molecule that is a phagocytic marker is linked to the moiety.

The linkage can be covalent or noncovalent and can be direct or indirect in various embodiments of the invention.

The presence of viral proteins or portions thereof on the surface of virus-infected cells contributes to the removal of these cells by the immune system via immune system processes such as cell-mediated cytotoxicity and activity of natural killer cells. Similar processes are involved in the immune response to infection by intracellular bacteria and parasites (see, e.g., French, A. R. and Yokoyama, W. M., Curr. Op. Immunol., 15:45-51; Colucci, F., et al., Nat. Immunol., 3(9): 807-813, 2002; Russell, J. H. and Ley, T. J., Annu. Rev. Immunol., 20: 323-70, 2002; Orange, J. S., et al., 3(11): 1006-1012, 2002). The inventors have recognized that such proteins or portions thereof are useful markers that are specific for virus-infected cells and may be used to target phagocytic markers to these cells, thereby enhancing their clearance. Suitable proteins include, but are not limited to, HIV gp41 or gp120, and envelope proteins of other viruses that are displayed on the surface of virus-infected cells. In addition, invasion of cells by viruses, intracellular bacteria, or parasites may lead to altered expression of host cell proteins. Such host cell proteins, which are not normally expressed by uninfected cells, are also suitable markers to target phagocytic markers to infected cells.

Thus the invention provides a method of treating or preventing infection by a virus, intracellular bacterium, or parasite comprising steps of (i) providing a subject at risk of or in need of treatment for infection by a virus, intracellular bacterium, or parasite; and (ii) increasing the level or density of a phagocytic marker on the surface of cells that are infected by the virus, intracellular bacterium, or parasite. According to preferred embodiments of the invention step (ii) comprises administering a pharmaceutical composition comprising an effective amount of a moiety that binds to a component present on the surface of cells that are infected by the virus, intracellular bacterium, or parasite, wherein a molecule that is a phagocytic marker is linked to the moiety. The linkage can be direct or indirect and can be covalent or noncovalent according to various embodiments of the invention.

Kaposi's sarcoma (KS) is a malignancy that is characterized by angiogenesis and is consistently associated with infection by human herpesvirus 8 (HHV-8), also referred to as Kaposi's sarcoma-associated herpes virus. This virus induces expression of the transmembrane receptor tyrosine kinase c-Kit (also referred to as CD117 or SCF receptor) by infected cells (66). C-Kit is therefore a suitable cellular marker to use to target phagocytic markers to KS cells as are other cellular proteins induced by HHV-8 infection (66). Monoclonal antibodies to human c-Kit are commercially available, e.g., from Chemicon International, Temecula, Calif.

HHV-8 has been implicated as a causative factor in other diseases, e.g., primary effusion lymphoma and Castleman's disease (65, 67). In individuals suffering from these diseases, lymphoid cells infected with HHV-8 express the transmembrane herpesvirus K1 protein (67). K1 is thus a suitable marker to use to target phagocytic markers to HHV-8 infected cells in individuals with these conditions. Another suitable marker to use to target phagocytotic markers to HHV-8 infected cells is the viral protein vGPCR (65)

The invention is not limited to the use of cellular markers described herein or known in the art. A number of techniques are available that could be used to identify additional markers, e.g., cell type specific markers. For example, comparison of gene expression profiles (e.g., using microarrays or SAGE) between cells of different types or states (e.g., between virus-infected cells and non-infected cells, between endothelial cells and non-endothelial cells such as fibroblasts, smooth muscle cells, or a combined reference population, between endothelial cells isolated from normal vessels and endothelial cells isolated from tumor vessels, etc., can be used to identify genes that are over-expressed in cells of a particular type relative to other cells. For example, as mentioned above, transcriptional profiling using a combined database mining, virtual subtraction, and microarray analysis approach was used to identify genes that are differentially expressed in endothelial cells (79). Protein expression can be compared using, for example, 2D gel electrophoresis, to identify proteins that are selectively expressed in a particular cell type of interest. Phage display can be used to identify peptides that bind to particular target proteins, cells, tissues, or organs under normal conditions or in various disease states (145). For example, as mentioned above in vivo phage display was used to identify peptides that bind selectively to normal endothelium in a variety of organs and also to identify peptides that bind selectively to abnormal vasculature in tumors, arthritis, and atherosclerosis (80, 81). In addition to peptides, larger protein domains, including single chain antibodies, can be displayed on the surface of phage particles, and biopanning can be used to isolate sequences that bind most efficiently.

In certain embodiments of the invention the cellular marker is of human origin, which may be preferred for applications involving human cells, e.g., for therapeutic applications in humans, for treating blood products or transplants comprising human cells, etc. In other embodiments of the invention the cellular marker is of animal origin, e.g., rodent, primate, etc., which may be useful for animal therapeutics, for in vitro applications involving animal cells, and/or for testing compositions of the invention in animal models of human disease. If a cellular marker, e.g., a cell type specific marker, is identified in animals, the human homolog(s) thereof can be identified using any of a variety of methods known in the art including, but not limited to, examination of the human genome sequence, probing human genomic or human cDNA libraries under low stringency conditions, PCR using degenerative oligonucleotides, etc. In certain embodiments of the invention the cellular marker is an allelic variant of a protein, e.g., an allelic variant whose expression is associated with disease.

Cell Binding Moieties

In general, a cell binding moiety is a molecule that comprises a portion that binds to a cellular marker. In certain preferred embodiments of the invention the cell binding moiety is linked to a phagocytic marker. In other embodiments the cell binding moiety comprises a portion that binds to another molecule to which a phagocytic marker is attached. Suitable cell binding moieties include antibodies that specifically bind to a cellular marker and ligands that specifically bind to a cellular marker. In general, the linkage between the cell binding moiety and the phagocytic marker can be covalent or noncovalent and can be direct or indirect in various embodiments of the invention.

In those embodiments of the invention in which the cell binding moiety is an antibody, the antibody may be any immunoglobulin or a derivative thereof which maintains binding ability, or any protein having a binding domain which is homologous or largely homologous to an immunoglobulin binding domain. Such proteins may be derived from natural sources, or partly or wholly synthetically produced (e.g., using recombinant DNA techniques, chemical synthesis, etc.). The antibody can be of any species, e.g., human, rodent, rabbit, goat, chicken, etc. The antibody may be a member of any immunoglobulin class, including any of the human classes: IgG, IgM, IgA, IgD, and IgE. In various embodiments of the invention the antibody may be a fragment of an antibody such as an Fab', F(ab')$_2$, scFv (single-chain variable) or other fragment that retains an antigen binding site, or a recombinantly produced scFv fragment, including recombinantly produced fragments. See, e.g., Allen, T., *Nature Reviews Cancer*, Vol. 2, 750-765, 2002, and references therein. Monovalent, bivalent or multivalent antibodies can be used. The antibody may be a chimeric or "humanized" antibody in which, for example, a variable domain of rodent origin is fused to a constant domain of human origin, thus retaining the specificity of the rodent antibody. It is noted that the domain of human origin need not originate directly from a human in the sense that it is first synthesized in a human being. Instead, "human" domains may be generated in rodents whose genome incorporates human immunoglobulin genes. See, e.g., Vaughan, et al., (1998), *Nature Biotechnology*, 16: 535-539. The antibody may be partially or completely humanized. An antibody may be polyclonal or monoclonal, though for purposes of the present invention monoclonal antibodies are generally preferred. Preferably the antibody specifically binds to its target on the cell surface, e.g., to a cell-type specific marker. Methods for producing antibodies that specifically bind to virtually any molecule of interest are known in the art. For example, monoclonal or polyclonal antibodies can be purified from natural sources, e.g., from blood or ascites fluid of an animal that produces the antibody (e.g., following immunization with the molecule or an antigenic fragment thereof) or can be produced recombinantly, in cell culture.

Antibodies that specifically bind to a number of the cellular markers described herein are commercially available. For example, antibodies that bind to various VEGF receptors are available from Chemicon International. Monoclonal antibodies that bind to TF are available from Green Mountain Antibodies, Burlington, Vt. Monoclonal antibodies that bind to integrins such as integrin alpha(v)beta(3) and to various ICAMs are available from Abcam, Cambridge, UK and Cambridge, Mass. Antibodies that specifically bind to many of the additional cellular markers mentioned herein are known to one of ordinary skill in the art. For example, monoclonal antibodies BV13 and E4G10 bind to VE-cadherin (14), which is a cellular marker expressed by endothelial cells. Of particular note, E4G10 binds to endothelial cells in a subset of tumor vasculature but not to normal vasculature. This demonstrates that certain antibodies or ligands may be cell type specific even if they bind to a molecule that is expressed in cells of multiple types. For example, the same molecule may expose different antigens to the extracellular environment depending on the cell in which it is expressed. Antibodies or ligands such as E4G10, which display binding that is more cell type specific than the marker to which they bind, are used in certain embodiments of the invention.

In certain embodiments of the invention it is preferable to use F(ab')2 or F(ab') fragments rather than antibodies that contain an Fc portion since the Fc portion may have a pro-inflammatory effect or cause other undesirable effects. However, in certain embodiments of the invention it is preferred to use antibodies comprising an Fc domain since this domain activates phagocytic cells and can thus enhance phagocytosis. F(ab')$_2$ fragments can be generated, for example, through the use of an Immunopure F(ab')$_2$ Preparation Kit (Pierce) in which the antibodies are digested using immobilized pepsin and purified over an immobilized Protein A column. The digestion conditions (such as temperature and duration) may be optimized by one of ordinary skill in the art to obtain a good yield of F(ab')$_2$. The yield of F(ab')$_2$ resulting from the digestion can be monitored by standard protein gel electrophoresis. F(ab') can be obtained by papain digestion of antibodies, or by reducing the S—S bond in the F(ab')$_2$.

In various embodiments of the invention an appropriate ligand to which a phagocytic marker is linked can be any molecule that specifically binds to a target molecule (e.g., polypeptide or a portion thereof such as a carbohydrate moiety), through a mechanism other than an antigen-antibody interaction. For example, in various embodiments of the invention a ligand can be a polypeptide, peptide, nucleic acid (e.g., DNA or RNA), carbohydrate, lipid or phospholipid, or small molecule (e.g., an organic compound, whether naturally-occurring or artificially created that has relatively low molecular weight and is not a protein, polypeptide, nucleic acid, or lipid, typically with a molecular weight of less than about 1500 g/mol and typically having multiple carbon-carbon bonds).

Ligands may be naturally occurring or synthesized, including molecules whose structure has been invented by man. Examples of ligands include, but are not limited to, hormones, growth factors, or neurotransmitters that bind to particular receptors. For example, VEGF is a ligand for the VEGFR. Thus according to one embodiment of the invention a phagocytic marker is linked to VEGF. The VEGF binds to its receptor, present on cells that express the receptor (endothelial cells), thereby providing an increased amount of the phagoctytotic marker at the cell surface. The increased amount of the phagocytic marker enhances engulfment of the cell by phagocytes. Other examples of ligands include small molecules such as glucocorticoids, which bind to glucocorticoid receptors, and neurotransmitters such as serotonin or acetylcholine (ACh), which bind to serotonin receptors or ACh receptors respectively, etc. As mentioned above, factor VII is a ligand for tissue factor and may be used to target a phagocytic marker to the surface of a cell that expresses tissue factor. In certain embodiments of the invention the ligand is a carbohydrate. Carbohydrate-binding receptors at the surface of the target cell can be targeted using carbohydrates as ligands. Similarly, lipid receptors at the surface of target cells can be targeted using appropriate lipid(s) as ligands.

A number of endogenous and synthetic polypeptides that bind to molecules associated with angiogenesis and/or present on endothelial cells or precursors thereof are known. Many of these are proteolytic fragments of larger molecules such as plasminogen, prolactin, various collagen isoforms, etc. Certain of these polypeptides inhibit angiogenesis. For example, angiostatin binds to ATP synthase, angiomotin, and annexin II on endothelial cells to inhibit endothelial cell proliferation and migration (50-52). Arresten is believed to bind integrin alpha-1 beta-1 to inhibit endothelial cell proliferation, migration, tube formation, and neovascularization (53). Canstatin is believed to bind integrin alpha-v beta-3 to inhibit endothelial cell proliferation, migration, and tube formation (54). Endostatin is believed to target integrin alpha-5 beta-1 to inhibit endothelial cell proliferation and migration and to induce apoptosis of proliferating endothelial cells (55, 56). Tumstatin binds to integrin alpha-v beta-3 on endothelial cells and inhibits their proliferation and neovascularization (57, 58). Thus angiostatin, arresten, canstatin, endostatin, and tumstatin are suitable ligands that can be used to target a phagocytic marker to the endothelial cell surface. Additional suitable ligands include the NC10 domain of collagen 15 (Restin), the C-terminal hemopexin-like domain of MMP-2, the N-terminal fragment of prolactin, and N-terminally truncated platelet factor.

Variants or fragments of the above polypeptides may also be used. For example, angiostatin is a proteolytic fragment of plasminogen that contains the first four of five structurally related domains referred to as kringle domains of plasminogen. These domains, which share considerable sequence identity and each possess a number of conserved cysteine residues, are known in the art and are found in a variety of proteins in addition to plasminogen (82, 83). Other kringle domain containing fragments of plasminogen (and kringle domains from other proteins) also exhibit anti-angiogenic activity and likely bind to endothelial cells (82). For example, polypeptides comprising kringles 1-3 or 1-5 may be more potent than angiostatin (83). In general, a polypeptide comprising 1 or more kringle domains, e.g., 1, 2, 3, 4, 5, or more kringle domains is of use to target a phagocytic marker to endothelial cells. The kringle domains may be from plasminogen or from another protein, e.g., human apolipoprotein(a) (84).

It will also be appreciated that variants of the above-mentioned polypeptide ligands differing in sequence from their naturally occurring counterparts but retaining the ability to bind to endothelial cells and/or inhibit angiogenesis can also be used. In certain embodiments of the invention a polypeptide ligand contains 5 or fewer amino acid differences, 10 or fewer amino acid differences, 25 or fewer amino acid differences, 50 or fewer amino acid differences, or 100 or fewer amino acid differences with respect to its naturally occurring counterpart. In certain embodiments of the invention the number of amino acid differences between a naturally occurring polypeptide ligand and a fragment or variant thereof for use in the invention is 5% or less, 10% or less, or 25% or less of the total number of amino acids in the naturally occurring polypeptide.

In certain embodiments of the invention a fragment or derivative of a naturally occurring polypeptide ligand is at least 70% identical, at least 80% identical, at least 90% identical, at least 95% identical, over an amino acid portion that constitutes at least 10%, at least 20%, at least 30%, at least 40%, at least 50%, at least 60%, at least 70%, at least 80%, or at least 90%, or 100% of the length of the naturally occurring counterpart. For example, variants of any of the above-mentioned polypeptides that exhibit at least 50%, at least 60%, at least 70%, at least 80%, at least 90%, or greater sequence identity, over the relevant portion of the sequence could be used. The amino acid portion is preferably at least 20 amino acids in length, more preferably at least 50 amino acids in length. Such variants are considered functional equivalents for the purposes of the present invention. Generally a fragment or variant of a naturally occurring polypeptide ligand possesses sufficient structural similarity to its naturally occurring counterpart that it is recognized by an antibody (e.g., a polyclonal or monoclonal antibody) that recognizes the naturally occurring counterpart. Antibodies that bind to a number of the polypeptide ligands mentioned above are available. For example, antibodies to endostatin, angiostatin, kringles 1-3, kringles 1-4, kringle 5, etc., are available from Alpha Diagnostic International, Inc., San Antonio, Tex. Many of the ligands themselvers are also available commercially from the same source.

Additional suitable polypeptides can be identified by a number of different approaches. For example, angiogenic peptides that bind to cell type specific markers such as VEGFR family members, Tie-2, etc., can be modified to obtain derivatives that retain binding ability but are no longer angiogenic. The polypeptide can be analyzed to identify appropriate sites for modification, or random modification can be performed. Binding assays and angiogenesis assays known in the art can be used to identify suitable peptides (76). For example, hydrophobic analysis and comparative sequence/structure analysis allowed the identification of a peptide with sequence WTIIQRREDGSVDFQRTWKEYK (SEQ ID NO: 5), which binds to Tie-2 and inhibits binding of angiopoitein-2 (76). Phage display can also be used. For example, phage display identified a short peptide with sequence NLLMAAS (SEQ ID NO: 6) that binds to Tie-2 but does not stimulate angiogenesis and actually exhibits anti-angiogenic properties (77). Molecular modeling can be used to design peptides that mimic protein recognition domains. This approach has been used to identify peptide ligands of CD4 and CD8 (140).

Peptide ligands known to bind to human tumor vasculature and, in some cases, to the tumor cells themselves include CTTHWGFTLC (SEQ ID NO: 7), CLRSGRGC (SEQ ID NO: 8), CLRSGKGC (SEQ ID NO: 9), CLRSGHGC (SEQ ID NO: 10), CLRSGTGC (SEQ ID NO: 11), CXXXCXYGFCXXC (SEQ ID NO: 12), and CXXXCXWGFCXXC (SEQ ID NO: 13), which bind to and inhibit MMP-2 and MMP-9. These ligands were isolated by phage display and home to tumors and tumor vasculature of human tumors implanted in the mouse (142). A VEGFR antagonizing peptide, which binds to and inhibits VEGFR, was also identified using phage display and has the following sequence:

```
WHSDMEWWYLLG (143).        (SEQ ID NO: 14)
```

Phage display was also used to identify peptides that specifically bound to vasculature in a variety of different organs in humans and are useful as cell type specific or organ specific ligands in the present invention (144). Prostate-specific peptides include RRAGG (SEQ ID NO: 15), RRAGGS (SEQ ID NO: 16), for which IL-11R is the target). The conservation of the AGG sequence in these two peptides suggests that AGG may serve as prostate-specific ligand. Bone marrow specific peptides include PGGG (SEQ ID NO: 17) (GGG conserved). Adipose-specific peptides include EGGT (SEQ ID NO: 18) and TGGE (SEQ ID NO: 19) (GG conserved) and also GPSLH (SEQ ID NO: 20). Muscle-specific peptides include GGSVL (SEQ ID NO: 21) and LVSGY (SEQ ID NO: 22). Skin-specific peptides include GRRG (SEQ ID NO: 23) (GRR conserved), HGGG (SEQ ID NO: 24), PHGG (SEQ ID NO: 25), and VTGXSG (SEQ ID NO: 26).

Polypeptides whose sequence comprises, consists of, or is contained within any of the polypeptide and peptide ligands mentioned herein may be used. For example, in certain embodiments of the invention the ligand is selected from the group consisting of polypeptides whose sequence comprises at least 5 contiguous amino acids contained within the nucleotide sequence of Factor VII, angiostatin, arresten, canstatin, endostatin, tumstatin, annexin II, restin, a kringle domain, kringle domains 1-3 of plasminogen, kringle domains 1-4 of plasminogen, kringle domains 1-5 of plasminogen, the C-terminal hemopexin-like domain of MMP-2, the N-terminal fragment of prolactin, N-terminally truncated platelet factor, or any of SEQ ID NOs: 6-26. In certain embodiments the ligand comprises at least 10, at least 15, at least 20, at least 25, or at least 50 contiguous amino acids contained within the foregoing polypeptides (if the polypeptide is long enough to contain such a sequence). A first sequence is "contained within" a second sequence if the entire first sequence occurs in the second sequence, including terminal amino acids.

A number of ligands for endothelial cell specific markers are known that stimulate angiogenesis. For example, VEGF binds to the VEGFR, and stimulates angiogenesis. In general, although such molecules are endothelial cell specific ligands, it may be preferable not to use them for cell-targeting purposes in order to avoid possibly stimulating angiogenesis.

However, non-active variants of endogenous angiogenic polypeptides, i.e., variants that are similar in sequence to a naturally occurring angiogenic polypeptide, are suitable for use.

In certain embodiments of the invention the ligand is an aptamer that binds to a cell type specific marker. In general, an aptamer is an oligonucleotide (e.g., DNA or RNA or) that binds to a particular protein. Aptamers are typically derived from an in vitro evolution process called SELEX, and methods for obtaining aptamers specific for a protein of interest are known in the art. See, e.g., Brody E N, Gold L. *J Biotechnol.* 2000 March; 74(1):5-13.

Small molecules can also be used as ligands. For example, thiazolidinediones are ligands for the PPARγ protein, as mentioned above. Small molecules that bind to CD4 (e.g., TJU103) are known and could be used as ligands for CD4 (140). A dihydrodipyrazolopyridinone ligand for CD80 has been identified (147). 4-[2-(3,4,5,6-tetrahydropyrimidin-2-ylamino)ethoxy]-benzoyl-2-(5)-aminoethylsulfonylamino-beta-alanine has been identified as a ligand that binds to alpha(v)beta(3) (148). Variants and derivatives of these molecules, e.g., molecules within the same chemical class and having similar structural features, can also be used. Thus it is evident that small molecule ligands exist for a number of cellular markers, and it is possible to identify such ligands using methods known in the art. For example in vitro sreening of small molecule libraries, including combinatorial libraries, and computer-based screening, e.g., to identify small organic compounds that bind to concave surfaces (pockets) of proteins, can identify small molecule ligands for numerous proteins of interest (140).

In preferred embodiments of the invention cell binding moieties are not proteins or molecules that are typically used as carriers and conjugated to antigens for the purpose of raising antibodies. Examples are carrier proteins or molecules such as bovine serum albumin, keyhole limpet hemocyanin, bovine gamma globulin, and diphtheria toxin. In preferred embodiments of the invention the cell binding moiety is not β2 glycoprotein.

Compositions Comprising a Cell Binding Moiety and a Phagocytic Marker and Synthesis Thereof In accordance with certain embodiments of the invention, a composition comprising a phosphatidylserine molecule or other molecule containing one or more groups derived from PS, preferably comprising a PS head group, and a cell binding moiety such as an antibody or ligand are contacted with cells and/or administered to a subject. According to certain preferred embodiments of the invention a phosphatidylserine molecule or other molecule containing one or more groups derived from PS, preferably comprising a PS head group, is linked (e.g., covalently bonded) to an antibody or ligand that binds to a marker present on the surface of cells whose phagocytosis is desired, e.g., endothelial cells in blood vessels supplying tumors, leukocytes, tumor cells, or virus-infected cells.

Figure 2B:
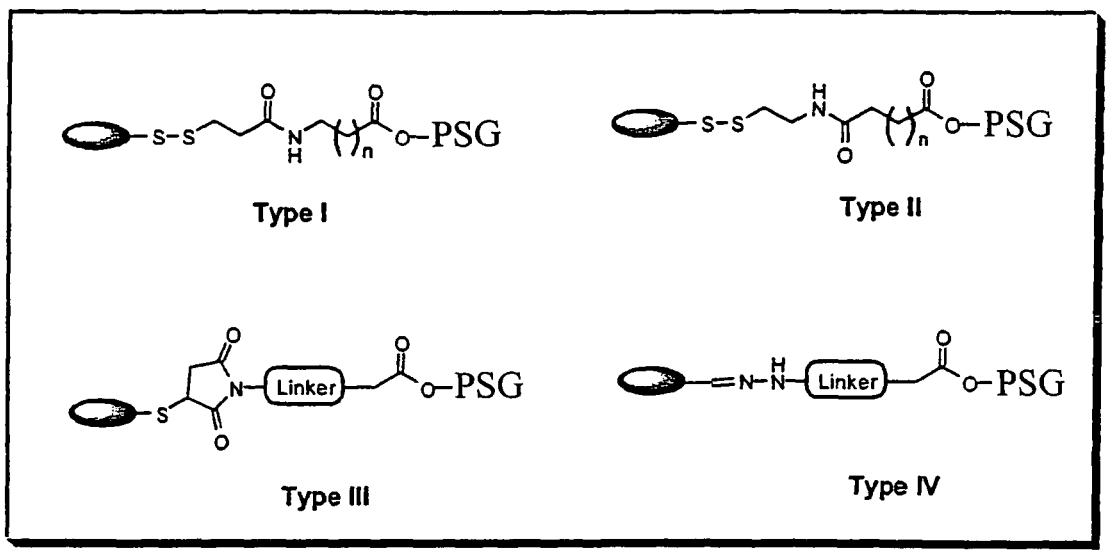
FIG. 2B shows four different linkage strategies to form conjugates in which a protein such as an antibody or a ligand that binds to a molecular target, e.g., a cellular marker on or at the surface of a target cell, is covalently linked to a group derived from PS (PSG).
Figure 2B:
Figure 3:
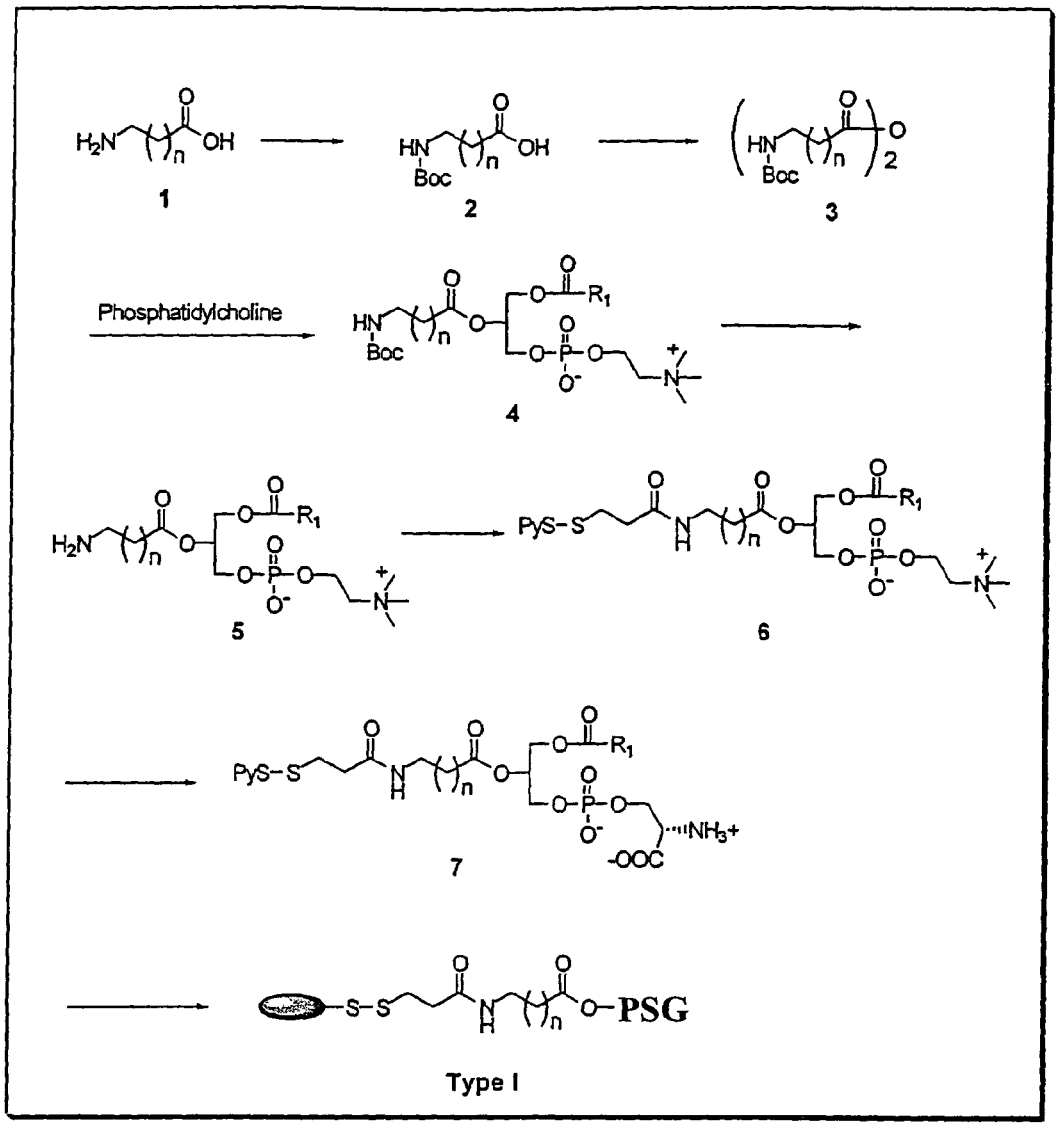
FIG. 3 shows details of a synthetic scheme to attach a group derived from phosphatidylserine to an antibody or ligand.

As shown in FIG. 2B, a lipid such as phosphatidylserine or a group derived from PS may be linked to a carrier, e.g., a protein such as an antibody or to a ligand by a variety of different linkage strategies. In general, methods for synthesizing the lipid-carrier conjugates of FIG. 2B are well known in the art. For example, a more detailed strategy for attaching a group derived from phosphatidylserine to an antibody or ligand is depicted in FIG. 3. FIGS. 4-11 provide more details of methods to synthesize a PS derivative in which a group derived from PS is linked to an antibody or ligand. (See also U.S. Pat. No. 6,300,308 and reference 48). If desired, multiple phosphatidylserine molecules or groups derived therefrom may be linked to a single antibody or ligand, provided that such linkage does not interfere too greatly with binding of the antibody or ligand to its target. Binding of the antibody or ligand to its target may be measured using methods known in the art, e.g., competitive radioimmunoassay, ELISA, etc.

In other embodiments of the invention TSP-1 or another phagocytic marker such as annexin I is linked (e.g., covalently attached) to an antibody or ligand that binds to a marker present on the surface of cells whose phagocytosis is desired, e.g., endothelial cells in blood vessels supplying tumors, leukocytes, tumor cells, or virus-infected cells. Any of a number of suitable linkage methods can be used, as discussed below.

A number of variations are possible. For example, a phagocytic marker can be linked to an antibody or ligand that binds to a cell type specific marker. Alternately, an antibody or ligand that binds to a cell type specific marker can be linked to a carrier such as an antibody or other protein that does not bind directly to the cell type specific marker, and one or more phagocytic marker can also be linked to the carrier. Multiple different cell type specific markers or phagocytic markers can be used, and different combinations can be employed. For example, it may be desirable to target endothelial cells in vessels that supply a tumor and also to target the tumor cells themselves. It may be desirable to deliver multiple different phagocytic markers to the same cell, or to different cells in the body. Multiple phagocytic markers (either the same or different) may be attached to a single antibody or ligand. A molecule that combines one or more phagocytic marker with antibody or ligands to two or more cell type specific markers might have a higher specificity or a higher affinity toward a particular target cell than a molecule that contains an antibody or ligand that binds to a single cell type specific marker.

The compounds described herein may be produced using a variety of methods, some of which are described below. It is noted that for purposes of the present invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. It will be appreciated as described below, that a variety of compounds can be synthesized according to the methods described herein. In general, the starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1989, "Comprehensive Organic Transformations", VCH Publishers. These schemes are merely illustrative of some methods by which the compounds described herein can be synthesized, and various modifications to these schemes can be made and will be suggested to a person of ordinary skill in the art having regard to this disclosure.

Furthermore, it will be appreciated by one of ordinary skill in the art that the synthetic methods, as described herein, utilize a variety of protecting groups. By the term "protecting group", it is meant that a particular functional moiety, (e.g., amine, hydroxyl, carboxylic acid, ketone, aldehyde, thiol, imine) or atom, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

In general, phagocytic markers and other compounds can be linked to targeting agents such as antibodies or ligands by any of a number of methods that are well known in the art. Examples include, but are not limited to, the glutaraldehyde method, which couples primarily through the α-amino group and ε-amino group, maleimide-sulfhydryl coupling chemistries (e.g., the maleimidobenzoyl-N-hydroxysuccinimide ester (MBS) method), and periodate oxidation methods, which specifically direct the coupling location to the Fc portion of the antibody molecule. In addition, numerous crosslinking agents are known, which may be used to link the antibody or ligand to the phagocytic marker. Suitable crosslinking agents include, e.g., carboiimides, N-Hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), etc. According to certain embodiments of the invention additional moieties are conjugated to the antibody or ligand, e.g., compounds such as polyethylene glycol (PEG), or variants thereof, that stabilize the antibody or ligand, reduce its immunogenicity, increase its lifetime in the circulation, and/or increases its resistance to degradation. Methods for adding PEG to proteins and for optimizing protein properties by doing so are well known in the art. See, e.g., references 71-75. In certain embodiments of the invention rather than adding PEG or variants thereof to the antibody or ligand, the phagocytic marker is derivatized.

For additional information on conjugation methods and crosslinkers see generally the journal *Bioconjugate Chemistry*, published by the American Chemical Society, Columbus Ohio, PO Box 3337, Columbus, Ohio, 43210. See also "Cross-Linking", Pierce Chemical Technical Library, available at the Web site having URL www.piercenet.com and originally published in the 1994-95 Pierce Catalog and references cited therein and Wong S S, *Chemistry of protein Conjugation and Crosslinking*, CRC Press Publishers, Boca Raton, 1991; and G. T. Hermanson, *Bioconjugate Techniques*, Academic Press, Inc., 1995. The following section presents a number of examples of specific conjugation approaches and cross-linking reagents. However, it is to be understood that the invention is not limited to these methods, and that selection of an appropriate method may require attention to the properties of the particular phagocytic marker and/or the properties of the antibody or ligand.

According to certain embodiments of the invention a bifunctional crosslinking reagent is used to couple a phagocytic marker with an antibody or ligand. In general, bifunctional crosslinking reagents contain two reactive groups, thereby providing a means of covalently linking two target groups. The reactive groups in a chemical crosslinking reagent typically belong to the classes of functional groups—including succinimidyl esters, maleimides, pyridyldisulfides, and iodoacetamides. Bifunctional chelating agents may also be used.

The most common schemes for forming a heteroconjugate involve the indirect coupling of an amine group on one biomolecule to a thiol group on a second biomolecule, usually by a two- or three-step reaction sequence. The high reactivity of thiols and their relative rarity in most biomolecules make thiol groups good targets for controlled chemical crosslinking. If neither molecule contains a thiol group, then one or more can be introduced using one of several thiolation methods. The thiol-containing biomolecule may then be reacted with an amine-containing biomolecule using a heterobifunctional crosslinking reagent, e.g., a reagent containing both a succinimidyl ester and either a maleimide, a pyridyldisulfide, or an iodoacetamide. Amine-carboxylic acid and thiol-carboxylic acid crosslinking may also be used. For example, 1-Ethyl-3-(3-dimethylaminopropyl)carbodiimide (EDAC) can react with biomolecules to form "zero-length" crosslinks, usually within a molecule or between subunits of a protein complex. In this chemistry, the crosslinking reagent is not incorporated into the final product. The water-soluble carbodiimide EDAC crosslinks a specific amine and carboxylic acid between subunits of allophycocyanin, thereby stabilizing its assembly. See, e.g., Yeh S W, et al., "Fluorescence properties of allophycocyanin and a crosslinked allophycocyanin trimer.", *Cytometry* 8, 91-95 (1987).

Several methods are available for introducing thiols into biomolecules, including the reduction of intrinsic disulfides, as well as the conversion of amine, aldehyde or carboxylic acid groups to thiol groups. Disulfide crosslinks of cystines in proteins can be reduced to cysteine residues by dithiothreitol (DTT), tris-(2-carboxyethyl)phosphine (TCEP), or or tris-(2-cyanoethyl)phosphine. Amines can be indirectly thiolated by reaction with succinimidyl 3-(2-pyridyldithio)propionate (SPDP) followed by reduction of the 3-(2-pyridyldithio)propionyl conjugate with DTT or TCEP. Amines can be indirectly thiolated by reaction with succinimidyl acetylthioacetate followed by removal of the acetyl group with 50 mM hydroxylamine or hydrazine at near-neutral pH. Amine can be directly thiolated by reaction with 2-iminothiolane, which preserve the overall charge of the molecule and introduces a free thiol. Tryptophan residues in thiol-free proteins can be oxidized to mercaptotryptophan residues, which can then be modified by iodoacetamides or maleimides.

Figure 4A:
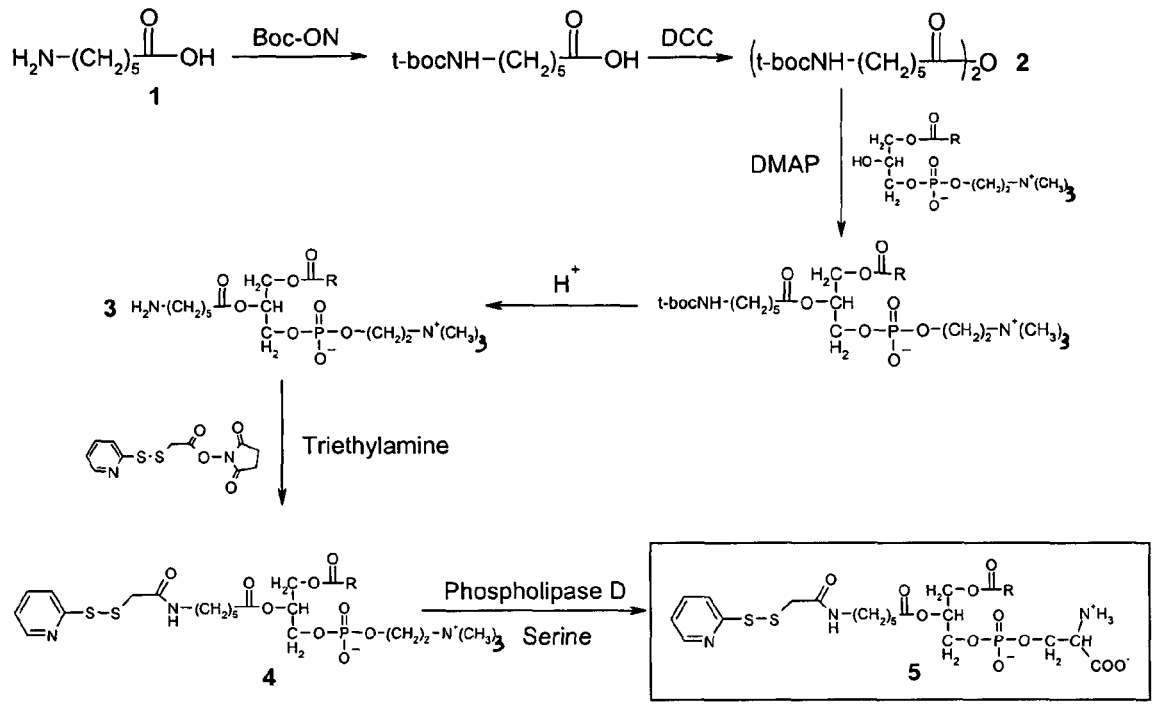
FIG. 4A shows a more detailed synthetic scheme to synthesize a phosphatidylserine derivative that can be easily reacted with thiols.

FIG. 4A presents a scheme for obtaining a PS derivative that can be easily reacted with thiols. This molecule can be coupled with proteins (or peptides) that have been previously reacted with imidothiolane to functionalize them to display thiols (FIG. 6) (47). This approach is modular and enables the coupling of a group derived from PS to a various proteins with equal ease. Most of the synthetic scheme shown in FIG. 4A employs conventional amino acid chemistry. The detailed synthetic protocols involved in the synthesis of the thiol-reactive PS derivative 5 have been described in the literature and are summarized here[47,48]. Briefly, protecting the commercial amino acid 1 with a t-butoxycarbamate (BOC) group and reacting it with dicyclohexylcarbodiimide (DCC), a coupling agent, yields the reactive anhydride 2. This anhydride is very reactive and readily reacts with a commercially available phosphatidylcholine derivative that contains a 2° alcohol. Deprotecting the BOC group using acidic conditions yields the amine-functionalized phosphatidylcholine derivative 3. Reacting this amine with a hydroxysuccinimide-activated (NHS) ester containing a pyridyl disulfide group yields the amide 4 that contains a thiol-reactive disulfide group. Phospholipase D and serine are used to convert the phosphatidylcholine derivative into the desired PS derivative 5. The R group in FIG. 4A can be any of a wide variety of groups. For example, the R group can be a linear hydrocarbon chain, which may be saturated or unsaturated, and which can vary in length and can be substituted or unsubstituted. Typically the chain contains between 6 and 30 carbons, more typically between 14 and 24 carbons, inclusive. Without wishing to be bound by any theory, it may be desirable to use PS derivatives in which the R group is relatively short in order to reduce the hydrophobicity of the compound. Therefore, in certain embodiments of the invention R contains 5 or less carbon atoms, e.g., 1, 2, 3, 4, or 5, or an H or OH may be present instead. Alternatively, rather than an ester group, an ether could be used. Further details are provided below. Hydrocarbon chains can also be attached directly to a carbon in the carbon chain that forms the backbone of the molecule (the glycerol-derived portion) via a carbon-carbon bond or any other bond that is stable under physiological conditions.

Figure 4B:
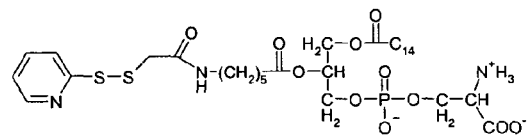
FIG. 4B shows a species of the phosphatidylserine derivative of FIG. 4A, in which R is a 14 carbon hydrocarbon chain.
Figure 4C:
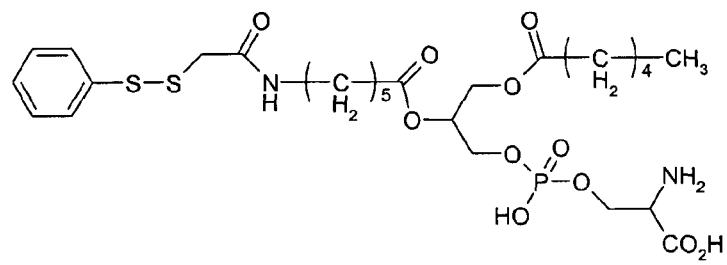
FIG. 4C shows a species of the phosphatidylserine derivative of FIG. 4A, in which R is a 5 carbon hydrocarbon chain.
Figure 5:
FIG. 5 shows the reaction of a protein with imidothiolane to generate free thiols.

In certain embodiments of the invention the PS head group is attached to the middle C of the glycerol backbone while the disulfide containing moiety is attached to the terminal C at the position occupied by the PS head group in FIG. 4A. In other embodiments of the invention the R-containing moiety is attached to the middle C of the glycerol backbone while the disulfide containing moiety is attached to the terminal C at the position occupied by the R-containing moiety in FIG. 4A. FIG. 4B shows an example in which the group is $C_{14}$. FIG. 4C shows an example in which the group is $C_5$.

The pyridyl-functionalized disulfide bond is a classical thiol-reactive group and will readily react with free thiols, such as the ones resulting from the reduction of the disulfide bridges of antibodies or the reaction of a protein with 2-iminothiolane through the protein's surface lysines (FIG. 5) (47). It is noted that antibodies have a number of disulfide bridges, some of which are more reactive toward reduction than others. It is therefore possible to reduce some disulfide bridges in an antibody (or antibody fragment) and leave others untouched, resulting in antibodies that still have their binding domain relatively intact, but with some other region "split open", displaying a few free —SH groups. This method has been used to attach groups to antibodies.

Returning to FIG. 5, reacting molecule 5 with a protein containing free thiols yields a protein-PS group conjugate with a short linker in good yield (FIG. 6) (48). The protein contains roughly one PS group per available thiol and does not have to be a 1:1 conjugate. This coupling is general enough to enable the coupling of a variety of proteins and peptides to PS or a group derived from PS. A variety of linkers combining NHS esters and thiol-reactive groups are available through companies such as Pierce (www.piercenet.com). Additional chemicals can be purchased from suppliers such as Aldrich (www.sigmaaldrich.com) or from Acros Organics (www.fishersci.com/acros).

Figure 7:
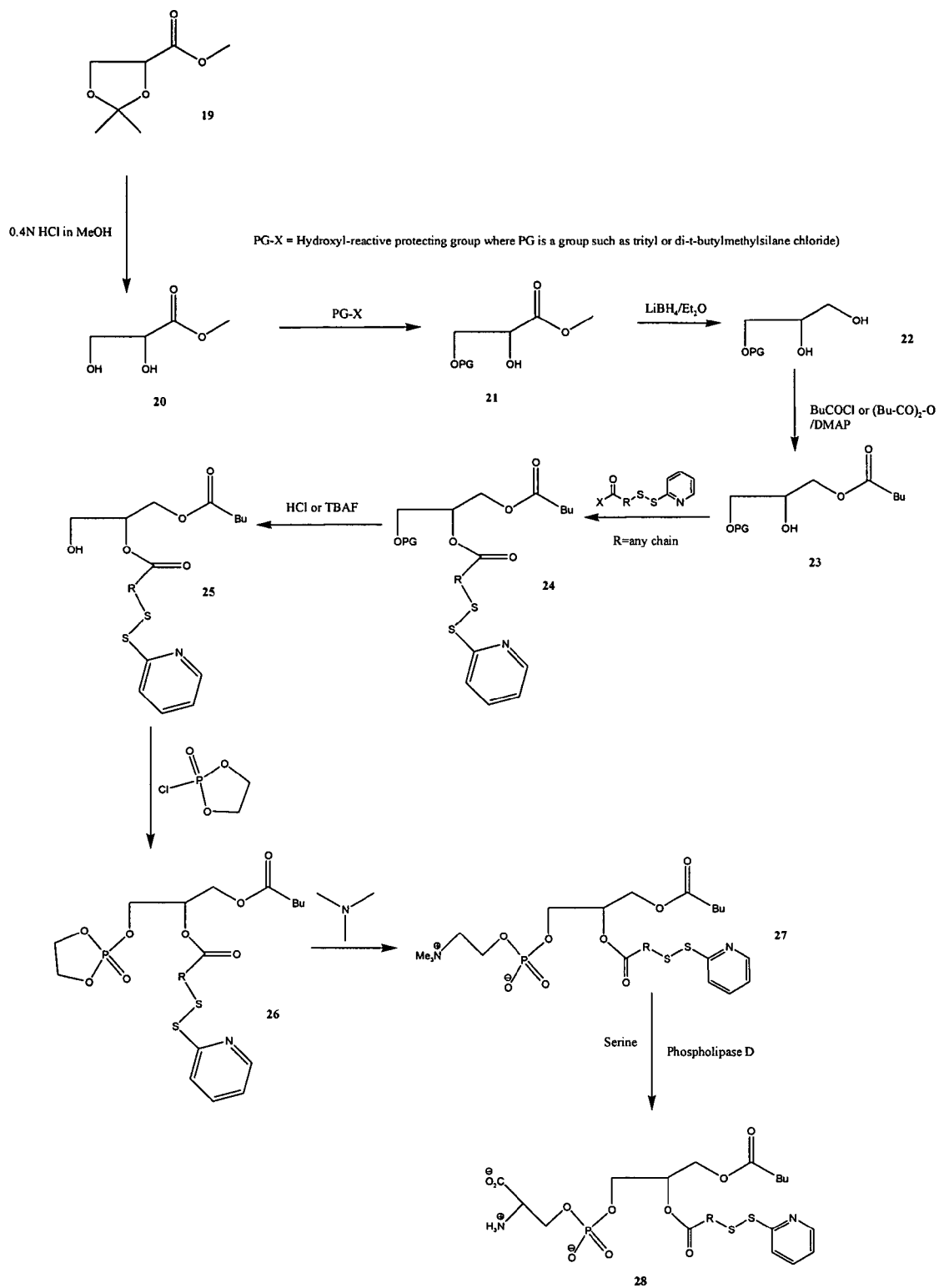
FIG. 7 shows a second synthetic scheme to synthesize a phosphatidylserine derivative that can be easily reacted with thiols.

FIG. 7 presents another scheme for obtaining a PS derivative that can be easily reacted with thiols. As described above, the final product can be coupled with proteins (or peptides) that have been previously reacted with imidothiolane to functionalize them to display thiols (FIG. 6) (47). According to the scheme shown in FIG. 7, the commercially available acetal 19 (Sigma-Aldrich) is cleaved in acidic conditions to yield the dihydroxy compound 20. The terminal hydroxyl of compound 20 is reacted with a conventional hydroxyl-protecting group such as trityl or di-tert-butylmethylsilane. In one embodiment, compound 20 is reacted with one equivalent of pyridinium triphenylmethyl tetrafluoroborate to yield a protected hydroxyl 21. The terminal hydroxyl, being a primary alcohol, will be more reactive than the other hydroxyl, which is a secondary one and more sterically encumbered. Compound 21 is reduced with lithium borohydride to turn the ester into a terminal hydroxyl 22. This terminal hydroxyl is reacted with an activated acid, such as an anhydride or an acyl chloride to yield an ester, in the presence of a base. Different activated acids can be used to yield different esters, depending on the properties desired in the final compound. The secondary hydroxyl of compound 23 is reacted with a linker that contains a thiol-reactive group, such as a reactive disulfide. Again, an activated acid is used to react with the hydroxyl in order to yield an ester 24. The thiol-reactive acid that is used to react with the secondary hydroxyl can be varied.

It will be appreciated that the linking R group shown in FIG. 7 and in other synthetic schemes described herein can be any of a number of different moieties that are conventionally used in bioconjugates. For example, R can be a linear saturated hydrocarbon chain (such as —$CH_2$— or —$CH_2$—$CH_2$—). In certain embodiments of the method R is an unsaturated chain (such as —CH=CH—, —$CH_2$—CH=CH—, a cyclic structure, or an aromatic ring). In various embodiments of the method R may also represent or contain other functionalities such as ethers (—$CH_2$—O—$CH_2$—), amides (—CO—$NH_2$—), esters (—CO—O—), imines (—C=N—), thioethers (—C—S—C—), etc. Many conventional linkers contain oligo(ethylene glycol) groups (—O—$CH_2$—$CH_2$—)$_n$ (where n is the number of repeating units) as these groups are known to be water soluble, flexible, biocompatible and non-interacting toward most biomaterials (such as proteins). R can represent or contain a moiety such as a sulfate group (—$SO_3H$), which would impart negative charges to the molecule and may increase its water solubility. R may also represent or contain a group that chelates metals or a metal-containing group, which would allow use of the compounds for imaging purposes (in the case of radioactive metals or contrast agents for MRI or CT, etc.) or for therapy (in the case of toxic metals, which can include radioactive metals).

The foregoing examples are included for descriptive purposes and are not intended to be limiting. In general, important criteria are to have a chain that positions the linked moieties in the optimal position relative to one another and that is stable and unreactive in the conditions in which the molecule will be used (e.g., physiological conditions in the case of the present invention). The optimal positioning of the moieties often involves putting some distance between them so they will not interfere with one another too much and using a flexible linker, which allows the moieties to take many different orientations relative to one another as to be able to orient themselves optimally for their intended purpose (e.g., binding to their respective receptor/ligand). In general, in various embodiments of the invention, the linker can be or comprise an aliphatic, alicyclic, heteroaliphatic, heteroalicyclic, aromatic, heteroaromatic moiety.

Returning to the scheme shown in FIG. 7, the hydroxyl-protecting group is removed using a reagent such as hydrochloric acid (in the case of a trityl) or tetrabutylammonium fluoride (in the case of a silane) to yield compound 25.

2-chloro-2-oxo-1,3,2-dioxaphospholane is then reacted with compound 25 to yield phospholane 26 which readily reacts with trimethylamine to yield the phosphatidylcholine derivative 27. Putting 27 in the presence of phospholipase D and serine allows the exchange of the choline group for the serine group and yields the phosphatidylserine derivative 28 as the major product.

Figure 8:
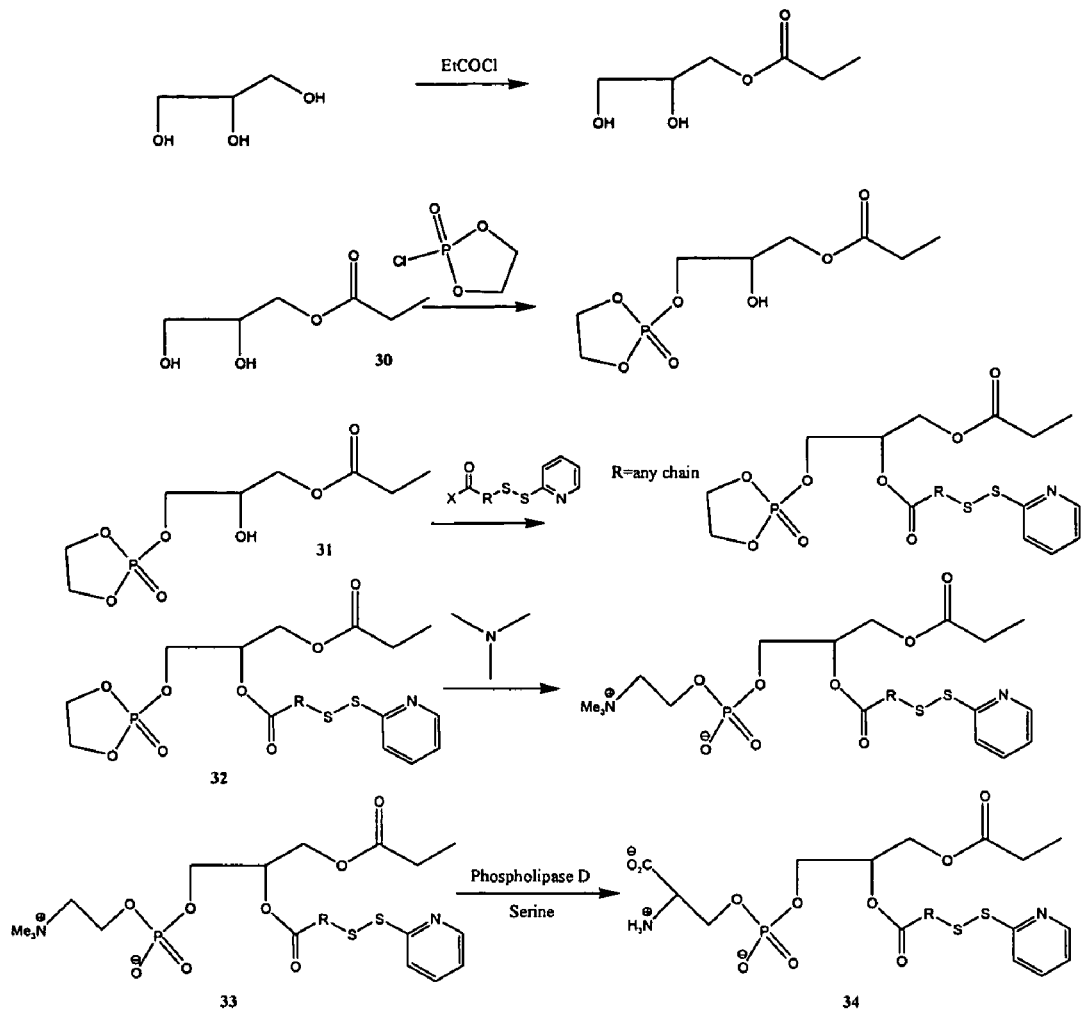
FIG. 8 shows a third synthetic scheme to synthesize a phosphatidylserine derivative that can be easily reacted with thiols.

FIG. 8 presents a third scheme for obtaining a PS derivative that can be easily reacted with thiols. As described above, the final product can be coupled with proteins (or peptides) that have been previously reacted with imidothiolane to functionalize them to display thiols (FIG. 6) (47). As shown in FIG. 8, glycerol is reacted with one equivalent of acetyl chloride to yield monoester 30. 2-chloro-2-oxo-1,3,2-dioxaphospholane is then reacted with the dihydroxyl compound 30 to yield phospholane 31. The secondary hydroxyl of compound 31 is reacted with a linker that contains a thiol-reactive group, such as a reactive disulfide. Again, an activated acid is used to react with the hydroxyl in order to yield an ester. The thiol-reactive acid that is used to react with the secondary hydroxyl can be varied. The R group can be any linker that is conventionally used in bioconjugates. Compound 32 is reacted with trimethylamine to yield the phosphatidylcholine derivative 27. Putting 27 in the presence of phospholipase D and serine allows the exchange of the choline group for the serine group and yields the phosphatidylserine derivative 34 as the major product.

Figure 9:
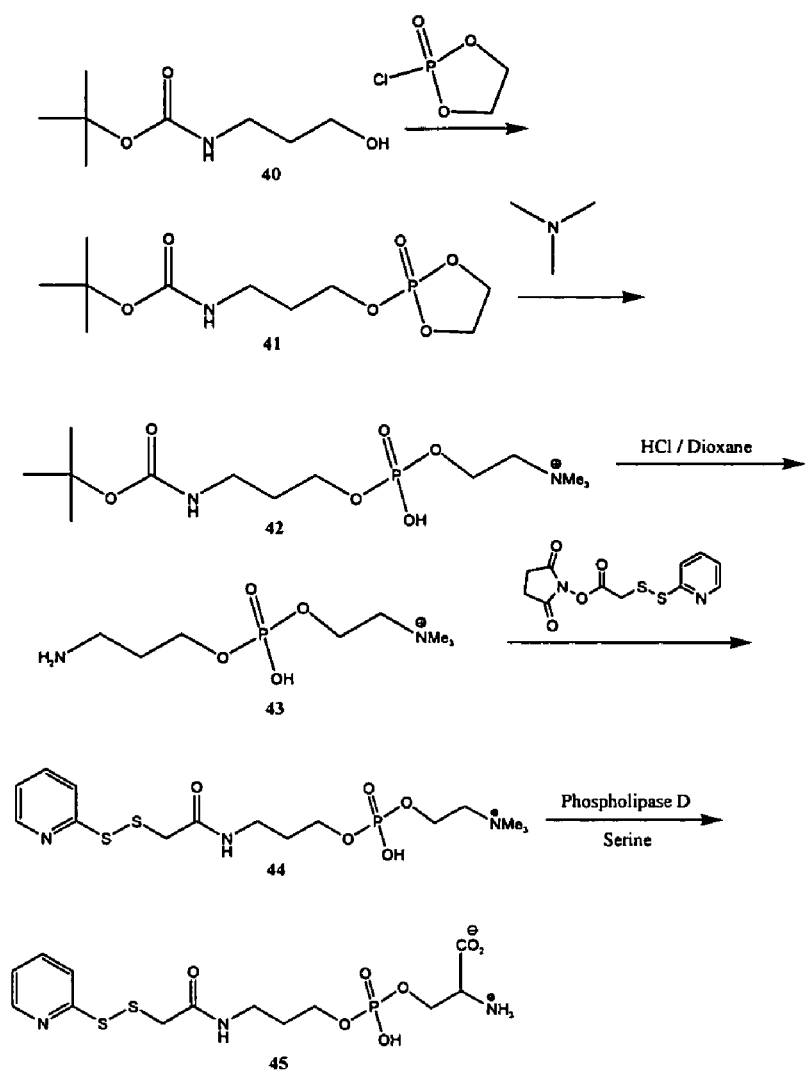
FIG. 9 shows a fourth synthetic scheme to synthesize a phosphatidylserine derivative that can be easily reacted with thiols.

FIG. 9 presents a fourth scheme for obtaining a PS derivative that can be easily reacted with thiols. As described above, the final product can be coupled with proteins (or peptides) that have been previously reacted with imidothiolane to functionalize them to display thiols (FIG. 6) (47). Commercially available BOC-protected hydroxylamine 40 is reacted with 2-chloro-2-oxo-1,3,2-dioxaphospholane in the presence of a base to yield phospholane 41 which readily reacts with trimethylamine to yield the phosphatidylcholine derivative 42. Stirring 42 in a hydrochloric acid solution removes the BOC and yields the free amine 43, which is in turn reacted with a thiol-reactive activated ester in the presence of a base. The resulting phosphatidylcholine derivative 44 is put in the presence of phospholipase D and serine, allowing the exchange of the choline group for the serine group and yielding the phosphatidylserine derivative 45 as the major product.

Figure 10:
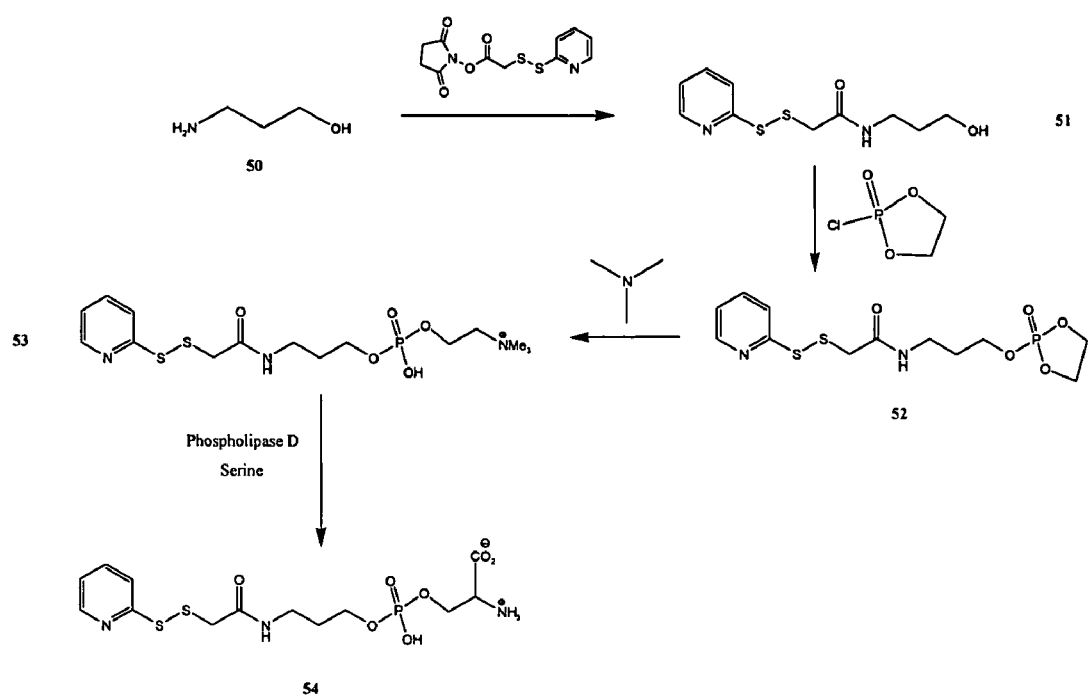
FIG. 10 shows a fifth synthetic scheme to synthesize a phosphatidylserine derivative that can be easily reacted with thiols.

FIG. 10 presents a fifth scheme for obtaining a PS derivative that can be easily reacted with thiols. As described above, the final product can be coupled with proteins (or peptides) that have been previously reacted with imidothiolane to functionalize them to display thiols (FIG. 6).[47] As shown in FIG. 10, commercially available hydroxylamine 50 is reacted with an NHS-activated thiol-reactive disulfide to yield the hydroxyl 51. Compound 51 is reacted with 2-chloro-2-oxo-1,3,2-dioxaphospholane in the presence of a base to yield phospholane 52 which readily reacts with trimethylamine to yield the phosphatidylcholine derivative 53. Stirring 53 in the presence of phospholipase D and serine allows the exchange of the choline group for the serine group and yields the phosphatidylserine derivative 54 as the major product.

Figure 11:
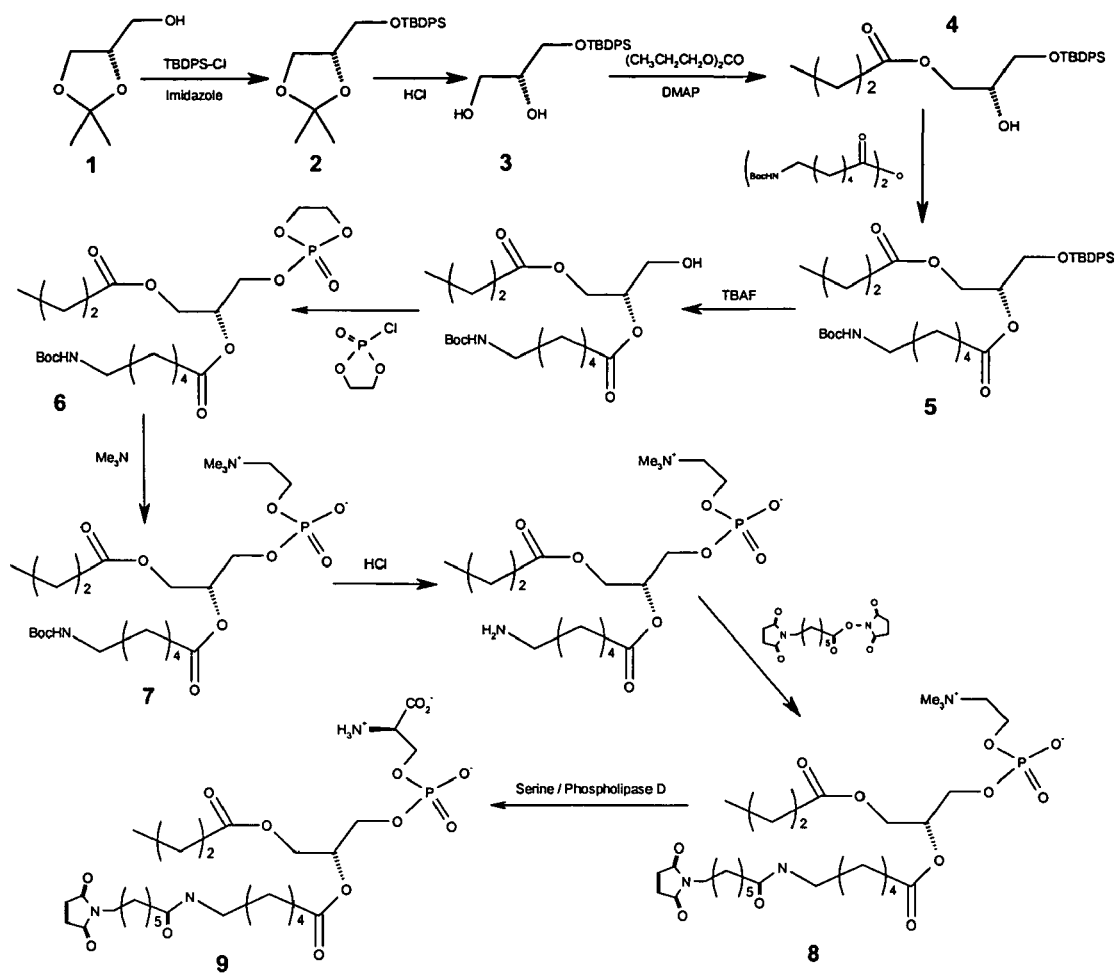
FIG. 11 shows a fifth synthetic scheme to synthesize a phosphatidylserine derivative that can be easily reacted with thiols.

FIG. 11 presents a sixth scheme for obtaining a PS derivative that can be easily reacted with thiols. The PS derivative contains a thiol-reactive maleimide rather than a pyridyl sulfate. Without wishing to be bound by any theory, maleimide-containing PS derivatives are likely to exhibit higher stability under physiological conditions and may thus be preferred for use in the synthesis of the inventive conjugates. Briefly, as shown in FIG. 11, the commercial acetal 1 is protected with a bulky chlorosilane to yield 2. Deprotecting the acetal in acid condition yields the diol 3 and reacting this diol with the anhydride of butyric acid results in 4. The commercially available Boc-protected 6-aminohexanoic acid is converted to its anhydride and reacted with 4 to yield the compound 5. Treating compound 5 with t-butylammonium fluoride (TBAF) removes the silane protecting group and reacting the resulting hydroxyl with 2-chloro-2-oxo-1,3,2-dioxaphospholane yields the compound 6. Reacting 6 with trimethylamine generates compound 7. Compound 7 is deprotected in acidic condition and reacted with a commercial maleimide/NHS-ester bifunctional linker (Pierce) to yield the thiol-reactive phosphatidylcholine derivative 8. This compound may, if desired, be used as a negative control. Phospholipase D and serine are used to convert compound 8 into the desired PS derivative 9, as described above. The thiol-reactive compound 9 is coupled with ligands or antibodies that display, or have been functionalized to display, thiols.

Figure 12:
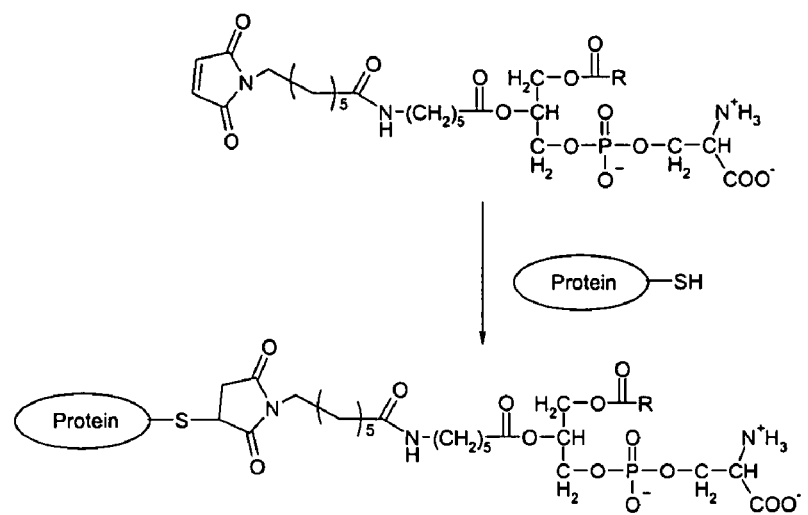
FIG. 12 shows the coupling of a thiol-reactive PS derivative with a protein containing free thiols via a C—S bond.

FIG. 12 shows the coupling of a compound such as 9 with a protein containing free thiols. Note that the coupling is via a C—S bond. In certain embodiments of the invention the PS head group in the molecules of FIG. 12 is attached to the middle C of the glycerol backbone while the maleimide linker moiety is attached to the terminal C at the position occupied by the PS head group in FIG. 12. In other embodiments of the invention the R-containing moiety is attached to the middle C of the glycerol backbone while the maleimide linker moiety is attached to the terminal C at the position occupied by the R-containing moiety in FIG. 12.

Maleimide-containing linkers can be used instead of the disulfide containing linker depicted in the schemes shown in FIGS. 6-10 to generate PS derivatives containing a maleimide group. Other linkers such as iodoacetamide could also be used. Linkers containing carboxylic acid- and/or amine-reactive groups are also usable, but it may be necessary to protect such groups on the serine to prevent them from reacting when the PS derivative is linked to the antibody or ligand. The schemes presented above describe generating a free —SH on the cell binding moiety (e.g., antibody) and coupling it with a thiol-reactive group on a PS derivative. However, one of ordinary skill in the art will recognize that it is also possible to generate a free —SH on the PS derivative, add a thiol-reactive group to the antibody or ligand (e.g., by using an amine-reactive/thiol-reactive bifunctional linker that will react with free lysines at the surface of the moiety), and couple both together. For example, maleimide-activated antibodies or ligands can be coupled with free —SH groups on a PS derivative (see FIG. 2C).

Furthermore, if a protecting group is added to the free amine or the free acid on the serine residue of a PS derivative, an amine-reactive group on the PS derivative could then be used to attach it to an antibody or ligand, and then the protective group is removed to restore the unprotected serine.

In certain embodiments of the invention multiple phagocytic markers, which can be the same or different, are linked to a single cell-binding moiety. For example, it may be desirable to incorporate phagocytic markers that are recognized by two different cell surface receptors on phagocytes into the same molecule.

The invention thus provides a variety of compounds comprising a PS head group or other group derived from PS comprising a PS head group.

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; — or -GR$^{G1}$ wherein G is —O—, —S—, —NR$^{G2}$—, —C(=O)—, —S(=O)—, —SO$_2$—, —C(=O)O—, C(=O)NR$^{G2}$—, —OC(=O)—, NR$^{G2}$C(=O)—, —OC(=O)O—, —OC(=O)NR$^{G2}$—, NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, OC(=NR$^{G2}$), —NR$^{G2}$C(=NR$^{G3}$)—, —NR$^{G2}$ SO$_2$—, —NR$^{G2}$ SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown and/or described herein.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; — or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^2$C(=O)—, —OC(=O)O—, —OC(=O)NR$^{G2}$—, —NR$^{G2}$C(=O)O—, NR$^{G2}$C(=O)NR$^{G2}$—, —C(=S)—, —C(=S)S—, —SC(=S)—, —SC(=S)S—, C(=NR$^{G2}$)—, C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$ SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples or generally applicable substituents are illustrated by the specific embodiments shown in the Examples, which are described herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown and/or described herein.

In general, the term "aromatic moiety", as used herein, refers to stable substituted or unsubstituted unsaturated mono- or polycyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, -(alkyl)aromatic, -(heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Substituents for aryl and heteroaryl moieties include, but are not limited to, any of the previously mentioned substitutents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; — or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown and/or described herein.

The terms "alkoxy" (or "alkyloxy"), and "thioalkyl" as used herein refers to an alkyl group, as previously defined, attached to the parent molecular moiety through an oxygen atom ("alkoxy") or through a sulfur atom ("thioalkyl"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy. Examples of thioalkyl groups include, but are not limited to, methylthio, ethylthio, propylthio, isopropylthio, n-butylthio, and the like.

The term "amine" refers to a group having the structure —N(R)$_2$ wherein each occurrence of R is independently hydrogen, or an aliphatic, heteroaliphatic, aromatic or heteroaromatic moiety, or the R groups, taken together, may form a heterocyclic moiety.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

The terms "halo" and "halogen" as used herein refer to an atom selected from fluorine, chlorine, bromine and iodine.

The term "halogenated" denotes a moiety having one, two, or three halogen atoms attached thereto.

The term "haloalkyl" denotes an alkyl group, as defined above, having one, two, or three halogen atoms attached thereto and is exemplified by such groups as chloromethyl, bromoethyl, trifluoromethyl, and the like.

The term "acyloxy", as used herein, does not substantially differ from the common meaning of this term in the art, and refers to a moiety of structure —OC(O)R$_X$, wherein R$_X$ is a substituted or unsubstituted aliphatic, alicyclic, heteroaliphatic, heteroalicyclic, aryl or heteroaryl moiety.

The term "acyl", as used herein, does not substantially differ from the common meaning of this term in the art, and refers to a moiety of structure —C(O)R$_X$, wherein R$_X$ is a substituted or unsubstituted, aliphatic, alicyclic, heteroaliphatic, heteroalicyclic, aryl or heteroaryl moiety.

The term "imino", as used herein, does not substantially differ from the common meaning of this term in the art, and refers to a moiety of structure —C(=NR$_X$)R$_Y$, wherein R$_X$ is hydrogen or an optionally substituted aliphatic, alicyclic, heteroaliphatic, heteroalicyclic, aryl or heteroaryl moiety; and R$_Y$ is an optionally substituted aliphatic, alicyclic, heteroaliphatic, heteroalicyclic, aryl or heteroaryl moiety.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

Some examples of substituents of the above-described aliphatic (and other) moieties of compounds of the invention include, but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; — or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —C(=NR$^{G2}$)—, —NR$^{G2}$C(=NR$^{G3}$)—, —NR$^{G2}$SO$_2$—, —NR$^{12}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown and/or described herein.

A representative subset of the moities that can be present either as part of the chain or as a substituent is listed here: the chain or substituent can consist of or contain azole, azide, imine, imide, maleimide, iodoacetamide, amide, carbamide, amine, cyano, urethane, isocyanate, lactone, lactam, oxazoline, oxazole, oxaziazole, oxazinone, isoimide, nitro, diazo, imino ester, pyridyl, aniline, quinine, quinone, imine, acyl halide, quinoxaline, sulfamide, ketone, aldehyde, imidazole, carbonate, epoxide, peroxide, alkene, alkyne, carboxylic acid, anhydride, ester, acyl (carbonyl), hydroxyl, phenol, aromatic, halogenated, silazane, hydrazide, azo, azoxy, thioether, thioester, triazine, triazole, thiazole, silane, or siloxane groups.

In general, the invention provides a compound having the following formula:

A-L-PSG wherein A is an antibody or ligand that binds to a cellular marker, L is a linker consisting of an aliphatic, alicyclic, heteroaliphatic, heteroalicyclic, aromatic, heteroaromatic moiety, and PSG is a group derived from phosphatidylserine. In certain preferred embodiments of the invention L is a heteroaliphatic or heteroalicyclic moiety. In certain preferred embodiments of the invention L is any of the linkers mentioned above. For example, in certain preferred embodiments of the invention L, before being used to link an antibody or ligand to a PS head group derivative, comprises or consists of a succinimidyl ester, maleimide, pyridyldisulfide, or iodoacetamide linker. As will be appreciated by one of ordinary sill in the art, following linkage, the structure of the linker is modified by virtue of the formation of the covalent bonds to A and/or to another atom to which the linker is covalently joined at its other end in the case of bifunctional linkers. Such modified linkers are still considered to be linkers of the particular types recited herein, notwithstanding the fact that their functional groups have reacted and have changed as a result. In certain embodiments, after reacting the linker to link an antibody or ligand to a PS head group derivative, L comprises or consists of an amide, a disulfide, a succinimide, an acetamide, or a thioether. In certain preferred embodiments of the invention A and L in any of the formulas above or below are covalently linked via an S—S bond. In other preferred embodiments of the invention A and L are covalently linked via an S—C bond. In certain embodiments L, or a substituent thereof, in any of the formulas above or below, comprises or consists of a metal atom or metal cluster.

In certain preferred embodiments of the invention PSG has one of the formulas below, in which X=C, O, N, or S; and Y=O or S; and R is hydrogen or an aliphatic, alicyclic, heteroaliphatic, heteroalicyclic, aromatic, heteroaromatic moiety:

Formula 1
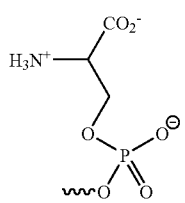
Formula 2
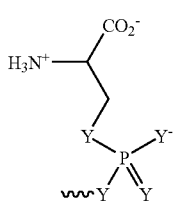
X = C, O, N, or S
Y = O or S
Formula 3
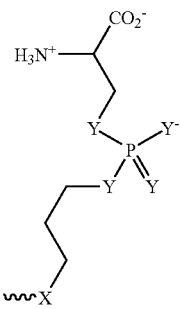
X = C, O, N, or S
Y = O or S
Formula 4
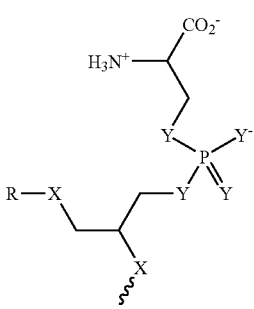
X = C, O, N, or S
Y = O or S
Formula 5
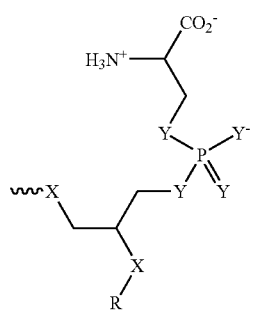
X = C, O, N, or S
Y = O or S
Formula 6
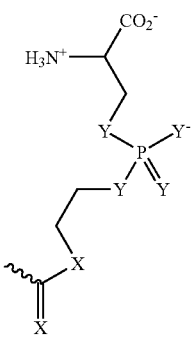
X = C, O, N, or S
Y = O or S
Formula 7
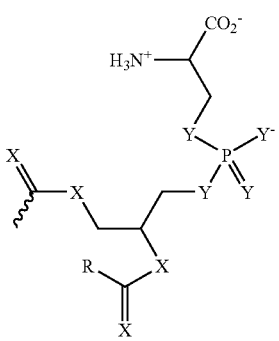
X = C, O, N, or S
Y = O or S
Formula 8
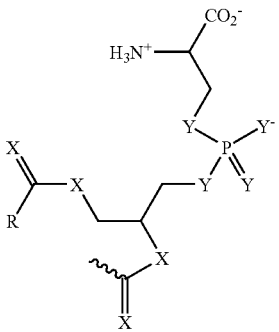
X = C, O, N, or S
Y = O or S
Formula 9
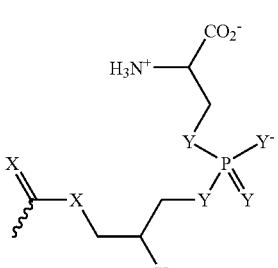
X = C, O, N, or S
Y = O or S -continued Formula 10

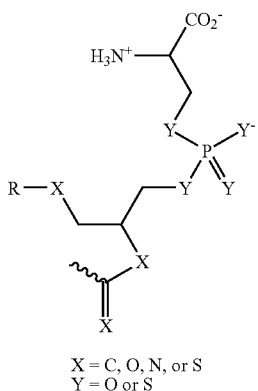

X = C, O, N, or S
Y = O or S

Formula 11

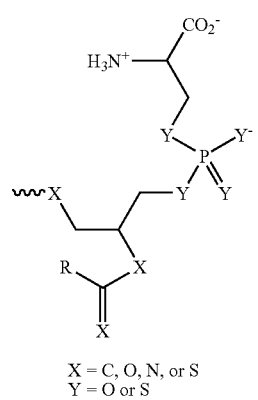

X = C, O, N, or S
Y = O or S

Formula 12

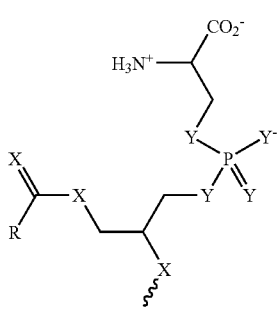

X = C, O, N, or S
Y = O or S

In the structures shown above, Y=O in certain preferred embodiments of the invention. In certain preferred embodiments of the invention R is a saturated or unsaturated, substituted or unsubstituted, aliphatic or heteroaliphatic chain having a length of between 1 and 20 carbon atoms, between 1 and 10 carbon atoms, between 1 and 6 carbon atoms, e.g., 2, 3, 4, or 5 carbon atoms. In certain preferred embodiments of the invention R is a saturated or unsaturated, substituted or unsubstituted, aliphatic chain having a length of between 1 and 20 carbon atoms, between 1 and 10 carbon atoms, between 1 and 6 carbon atoms, e.g., 2, 3, 4, or 5 carbon atoms. The wavy line in formulas 1-12 represents a point of attachment to L. In certain embodiments of the invention L is absent, in which case the wavy line represents a point of attachment to A.

The invention further provides compounds having the following formula:

Formula 13

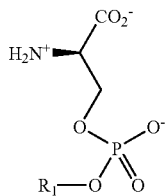

wherein $R_1$ comprises or consists of either an antibody or ligand or has the structure A-L wherein A is an antibody or ligand and wherein L is a linker consisting of an aliphatic, alicyclic, heteroaliphatic, heteroalicyclic, aromatic, heteroaromatic moiety.

The invention further provides compounds having the following formula:

Formula 14

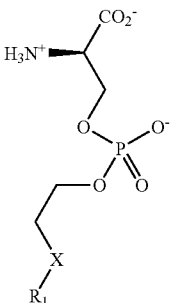

wherein $R_1$ comprises or consists of either an antibody or ligand or has the structure A-L wherein A is an antibody or ligand, and wherein L is a linker consisting of an aliphatic, alicyclic, heteroaliphatic, heteroalicyclic, aromatic, heteroaromatic moiety, and wherein X is selected from the group consisting of O, N, and S. In certain preferred embodiments of the invention X is O.

The invention further provides compounds having the following formula:

Formula 15

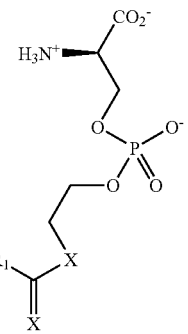

wherein $R_1$ comprises or consists of either an antibody or ligand or has the structure A-L wherein A is an antibody or ligand, and wherein L is a linker consisting of an aliphatic, alicyclic, heteroaliphatic, heteroalicyclic, aromatic, heteroaromatic moiety, and wherein each X is independently selected from the group consisting of O, N, and S. In certain preferred embodiments of the invention at least one instance of X is O.

The invention further provides compounds having the following formula:

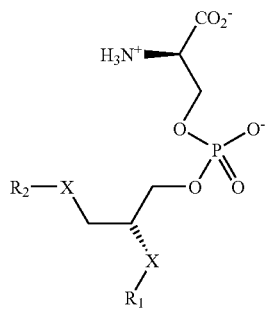

Formula 16 wherein (i) one of $R_1$ or $R_2$ comprises or consists of either an antibody or ligand or a moiety having the structure A-L wherein A is an antibody or ligand, and wherein L is a linker consisting of an aliphatic, alicyclic, heteroaliphatic, heteroalicyclic, aromatic, heteroaromatic moiety; the other of $R_1$ or $R_2$ is either hydrogen or an aliphatic, alicyclic, heteroaliphatic, heteroalicyclic, aromatic, heteroaromatic moiety; and wherein (ii) each X is independently selected from the group consisting of O, N, and S. In certain preferred embodiments of the invention whichever of $R_1$ and $R_2$ does not comprise an antibody or ligand comprises or consists of a saturated or unsaturated, substituted or unsubstitued aliphaic chain having a length of between 1 and 20, between 1 and 10, between 1 and 6, or 5 or less carbon atoms, where length refers to the number of C atoms in the main (longest) chain. In certain preferred embodiments of the invention at least one instance of X is O.

The invention further provides compounds having the following formula:

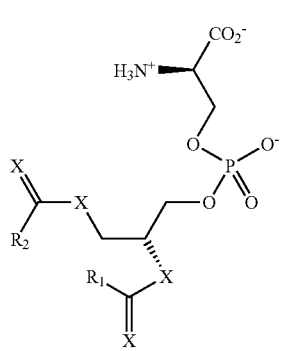

Formula 17 wherein (i) one of $R_1$ or $R_2$ comprises or consists of either an antibody or ligand or a moiety having the structure A-L wherein A is an antibody or ligand, and wherein L is a linker consisting of an aliphatic, alicyclic, heteroaliphatic, heteroalicyclic, aromatic, heteroaromatic moiety; the other of $R_1$ or $R_2$ is either hydrogen or an aliphatic, alicyclic, heteroaliphatic, heteroalicyclic, aromatic, heteroaromatic moiety; and wherein (ii) each X is independently selected from the group consisting of O, N, and S. In certain preferred embodiments of the invention whichever of $R_1$ and $R_2$ does not comprise an antibody or ligand comprises or consists of a saturated or unsaturated aliphatic or heteroaliphatic chain having between 1 and 20, between 1 and 10, between 1 and 6, e.g., 2, 3, 4, or 5 carbon atoms. In certain preferred embodiments of the invention whichever of $R_1$ and $R_2$ does not comprise an antibody or ligand comprises or consists of a saturated or unsaturated aliphatic chain having between 1 and 20, between 1 and 10, between 1 and 6, e.g., 2, 3, 4, or 5 carbon atoms. In certain preferred embodiments of the invention at least one instance of X is O.

With respect to any of the compounds described above, in preferred embodiments of the invention L is selected from the linkers mentioned elsewhere herein, including succinimidyl ester, maleimide, pyridyldisulfide, or iodoacetamide linkers, or linkers having similar functional groups for mediating covalent linkage. In preferred embodiments of the invention A is an antibody or ligand that binds to a cellular marker, e.g., a cell type specific marker. In certain embodiments of the invention A is an antibody or ligand that binds to one of the cellular markers mentioned herein.

The invention further provides compounds in which one or more of the $CH_2$ moieties other than the $CH_2$ moiety in the PS head group is either absent or is independently replaced by an aliphatic, alicyclic, heteroaliphatic, heteroalicyclic, aromatic, heteroaromatic moiety. In certain embodiments of the invention the moiety is a substituted or unsubstituted aliphatic or heteroaliphatic chain containing between 1 and 6 carbon atoms or between 1 and 4 carbon atoms. The invention further provides compounds in which one or more of the $CH_2$ moieties other than the $CH_2$ moiety in the PS head group is either absent or is independently replaced by an unsaturated chain such as —CH=CH—, —$CH_2$—CH=CH—, a cyclic structure, an aromatic ring, an ether (—$CH_2$—O—$CH_2$—), amide (—CO—$NH_2$—), ester (—CO—O—), imine (—C=N—), thioether (—C—S—C—), or oligo(ethylene glycol) group (—O—$CH_2$—$CH_2$—)$_n$. In those compounds that contain both $R_1$ and $R_2$, whichever of $R_1$ or $R_2$ does not comprise an antibody or ligand may comprise one or more sulfate (—$SO_3H$) groups and/or may comprise one or many oligo or poly(ethyeleneglycol) chains.

As mentioned above, in certain embodiments of the invention a phagocytic marker other than PS or a group derived from PS is attached to cells to make them appear apoptotic. For example, MFG-E8, protein S, annexin I, β2-glycoprotein, or GAS-6 can be used. A variety of methods can be employed to make a bifunctional conjugate linked to one of these phagocytic markers and to a moiety (e.g., an antibody or ligand) that binds to the cell surface. For example, if the phagocytic marker is a protein or peptide, the conjugate may be made by recombinant DNA techniques, as a fusion protein comprising an antibody (e.g., a single chain antibody) or ligand portion (if the ligand is a protein or peptide) and a phagocytic marker portion. According to this approach, a nucleic acid construct encoding both the antibody or ligand portion and the phagocytic marker portion is constructed. The nucleic acids encoding an antibody chain, ligand, and phagocytic marker are obtained from any suitable source (e.g., by cloning from a cDNA library, by PCR amplification using appropriate primers, etc.) or can be chemically synthesized if the sequence is available, as is the case for many of the ligands mentioned herein. The nucleic acids are inserted in frame into an expression vector, of which many are available for expression systems utilizing various cell types (e.g., bacterial cells, yeast or other fungal cells, insect cells, mammalian cells). The expression vector is introduced into cells of the appropriate type (e.g., by electroporation, transformation, transfection, etc.), and cells are maintained under conditions in which the fusion protein is expressed. It may be preferable to use a eukaryotic host cell (e.g., insect, human) so that post-translational processing events characteristic of eukaryotic cells take place.

Example 2 provides a detailed example of this approach, describing the creation of a fusion protein comprising a phagocytic marker (MFG-E8) and a streptavidin domain. (While streptavidin is not itself a preferred cell-binding moiety, the same methods can be used to create fusion proteins between MGF-E8 and cell-binding moieties such as an antibody chain that binds to an integrin, a ligand such as angiostatin, etc.) The fusion protein is then purified using standard methods.

A number of variations are possible. For example, a nucleic acid portion that encodes a signal sequence can be included in the open reading frame in the expression vector so that the fusion protein is secreted into the media. A tag (e.g., an HA tag, 6xHis tag, FLAG tag, GST tag, etc.) can be included in the open reading frame to facilitate purification of the protein. The nucleic acid sequences can be codon-optimized for optimal expression in the relevant cell type.

Rather than generating a fusion protein or conjugate in which the cell-binding moiety and phagocytic marker are covalently linked, in certain embodiments of the invention a noncovalent interaction is used to create bifunctional molecule. For example, the biotin-streptavidin system can be used. According to this approach, biotin is attached to either the cell binding moiety or the phagocytic marker, and avidin is attached to the other. The biotinylated and avidin-functionalized molecules are contacted with each other to allow binding to take place. Methods for biotinylating proteins or other molecules are well known in the art and kits for doing so are commercially available.

Avidin can be attached to a cell binding moiety or phagocytic marker using various approaches. For example, a fusion protein comprising avidin and a cell-binding moiety or phagocytic marker can be constructed as described above and in Example 2. Alternately, avidin can be linked to the cell-binding moiety or phagocytic moiety using a variety of the linkage strategies described herein. Use of the biotin-avidin system allows for modularity in that a single avidin-containing fusion protein comprising either a cell-binding moiety or phagocytic marker can be used to form conjugates with numerous different biotinylated partners (phagocytic markers or cell-binding moieties, respectively), without the need to individually synthesize the complete conjugate molecule. This allows for easy retargeting of the molecules toward different cell surface receptors by using a different biotinylated ligand (e.g., an antibody or another cell-binding protein, peptide, or small molecule).

Figure 14:
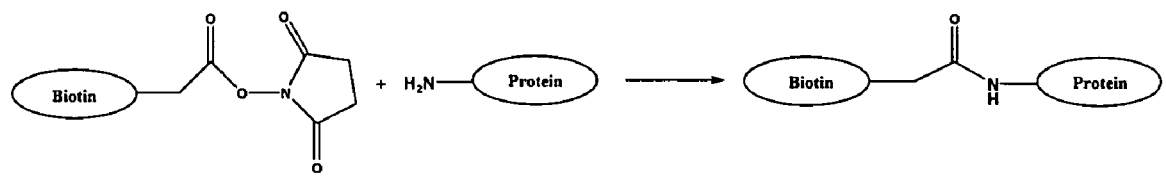
FIG. 14 shows coupling of NHS-functionalized biotin to the surface lysines of a protein.
Figure 15:
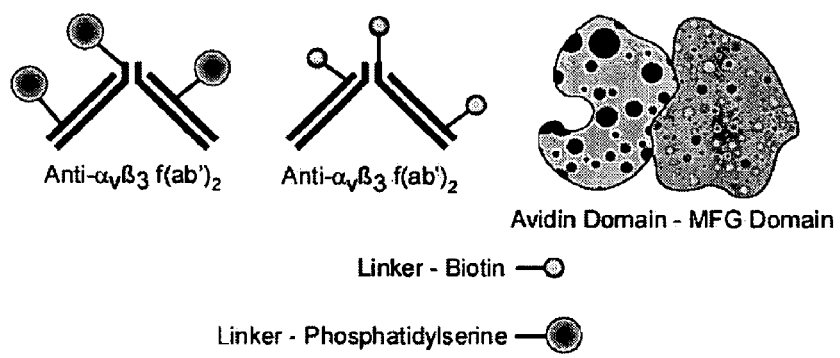
FIG. 15 shows a molecule in which a PS derivative is linked to an F(ab')$_2$ antibody fragment that specifically binds to integrin alpha(v)beta(3) (left); a conjugate in which biotin is linked to an F(ab')$_2$ antibody fragment that specifically binds to integrin alpha(v)beta(3) (middle); and a representation of a molecule comprising an avidin domain and an MFG-E8 domain (right).

The coupling of biotin to proteins can be readily accomplished, e.g., by reacting a commercially available NHS-functionalized biotin derivative. For example, the NHS ester of 15-([biotinoyl]amino)-4,7,10,13-tetraoxapentadecanoic acid (FIG. 13) can be purchased from Pierce and reacted directly with lysines at the surface of a target protein in a slightly basic buffer (pH 7-9) to form a stable amide bond (FIG. 14), following the standard protocol provided by the supplier. FIG. 15 shows a molecule in which biotin is linked to an F(ab')$_2$ antibody fragment that specifically binds to integrin alpha(v)beta(3) (middle); and a representation of a molecule comprising an avidin domain and an MFG-E8 domain (right). Any cellular marker could be used instead of integrin alpha(v)beta(3), and any phagocytic marker could be used instead of MFG-E8.

The biotin-linked molecule and the avidin-linked molecule can be incubated together to allow biotin-avidin binding to occur. The resulting conjugate can be administered to a subject for treatment of the various diseases mentioned herein or can be used for the in vitro applications described below. Alternately, the two molecules can be administered or used without pre-incubation. For example, a first molecule in which biotin is linked to a cell type specific marker can be administered to a subject or added to a cell-containing preparation in vitro. The molecule binds to the surface of target cells. A second molecule in which avidin is linked to a phagocytic marker can then be administered to the subject or added to the cell-containing preparation. The avidin-containing molecule binds to the biotin-containing molecule, thus generating a conjugate much as would have occurred if the two molecules had been pre-incubated. The molecules can be administered to a subject or added to a cell-containing preparation in either order, and the times of administration or addition can be separated by a period of time. Thus the invention provides a set of molecules comprising (a) a molecule comprising a moiety that binds to a cellular marker present on or at the surface of a target cell, wherein the moiety is linked to a first binding partner; and (b) phagocytic marker linked to a second binding partner, wherein the first and second binding partners bind to one another. The set of molecules may be delivered to cells or to a subject simultaneously or separated by an interval of time, following which they associate either after or before the cell binding moiety binds to a target cell.

Another method of producing a conjugate comprising a cell-binding domain and a phagocytic marker is to use a bifunctional molecule that comprises two different ligand or binding domains, one of which binds to a cellular marker and the other of which binds to the phagocytic marker. Alternately, a molecule that comprises one domain that binds to a marker on the target cell and one domain that binds to a marker on phagocytic cells can be used. For example, bifunctional antibodies comprising two different binding domains could be used.

Reagents used to crosslink liposomes and potentially other lipid assemblies to biomolecules such as antibodies or ligands that bind to cellular markers typically comprise a phospholipid derivative to anchor one end of the crosslink in the lipid layer and a reactive group at the other end to attach the membrane assembly to the target biomolecule. Regardless of how the compositions of the invention are prepared, in certain embodiments of the invention it is preferable to purify or isolate the antibody or ligand with the attached phagocytic marker from other molecules that may be present, e.g., prior to administration to a subject. References mentioned above provide further details regarding liposomes and methods of incorporating cell-targeting moieties into them.

It is noted that the foregoing descriptions represents only some examples of techniques that can be employed to synthesize the compositions of the invention.

Applications

The compositions of the invention can be administered to a subject to treat a wide variety of other diseases and clinical conditions, many of which are mentioned above. For example, the compositions may be used for treatment of diseases and clinical conditions, that result at least in part from and/or are characterized by excessive or abnormal angiogenesis such as macular degeneration, diabetic retinopathy, retinopathy of prematurity, persistent hyperplastic vitreous syndrome, choroidal neovascularization, psoriasis, arthritis, osteomyelitis, synovitis, osteophyte formation, obesity, warts, allergic dermatitis, asthma, polyps, atherosclerosis, hemangiomas, vascular malformations, DiGeorge syndrome, hereditary hemorrhagic telangiectasia, transplant arteriopathy, warts, scar keloids, pyogenic granulomas, blistering disease, Kaposi sarcoma (e.g., in AIDS patients), primary pulmonary hypertension, inflammatory bowel disease, periodontal disease, ascites, peritoneal adhesions, endometriosis, uterine bleeding, ovarian cysts and hyperstimulation, various additional autoimmune diseases, etc. In various embodiments of the invention the cancer may be, but is not limited to, cancer of the biliary tract, bladder, bone, breast, brain, cervix, colon, endometrium, esophagus, head and neck, kidney, liver, lung, oral cavity, ovary, pancreas, prostate, rectum, skin, testis, thyroid, or uterus. In various embodiments of the invention the cancer may be a leukemia, lymphoma, multiple myeloma, choriocarcinoma, etc.

Other diseases or clinical conditions that can be treated using the compositions and methods of the invention include osteoporosis, osteopenia, fibrosis, vascular stenosis, organ rejection following transplant, and a wide variety of infections, particularly infections by viruses, intracellular bacteria or parasites. The compositions and methods of the invention can also be used for contraceptive purposes, e.g., by targeting a phagocytic marker to sperm cells using a marker that is expressed on or at the sperm cell surface. The composition can be delivered systemically or locally. In mammals, gamete recognition and sperm binding to the oocyte are mediated by the zona pellucida (ZP), an acellular coat surrounding the plasma membrane of the oocyte that consists of particular ZP proteins, for example ZP2 (139). Monoclonal antibodies against ZP2 peptides exist that can be used as a specific marker for ZP2 and can be used to target compositions of the invention to sperm cells to enhance their phagocytosis.

The compositions and methods of the invention find particular use in the treatment of tumors (benign or malignant), cancers of the hematopoietic system such as leukemias and myeloproliferative or myelodysplastic disorders, polycythemia, etc.). As discussed above, in certain preferred embodiments of the invention the compositions inhibit angiogenesis or destroy existing vasculature by enhancing phagocytosis of endothelial cells or precursors thereof, e.g., endothelial cells or precursors thereof associated with tumor vasculature. Since blood vessels are typically necessary for tumor survival and, in particular, new blood vessels are typically necessary for tumor growth, this strategy effectively inhibits tumor enlargement and/or the survival of existing tumor cells or prevent the development of tumors. Tumor cells can be targeted directly and by tagging them with phagocytic markers via binding to tumor markers.

A number of approaches towards inhibiting angiogenesis exist and more are being explored. More than 20 companies have anti-angiogenic drugs in various stages of clinical trials (more than 60 drugs are being tested), and the first clinical results have recently started to emerge. Notably, Genentech demonstrated that its experimental drug Avastin®, also referred to as bevacizumab, could prolong median survival in patients with metastatic colorectal cancer from 15.6 to 18.3 months (59, 60). Avastin is a recombinant monoclonal antibody that binds to VEGF, thereby preventing it from binding to its receptor.

A variety of other anti-angiogenic monoclonal antibodies or inhibitory small molecules that bind to various receptors present on endothelial cells exist (117). The receptors include EGF/HER receptor family members, VEGF receptor family members, PDGF receptor family members, and the ERBB-2/HER-2/neu protein. Antibodies or small molecules that act as antagonists at these receptors include (i) ZD1839 (Iressa®); ZD6474; OS1774 (Tarceva®, also called erlotinib); CI1033; PKI1666; IMC224 (Erbitux), which bind to EGF/HER receptors (118); (ii) PTK787; ZD6474; SU6668; and SU11248, which bind to VEGF receptors (119, 120); (iii) PTK787 and SU11248, which bind to PDGF receptors (119), and (iv) Herceptin®, which binds to the ERBB2/HER-2/neu receptor tyrosine kinase (121, 122). A number of these molecules bind to multiple members of one receptor family or to members of multiple receptor families. In general, anti-angiogenic molecules that target any of the afore-mentioned receptors or their endogenous ligands interfere with signaling pathways that trigger or enhance proliferation of endothelial cells or precursors thereof.

Additional anti-angiogenesis molecules include combretastatin, which targets microtubules (123), and thrombospondin, which blocks endothelial cell migration and neovascularization in the cornea (124). In addition, interferon alpha exerts anti-angiogenic effects, possibly due to the fact that it down-regulates expression of the pro-angiogenic molecule bFGF by cancer cells. Other anti-angiogenic molecules include thalidomide and its anti-angiogenic derivatives such as iMiDs (61, 62) and non-steroidal anti-inflammatory drugs such as aspirin and cyclooxygenase inhibitors, particularly selective inhibitors of cyclooxygenase-2 (63). The fumagillin derivative TNP-470 exhibits potent anti-angiogenic effects, as have a number of other fumagillin analogs (104). Various curcuminoids have also been shown to have anti-angiogenic and anti-cancer properties (105). NM-3, a small molecule isocoumarin, is a recently discovered angiogenesis inhibitor (116).

The present invention encompasses the recognition that administering multiple anti-angiogenic agents concurrently or sequentially may prove more effective than administering a single agent. While not wishing to be bound by any theory, this is particularly likely to be the case when the agents work by different mechanisms, e.g., when one of the agents interferes with a signaling pathway and one of the agents enhances phagocytosis of endothelial cells or precursors thereof. The invention therefore provides a method of treating or preventing a disease or condition associated with excessive or inappropriate vascularization or angiogenesis to a subject in need thereof comprising: administering to the subject concurrently or sequentially (i) an effective amount of a first agent that increases the level or density of a phagocytic marker on or at an endothelial cell surface; and (ii) an effective amount of a second agent, wherein the second agent inhibits angiogenesis by a mechanism other than enhancing phagocytosis. For example, the second agent may inhibit angiogenesis by interfering with a signaling pathway whose activation would otherwise result in cell proliferation.

In certain embodiments of the invention the first agent comprises a moiety (e.g., antibody or ligand) that binds to a cellular marker, wherein a molecule that is a phagocytic marker is linked to the moiety. The second agent may be selected from the group consisting of: antibodies or small molecules that bind to VEGF receptor family members or their endogenous ligand(s), PDGF receptor family members or their endogenous ligand(s), EGF/HER receptor family members or their endogenous ligand(s), and HER2/neu receptors or their endogenous ligands. Any of the specific anti-angiogenic molecules mentioned above may be used. The diseases include tumors and other diseases mentioned above. Multiple anti-angiogenic agents can be used. For example, therapeutic cocktails comprising one or more of the inventive conjugates and at least 1, 2, 3, or more other anti-angiogenic agents may be administered to a subject.

It will be appreciated that in certain embodiments of the invention the moiety that binds to a cellular marker may itself have anti-angiogenic activity. For example, as mentioned above, angiostatin, tumstatin, or other anti-angiogenic polypeptides, can be used as ligands to target a phagocytic marker to endothelial cells. In this case the composition of the invention may inhibit angiogenesis both by interfering with a signaling pathway in endothelial cells and by enhancing phagocytosis of endothelial cells to which it binds. Similarly, antibodies that have anti-angiogenic activity can be used to target a phagocytic marker to endothelial cells. For example, as mentioned above, a variety of antibodies that bind to VEGF, PDGF, EGF, or ERBB-2 receptors and inhibit angiogenesis are available. These antibodies, or antigen-binding fragments thereof, can be used in a composition of the invention to target a phagocytic marker to an endothelial cell, in which case the composition may inhibit angiogenesis by both interfering with a signaling pathway and enhancing phagocytosis.

The compositions of the invention may be given in conjunction with standard chemotherapeutic agents (e.g., alkylating agents; nitrosorureas; antimetabolites (structural analogs of compounds important in cellular metabolism), e.g., methotrexate, purine or pyrimidine analogs; plant alkaloids such as vinblastine, vincristine, podophyllotoxins, camptothecins, and taxanes; antibiotics (compounds originally isolated from microorganisms) such as anthracyclines, mitomycin, bleomycin, asparaginase; hormonal agents such as estrogen and/or androgen inhibitors (e.g., tamoxifen) and aromatase inhibitors; hydroxyurea; etc. The compositions may also be given in conjunction with agents of more recently developed classes such as kinase inhibitors, farnesyltransferase inhibitors, other oncogene or cell cycle inhibitors, etc., and/or in conjunction with immunotherapy (e.g., administration of an interferon or interleukin) or radiotherapy. See *Goodman and Gilman's The Pharmacological Basis of Therapeutics, Basic and Clinical Pharmacology, or Cancer: Principles and Practice of Oncology* for further details. These other therapies may be administered concurrently, sequentially, as part of a defined treatment protocol, etc. Standard chemotherapeutic agents and radiotherapy may exert antitumor effects by a variety of mechanisms including both directly killing tumor cells and, in some cases, also by inhibiting angiogenesis (125, 126).

In addition to in vivo therapeutic applications, the compositions of the invention have a number of in vitro uses. It is often desirable to obtain cell populations that are relatively homogeneous in terms of their cell type composition, (e.g., populations that contain only or substantially only a single cell type) for any of a variety of purposes. For example, it is often of interest to administer a compound to a subject, harvest cells or tissue from the subject, and examine the effect of a compound on gene expression in a particular cell type of interest, proliferation of a cell type of interest, toxicity to a cell type of interest, or any other detectable cell phenotype, or simply to determine whether the compound entered or bound to a cell type of interest. However, when tissue samples are harvested from a subject they typically contain a plurality of cell types, and it can be difficult to distinguish effects on the cell type of interest from effects on other cell types.

The compositions of the invention can be used to eliminate or reduce the number of one or more cell types in a cell population, and thus to prepare a more purified cell population from a sample containing multiple cell types (e.g., a tissue sample or other sample containing a plurality of cell types), by (i) contacting the sample with a composition of the invention comprising a moiety that binds to a cellular marker, wherein a molecule that is a phagocytic marker is linked to the moiety; (ii) contacting the sample with phagocytes following the step of contacting with a composition of the invention; and (iii) maintaining the sample in the presence of phagocytes to allow phagocytosis to occur. The cellular marker is preferably a cell type specific marker that is expressed on the surface of cells that are not desired in the purified cell population. Multiple compositions, each with a different cellular marker, can be used to eliminate multiple different cell types from the composition.

If desired, the phagocytes can then be removed by any of a number of methods. For example, if the phagocytes are non-adherent while the cell type of interest is adherent, the phagocytes can simply be washed away. Alternately, antibodies to a phagocyte-specific marker that is not found on the cell type of interest can be coupled to magnetic beads, which are then incubated with the sample after phagocytosis has occurred. The phagocytes bind to the beads via the antibody and can then be easily removed using a magnetic field. Other methods can also be used, and furthermore it may not be necessary to remove the phagocytes as they may be readily distinguishable from the cell type of interest or may not be deleterious if administered to a subject.

In general, any cell type capable of performing phagocytosis, e.g., macrophages and various monocytic cells, can be used. Fibroblasts can also perform phagocytosis. The ability of fibroblasts to phagoytose other cells can be enhanced by causing them to overexpress molecules that bind to phagocytic markers (68).

Purified cell populations obtained as described above may be used for therapeutic purposes. For example, blood and platelet transfusions are widely used in clinical medicine and frequently play a life-saving role. However, a drawback to these therapies is the risk of introducing a pathogen, or a pathogen-infected cell, into the recipient. Of particular concern is the possibility of infecting the recipient with HIV, HBV, or HCV. The compositions of the invention may be used to remove pathogens, or pathogen-infected cells, from blood or platelet preparations prior to their administration to a subject in essentially the same manner as for the preparation of purified cell populations described above, with the sample being the blood or platelet preparation. The cellular marker is a protein that is expressed specifically on the surface of pathogen-infected cells or on the surface of the pathogen itself.

As another example, bone marrow transplant is a widely used form of therapy for various diseases including cancer. According to this approach a subject is administered a dose of a cytotoxic agent that is lethal to bone marrow cells. After a period of time bone marrow cells (either autologous or from an immunologically compatible donor) are then infused or transplanted into the subject to reconstitute the hematopoietic system. However, this approach carries the risk that the bone marrow cells may contain either tumor cells (in the case of autologous donation) or may contain cells infected with a pathogen. In either case, it is desirable to eliminate such cells prior to their introduction into the subject. The compositions of the invention may be used to purge bone marrow cells prior to their introduction into a subject, essentially as described above for the preparation of purified cell populations, with the sample being the bone marrow cells to be administered to the subject. The cellular marker can be, for example, either a tumor specific marker or a marker for infection. This approach can be used generally for organ or tissue transplants of any type.

Graft versus host disease (GvHD) commonly occurs as a complication of allogeneic hemopoietic stem cell transplantation (HSCT) and of donor lymphocyte infusions (DLI) as a result of the presence of alloreactive T cells (95). It can also occur following organ transplantation. The acute form of GvHD occurs within 100 days from HSCT or DLI, the chronic form beyond day 100. Several approaches exist to reduce the likelihood or severity of GvHD. Donor T cells can be removed from the transplant (ex vivo T-cell depletion) and/or T-cell antibodies can be administered to the patient (in vivo T-cell depletion). Immunosuppressive drugs such as methotrexate, cyclosporin, tacrolimus, and mycofenolate can be used in addition to or instead of these methods (post-transplant immunosuppression). The compositions of the invention can be used for ex vivo T cell depletion. Compositions comprising a ligand or antibody that recognizes T cells are preferably used. The compositions can also be used for in vivo T cell depletion, as described below.

In any of these applications, according to certain embodiments of the invention, it is not necessary to perform the step of contacting the sample with phagocytic cells prior to introducing the blood, platelet preparation, bone marrow cells, tissue or organ transplant, etc., into the subject. Instead, phagocytosis can take place in the subject's body, after introduction of the cells, tissue, or organ. The cells, tissue, or organ is contacted with a composition of the invention for a period of time, during which molecules of the composition bind to a cellular marker on an undesired cell type or on a pathogen. The cells, tissue, or organ are then introduced into the subject, after which the subject's own phagocytic cells (e.g., macrophages) phagocytose the undesired cells or pathogens. The invention therefore provides a method of preparing a cell, tissue, or organ for introduction into a subject comprising (i) contacting the cell, tissue, or organ with a composition comprising a moiety that binds to a cellular marker, wherein a molecule that is a phagocytic marker is linked to the moiety; and (ii) maintaining the cell, tissue, or organ in the presence of the composition for a period of time, so that molecules of the composition bind to the cellular marker. The cell, tissue, or organ can then be administered to the subject.

When used for any of the foregoing purposes, or others, the molecules of the invention may be mixed with suitable solvents, diluents, carriers, etc., as further discussed below. In addition, it will be appreciated that suitable salts may be employed, as further discussed below.

Evaluating Activity of the Compounds

A variety of different methods may be used to evaluate the activity of the inventive compounds. As described in Examples 1, 3, and 4, the ability of a compound to enhance phagocytosis of target cells can be evaluated in vitro by contacting target cells with the compound and then incubating the cells in the presence of phagocytes. Preferably treatment with a compound results in at least a 25% increase, at least a 50% increase, at least a 75% increase, at least a 2-fold increase (i.e., a 100% increase) in phagocytosis as compared to one or more negative control, more preferably at least a 3-fold, at least a 5-fold, or at least a 10-fold increase. The increase may be measured by calculating the phagocytic index, which is preferably at 1.25-fold, at least 1.5-fold, at least 1.75-fold, at least 2-fold, at least 3-fold, at least 5-fold, or at least 10-fold as great when cells are treated with the compound than in either of the negative control cases. Alternately or additionally, a compound preferably results in phagocytosis at levels at least 25%, at least 50%, at least 75%, at least 90%, or 100% or greater as compared with the level of phagocytosis of the positive control cells. Preferably the increase in phagocytosis occurs at compound concentrations in the nanomolar range, e.g., 50-100 nM, 100-500 nM, 500-1000 nM, inclusive.

The compounds may be tested in a number of other ways. For example, when the compounds are used to eliminate one or more undesired cell types from a cell population in vitro, the number of remaining cells of the undesired type can be determined, e.g., using labeled antibodies that specifically bind to a cellular marker present on the undesired cells but not present on other cell types in the composition.

To test the ability of pre-treatment of cells (or a tissue or organ transplant) with a composition of the invention to enhance phagocytosis of undesired cells in vivo following administration of the cells to a subject, the cells, tissue, or organ can be "spiked" with a known number of cells of the undesired type, preferably labeled, prior to incubation with the compound. The cells, tissue, or organ are then administered to the subject. After a period of time, a sample is obtained (e.g., blood, tissue). The number of cells of the undesired type in the sample is evaluated and compared with the number of cells in a similar sample obtained from a subject who was administered a comparably spiked cell, tissue, or organ preparation that was not pretreated with the compound.

The compositions can also be tested in various animal models of disease. For example, to evaluate the anti-tumor properties of a compound of the invention, it can be administered in various doses to mice, dogs, or other animals that have either spontaneous or transplanted tumors (e.g., animals into which tumorigenic cell lines or tissue are injected or transplanted). Numerous such models are known in the art including animals genetically engineered to overexpress an activated oncogene (see U.S. Pat. No. 4,736,866), animals in which cancer has been induced by exposure to a carcinogenic agent, immunodeficient or immunosuppressed animals (see U.S. Pat. No. 6,107,540 describing a murine model for prostate cancer; U.S. Pat. No. 6,284,239, describing murine models for human breast, prostate, or ovarian cancer); U.S. Pat. No. 6,706,947, describing a large animal model for cancer). Criteria such as tumor size, tumor vasculariation, number of metastases, average survival time, etc., can be assessed.

The effect of angiogenesis inhibitors has been examined in a number of animal models. For example, Folkman described the ability of angiostatin to suppress metastases in a Lewis lung carcinoma model (107) and also examined its inhibitory effect on human tumors in mice (108). Bougnoux compared the effect of various therapies including the anti-angiogenic agent TNP-470 on tumor vascularization and tumor response in a nitrosomethyl urea induced rat mammary tumor model (109). Folkman examined the effect of PPARg ligands on primary tumors in model systems in which glioblastoma, Lewis lung carcinoma, rhabdomyosarcoma, or liposarcoma cells were transplanted subcutaneously into mice (106). The effect of the anti-angiogenic agent TNP-470 on hemangiomas was studied in an animal model in which rats are infected with murine polyomavirus, resulting in the development of multiple hemangiomas (110).

Animal models are available to study the various other diseases and conditions mentioned herein. For example, collagen-induced arthritis is an animal model for rheumatoid arthritis that shares a number of features with human disease (113). CC chemokine receptor 2 knockout mice are another such model (112). Models exist for age-related macular degeneration (111), proliferative retinopathy (114) and choroidal neovascularization (32). These examples are but a few of the model systems in which efficacy of the compounds of the invention can be assessed. The effect of the inventive compounds on angiogenesis can be studied using any of a variety of imaging methods available to study angiogenesis in animal models (115).

Compounds that show promising results in animal studies are tested in humans using standard protocols and endpoints for clinical trials. Imaging may be particularly helpful in evaluating the efficacy of the compounds in inhibiting vascularization of tumors, vascularization in the eye, etc.

Pharmaceutical Compositions

Suitable preparations, e.g., substantially pure preparations of the inventive compounds may be combined with pharmaceutically acceptable carriers, diluents, solvents, etc., to produce an appropriate pharmaceutical composition. The invention therefore provides a variety of pharmaceutically acceptable compositions for administration to a subject comprising (i) an agent that increases the level or density of a phagocytic marker on or at the surface of a cell or molecular entity; and (ii) a pharmaceutically acceptable carrier, adjuvant, or vehicle. In particular, the invention provides a pharmaceutically acceptable composition comprising (i) a moiety that binds to a cellular marker, wherein a molecule that is a phagocytic marker is linked to the antibody or ligand; and (ii) a pharmaceutically acceptable carrier, adjuvant, or vehicle. The marker may be a cell type specific marker. The invention provides pharmaceutical compositions containing one or more of the inventive compounds described and/or shown herein.

In certain embodiments of the invention the pharmaceutical composition detectably inhibits vascularization, e.g., in a tumor or in an eye, following administration to a subject. In other words, administration of the compound measurably reduces vascularization relative to the expected level in the absence of the composition. It is to be understood that the pharmaceutical compositions of the invention, when administered to a subject, are preferably administered for a time and in an amount sufficient to treat or prevent the disease or condition for whose treatment or prevention they are administered.

Further provided are pharmaceutically acceptable compositions comprising a pharmaceutically acceptable derivative (e.g., a prodrug) of any of the compounds of the invention, by which is meant any non-toxic salt, ester, salt of an ester or other derivative of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also able to increase the level or density of a phagocytic marker on or at the surface of a cell or molecular entity.

In various embodiments of the invention an effective amount of the pharmaceutical composition is administered to a subject by any suitable route of administration including, but not limited to, intravenous, intramuscular, by inhalation, by catheter, intraocularly, orally, rectally, intradermally, by application to the skin, etc. According to certain embodiments of the invention a molecule such as MFG-E8, β-glycoprotein, protein S, annexin I, etc., which may enhance recognition or binding of phagocytotic cells to cells or molecules to be engulfed, is also administered to the subject either together with or separately from the compositions of the invention.

Inventive compositions may be formulated for delivery by any available route including, but not limited to parenteral, oral, by inhalation to the lungs, nasal, bronchial, opthalmic, transdermal (topical), transmucosal, rectal, and vaginal routes. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or by inhalation.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Supplementary active compounds, e.g., compounds independently active against the disease or clinical condition to be treated, or compounds that enhance activity of an inventive compound, can also be incorporated into the compositions.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

A pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), phosphate buffered saline (PBS), or Ringer's solution.

Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In all cases, the composition should be sterile, if possible, and should be fluid to the extent that easy syringability exists.

Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of injectable compositions can be brought about by including in the composition an agent which delays absorption, for example, aluminum monostearate and gelatin. Prolonged absorption of oral compositions can be achieved by various means including encapsulation.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions are preferably delivered in the form of an aerosol spray from a pressured container or dispenser which contains a suitable propellant, e.g., a gas such as carbon dioxide, or a nebulizer. Liquid or dry aerosol (e.g., dry powders, large porous particles, etc.) can be used. The present invention also contemplates delivery of compositions using a nasal spray.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In addition to the delivery agents described above, in certain embodiments of the invention, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polyethers, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811 and other references listed herein.

It is typically advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

A therapeutically effective amount of a pharmaceutical composition typically ranges from about 0.001 to 100 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The pharmaceutical composition can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with an inventive composition can include a single treatment or, in many cases, can include a series of treatments.

Exemplary doses include milligram or microgram amounts of the inventive compounds per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.) For local administration (e.g., intranasal), doses much smaller than these may be used. It is furthermore understood that appropriate doses depend upon the potency of the agent, and may optionally be tailored to the particular recipient, for example, through administration of increasing doses until a preselected desired response is achieved. It is understood that the specific dose level for any particular subject may depend upon a variety of factors including the activity of the specific compound employed, the age, body weight, general health, gender, and diet of the subject, the time of administration, the route of administration, the rate of excretion, any drug combination, and the degree of expression or activity to be modulated.

As mentioned above, the present invention includes the use of inventive compositions for treatment of nonhuman animals including, but not limited to, companion animals such as dogs and cats, agriculturally important animals such as ruminants (e.g., cows), sheep, horses, etc. Accordingly, doses and methods of administration may be selected in accordance with known principles of veterinary pharmacology and medicine. Guidance may be found, for example, in Adams, R. (ed.), *Veterinary Pharmacology and Therapeutics*, 8$^{th}$ edition, Iowa State University Press; ISBN: 0813817439; 2001.

As mentioned above, annexin I is a glucocorticoid-regulated protein. According to certain embodiments of the invention a glucocorticoid (e.g., prednisone or any of a wide variety of glucocorticoids) is administered at about the same time, or shortly before (e.g., a few days, or hours before), or shortly after administration of a composition of the invention in order to increase endogenous annexin I expression and thereby enhance phagocytosis. A similar approach can be followed in the case of other molecules that enhance recognition or binding of phagocytotic cells to a target, i.e., compounds that increase endogenous expression of the molecule can be administered to the subject. For example, MSC (Avemar®) is a composition derived from wheat germ extract, which has been shown to increase expression of ICAM-1 (99). In addition, it has been shown to have anti-cancer and anti-apoptotic properties. Avemar can be administered to a subject in conjunction with administration of a composition of the invention. Alternatively or additionally, compounds that generally enhance the activity of phagocytic cells or cause an increase in their number, e.g., that enhance macrophage activity or stimulate macrophage proliferation or maturation, can be administered to the subject. For example, various interferons and interleukins are known to have one or more of these effects.

The invention further provides pharmaceutical compositions comprising two or more molecular species of the invention, each comprising a moiety that binds to a cellular marker, wherein the cell-binding moieties in each molecular species bind to a different cellular marker. The invention further provides pharmaceutical compositions comprising one or more molecular species of the invention and a second agent, wherein the agent is a chemotherapeutic agent, e.g., an agent of any of the classes mentioned above. In certain embodiments of the invention the chemotherapeutic agent is an angiogenesis inhibitor.

EXAMPLES

Example 1

Enhancement of Phagocytosis by a PS Derivative

Materials and Methods
Cells and Cell Culture.

Human umbilical vein endothelial cells (HUVECs) and MonoMac-1 cells (a human myeloma cell line) were obtained from Cambrex Inc., East Rutherford, N.J., and were maintained under standard culture conditions. Both cell lines are adherent under these culture conditions.

Compound Synthesis.

The phosphatidylserine derivative shown in FIG. 4C, containing a PS headgroup, was synthesized according to the scheme shown in FIG. 4A, which is described above. The commercially available phosphatidylcholine derivative 1-Hexanoyl-2-Hydroxy-sn-Glycero-3-Phosphocholine (Cat. No. 855175 Avanti Polar Lipids, Alabaster, Ala.) was used, resulting in a compound in which R is a 5 carbon chain. The PS derivative reacts with free thiols in proteins on the cell surface. In other experiments, the phosphatidylcholine derivative 1-Myristoyl-2-Hydroxy-sn-Glycero-3-Phosphocholine or 1-Tetradecanoyl-2-Hydroxy-sn-Glycero-3-Phosphocholine (Cat. No. 855575, Avanti Lipids) is used, resulting in a compound in which R is a 13 carbon chain.

Phagocytosis Assay.

Target HUVECs were plated 48 hours prior to the assay in 24-well dishes with cover slips at a density of 50,000 cells per well. Twenty-four (24) hours prior to the assay, cells were stained with a live cell dye. To do so, CellTracker™ Red (Molecular Probes, Eugene, Oreg.) was added to cells at a 2 micromolar concentration. Cells were stained for 30 minutes at 37° C. in serum-free RPMI. Cells were then washed twice in complete RPMI (10% FBS, high glucose DMEM) and allowed to recover overnight in complete medium.

MonoMac-1 cells were grown in suspension in complete RPMI. Twenty-four hours prior to the phagocytosis assay, cells were stained with 2 micromolar CellTracker™ Green (Molecular Probes) in serum-free media for 30 minutes at 37° C. Cells were centrifuged at 300 g, washed with complete RPMI, centrifuged a second time, and resuspended in complete RPMI. Cells were allowed to recover overnight in complete medium.

Four hours before the phagocytosis assay, cells were either UV-irradiated to induce apoptosis (positive control cells), treated with the PS derivative (experimental groups), or left untreated (live cell negative control). Five concentrations of compound were used: 500 micromolar, 100 micromolar, 20 micromolar, 4 micromolar, and 0.8 micromolar. Untreated and UV-irradiated cells were included as controls. For UV irradiation, dishes were placed atop a 254 nm light source for 10 minutes. For compound treatment, cells were exposed to the compound for 30 minutes at 37° C. in serum-free media. All experimental conditions were performed in duplicate. The compound-containing media was then removed and cells were washed twice in complete RPMI. All cells were allowed to recover (or allow apoptotic program to proceed) for 3.5 hours before the MonoMac-1 cells were added. Cells from all three groups (untreated, treated with compound, and UV-irradiated) remained adherent at this time.

At the zero time point of the assay, MonoMac-1 cells were added to HUVECs at a ratio of 5 MonoMac-1 cells per HUVEC. For the 24-well assay described here, this represents 250,000 MonoMac-1 cells added to 50,000 HUVEC cells. Cells were co-incubated for 6 hours. At this time point, most HUVEC cells remained adherent. Furthermore, if a HUVEC has been recognized by a MonoMac-1 cell, the phagocyte will be effectively be adherent through this association.

After six hours, supernatants were removed from cells (supernatants are typically saved for subsequent analysis). Wells were washed twice with complete media and twice with PBS. Cells were then fixed with 3% paraformaldehyde for 30 minutes at room temperature. Wells were washed twice with PBS. Cover slips were then dried and mounted on slides for microscopic analysis. Phagocytic indices were calculated by examining and counting the number of live HUVECs and MonoMac-1 cells in ten random fields from each condition. By raster scanning across the cover slip, ten adjacent fields were examined. The phagocytic index was defined as the number of adherent MonoMac-1 cells per live HUVEC. The phagocytic index was determined for each field. Because of variations in staining intensities, the highest and lowest value from each field was removed (trimmed) before calculation of the average of phagocytic indices of the 8 remaining fields (which is the same as the total number of adherent MonoMac-1 cells in the 8 fields divided by the total number of HUVECs in the 8 fields).

Results

In order to evaluate the compounds of the invention, an assay system in which cells of a human myeloid line (MonoMac-1) recognize apoptotic or necrotic human umbilical vein endothelial cells (HUVECs) was developed. MonoMac-1 cells adhere to and begin to phagocytose these target cells while generally leaving live cells untouched. Normal (i.e., not apoptotic or necrotic) HUVECs were exposed to 5 different concentrations of the PS derivative shown in FIG. 4C. Untreated cells were included as a negative control. Cells that had been UV irradiated to induce apoptosis served as a positive control.

Figure 16:
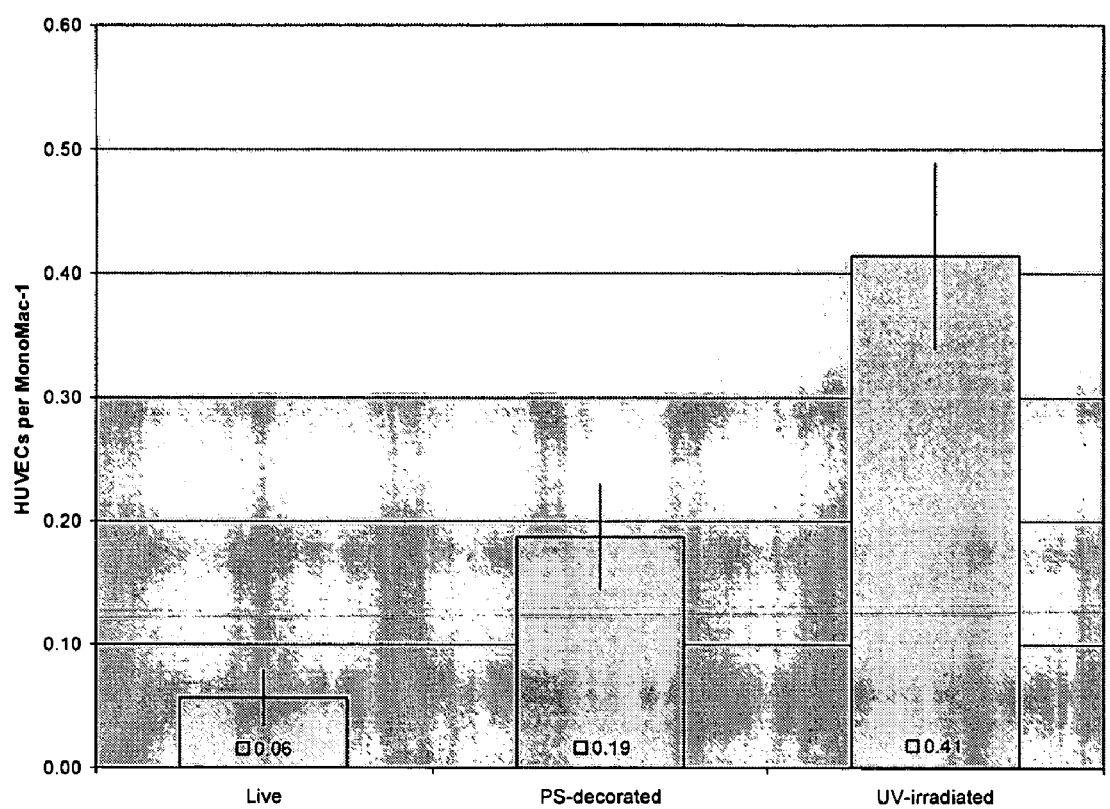
FIG. 16 is a bar graph showing the phagocytic index for untreated HUVECs that were incubated with MonoMac-1 cells (left), HUVECs that were treated with a phosphatidylserine derivative and then incubated with MonoMac-1 cells (middle), and HUVECs that were exposed to UV radiation to induce apoptosis and then incubated with MonoMac-1 cells (right).

Using colocalization analysis under confocal microscopy, we found that macrophages that adhere to the culture plate can easily be distinguished from macrophages that adhere to or phagocytose endothelial cells. The extent of phagocytosis was evaluated by calculating the phagocytic index, i.e., the number of adherent MonoMac cells per live HUVEC. Table 1 shows the number of each cell type in three experimental conditions: untreated cells, cells treated with 0.8 micromolar PS derivative, and UV irradiated cells. The ratio of adhering MonoMac-1 to HUVEC was 0.06±0.02 for untreated cells, 0.19±0.04 for cells that had been treated with 0.8 micromolar compound, and 0.41±0.07 for cells that had been UV irradiated to induce apoptosis. Thus approximately six percent of live HUVECs had associated MonoMac-1 cells, while approximately forty-one percent of the irradiated HUVECs had associated MonoMac-1 cells. Nineteen percent of the HUVECs treated with 0.8 micromolar (800 nM) PS-analog had associated MonoMac-1 cells. FIG. 16 shows the results in graphical form.

TABLE 1

| Untreated HUVEC | MonoMac-1 | Ratio | Ratio (trimmed) |
|---|---|---|---|
| 31 | 0 | 0 | |
| 47 | 1 | 0.021276596 | 0.021276596 |
| 85 | 5 | 0.058823529 | 0.058823529 |
| 53 | 2 | 0.037735849 | 0.037735849 |
| 46 | 2 | 0.043478261 | 0.043478261 |
| 71 | 4 | 0.056338028 | 0.056338028 |
| 87 | 5 | 0.057471264 | 0.057471264 |
| 70 | 6 | 0.085714286 | 0.085714286 |

TABLE 1-continued

|  | | | | |
|---|---|---|---|---|
|  | 66 | 6 | 0.090909091 | 0.090909091 |
|  | 68 | 12 | 0.176470588 |  |
| Total | 624 | 43 | 0.068910256 |  |
| Average | 62.4 | 4.3 | 0.068910256 | 0.056468363 |
| StDev | 16.94815624 | 3.257299495 | 0.020113668 | 0.021812175 |

| HUVEC treated with PS derivative | MonoMac-1 | Ratio | Ratio (trimmed) |
|---|---|---|---|
| 58 | 7 | 0.120689655 |  |
| 78 | 12 | 0.153846154 | 0.153846154 |
| 64 | 10 | 0.15625 | 0.15625 |
| 63 | 11 | 0.174603175 | 0.174603175 |
| 68 | 12 | 0.176470588 | 0.176470588 |
| 84 | 15 | 0.178571429 | 0.178571429 |
| 78 | 14 | 0.179487179 | 0.179487179 |
| 76 | 14 | 0.184210526 | 0.184210526 |
| 61 | 18 | 0.295081967 | 0.295081967 |
| 33 | 10 | 0.303030303 |  |
| Total 663 | 123 | 0.185520362 |  |
| Average 66.3 | 12.3 | 0.185520362 | 0.187315127 |
| StDev 13.80615805 | 2.93428015 | 0.044809731 | 0.042020042 |

| UV irradiated HUVEC | MonoMac-1 | Ratio | Ratio (trimmed) |
|---|---|---|---|
| 51 | 13 | 0.254901961 |  |
| 66 | 21 | 0.318181818 | 0.318181818 |
| 72 | 26 | 0.361111111 | 0.361111111 |
| 34 | 14 | 0.411764706 | 0.411764706 |
| 26 | 11 | 0.423076923 | 0.423076923 |
| 39 | 17 | 0.435897436 | 0.435897436 |
| 29 | 14 | 0.482758621 | 0.482758621 |
| 58 | 28 | 0.482758621 | 0.482758621 |
| 57 | 28 | 0.49122807 | 0.49122807 |
| 46 | 26 | 0.565217391 |  |
| Total 478 | 198 | 0.414225941 |  |
| Average 47.8 | 19.8 | 0.414225941 | 0.425847163 |
| StDev 14.88489167 | 6.415605973 | 0.074840177 | 0.057924597 |

Thus treatment with the compound at 0.8 micromolar increased the phagocytic index by a factor of approximately 3, to approximately half the level of phagocytosis observed in the UV irradiated apoptotic cells. Interestingly, HUVECs that were exposed to the compound at higher concentrations (500, 100, and 20 micromolar) had fewer associated MonoMac-1 cells, similar to the untreated controls. A similar effect was noticed in the case of cells engineered to overexpress the phagocytic marker MFG-E8, i.e., beyond a certain expression level phagocytosis was decreased (68). Toxicity was observed only at the highest two compound concentrations used.

Figure 17A:
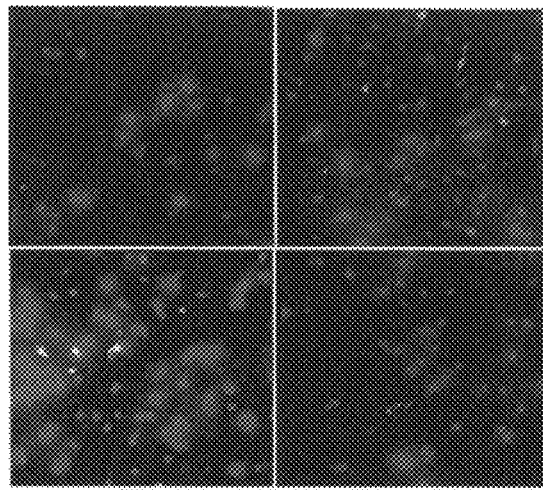
FIG. 17A shows images (100× magnification) of HUVECs that were treated with a phosphatidylserine derivative and then incubated with MonoMac-1 cells.
Figure 17B:
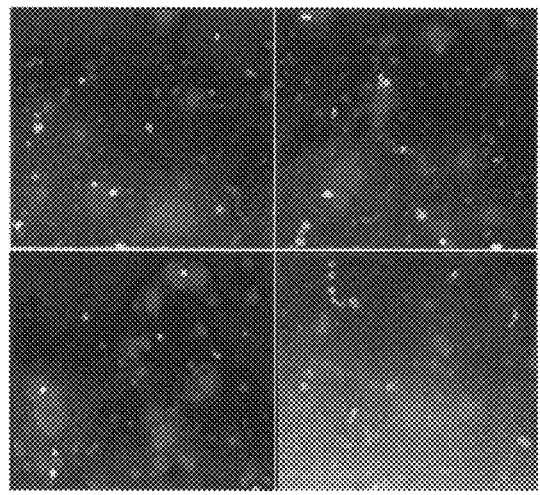
FIG. 17B (100× magnification) shows HUVECs that were treated with a similar phosphatidylcholine derivative and then incubated with MonoMac-1 cells.

FIG. 17A shows images (100× magnification) from the group of cells treated with the PS derivative at 800 nM. Typically about 100 HUVECs (red) and 10-20 MonoMac-1 cells (green) are seen. In a similar experiment, a phagocytosis assay was performed using HUVECs that were treated with the phosphatidylcholine (PC) precursor of the PS derivative pictured in FIG. 4C. FIG. 17B (100× magnification) shows cells treated with this PC derivative. Most fields contain between 1 and 5 MonoMac-1 cells (green) and about 100 HUVECs (red). Thus the phagocytic index was approximately the same as for untreated cells, indicating that the increased phagocytosis seen in the group that was treated with the PS derivative is likely due to the presence of the PS headgroup rather than due to the other portions of the molecule.

Figure 17C:
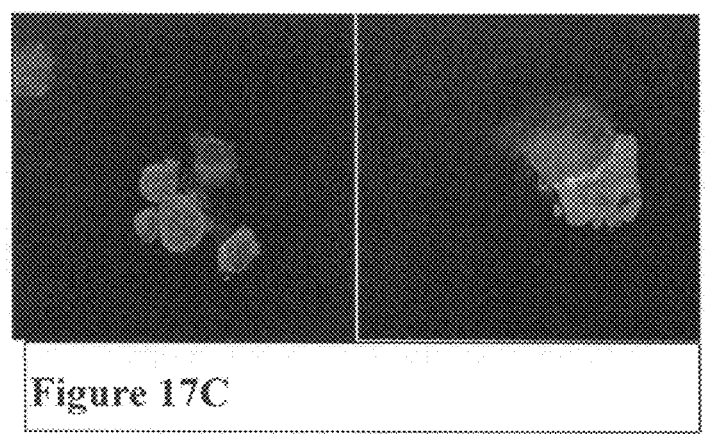
FIG. 17C shows higher magnification images of Mono-Mac-1 cells associated with HUVECs that had been treated with a PS derivative). In one image (left, 1,200×), several MonoMac-1s are associated with a single HUVEC. In the other image (right, 2000×), a single MonoMac-1 cell is associated with a single HUVEC and presumably beginning to engulf it.

FIG. 17C shows higher magnification images of MonoMac-1 cells associated with HUVECs (treated with 0.8 micromolar PS-analog). In one image (left, 1,200×), several MonoMac-1s are associated with a single HUVEC. In the other image (right, 2000×), a single MonoMac-1 cell is associated with a single HUVEC and presumably beginning to engulf it.

Taken together, these results are much more consistent with phagocytes recognizing the PS headgroup decorating the HUVEC surface than with a response to some toxicity caused by the treatment and indicate that (i) treatment with the PS derivative successfully increased the level of the PS headgroup on the cell surface; (ii) increased levels of this phagocytic marker enhanced phagocytosis of the target cells. Additional experiments suggest that even lower levels of decoration with the PS headgroup can stimulate phagocytosis (data not shown). It is therefore likely that treatment with other PS derivatives will have similar effects.

Example 2

Synthesis of an MGF-E8-Streptavidin Fusion Protein

MFG-E8 (GenBank: NM_0045928) is a protein of 387 amino acids. Two splicing variants of this protein exist, an S form and an L form. While they differ only by a proline-rich motif present in the L form, the L form has been demonstrated to be more active and is used here.

Obtaining MFG-E8 cDNA. Human MFG-E8 is obtained by PCR from a first-strand cDNA library obtained from human fetal spleen tissue (BD Clonetics). An epitope tag (FLAG) is then incorporated into the N-terminal part of the protein between the signal peptide (amino acid residues 1-22) and the first EGF-like domain (amino acid residues 24-61). This tag can be used for monitoring protein expression by Western analysis and for purification with the use of anti-FLAG antibodies and anti-FLAG M2 affinity gel (Sigma) respectively.

Fusing MFG-E8 with SAV. Fusing MFG-E8 to SAV (GenBank: X03591) should provide MFG-E8 with the ability to bind cells that have been surface-decorated with biotin. A gene corresponding to the 159 amino acid mature peptide (nucleotides 122-601 of X03591) of SAV is made synthetically. Specifically, 40-mer oligonucleotides spanning the length of this region on both sense and anti-sense strands are synthesized using standard methods. Sense and anti-sense oligonucleotides for each segment are ten nucleotides out of register to allow for a 5' overhang between adjacent segments. These oligonucleotides are kinased, annealed, combined with other segments, and ligated together with T4 DNA ligase. The assembled gene is then amplified by PCR from the ligation mixture and cloned into a plasmid vector, yielding the SAV domain of the fusion protein. The complete fusion gene (MFG-SAV) is made by overlap extension PCR that removes the stop codon of MFG-E8 and introduces a $(Gly_3Ser_1)_3$ between the MFG-E8 and SAV domains. The amplified product is cloned into vectors for production in mammalian cells (pcDNA5/FRT/TO, Invitrogen) or insect cells (pBlueBac4.5, Invitrogen).

Preferably the protein is expressed in mammalian cells, which likely maximizes the chance that the MFG domain will fold correctly and be properly post-translationally modified. However, baculoviral expression systems provide an alternative and may result in higher yields since, in general, baculoviral expression systems tend to have substantially better yields than mammalian ones.

For production in mammalian cells, the Flp-In T-Rex system (Invitrogen) is used to generate stable, tetracycline-inducible 293-based clones. This system allows integration of a single copy of the vector into a defined location known to support high gene expression. The media used during the production phase is depleted of biotin with avidin-agarose (Pierce) to avoid complexing the fusion protein with free biotin. It is harvested from culture supernatant as a secreted protein and purified using anti-FLAG M2 affinity gel (Sigma). Protein expression is verified by Western analysis using an anti-FLAG M2 antibody (Sigma) against the introduced FLAG epitope for detection. This mammalian expression system is the system of choice as it increases the likelihood that the fusion protein will contain all the post-translational modifications found in wild-type MFG.

For production in Sf9 insect cells, the Bac-N-Blue system (Invitrogen) is used. Cells are switched to media depleted of biotin (as above) after infection to limit complexation of the expressed protein by free biotin. The protein is isolated and its expression verified as described above.

Example 3

Effect of MFG-E8 Derivatives on Phagocytosis

This example describes assessment of the ability of two different MFG-E8 derivatives to enhance phagocytosis of target cells in vitro. The target cells used here are endothelial precursor cells (EPCs) (101). These cells exhibit a gene expression profile more similar to that of cells isolated from fresh surgical specimens of human tumors than HUVECs and may thus be preferable for use in such assays. In addition, the phagocytic cells are human blood-derived (HBD) macrophages rather than MonoMac-1 s.

Preparation of EPC and macrophage cell cultures. EPCs are prepared as described by Bagley et al (101). CD34+/AC133+ progenitor cells from human bone marrow cells will be purchased from Cambrex. They will be grown at 1-2×105 cells/ml in IMDM medium (Cambrex) supplemented with 15% FBS (Invitrogen Corp., Carlsbad, Calif.), 50 ng/ml VEGF165 (R&D Systems, Minneapolis, Minn.), 50 ng/ml rhbFGF (R&D Systems), and 5 units/ml heparin (Sigma, St. Louis, Mo.) on fibronectin-coated flasks (BD Biosciences, Franklin Lakes, N.J.) at 37° C. with humidified 95% air/5% $CO_2$ to generate EPCs (5). Fresh media will be added every 3 days. The adherent cells that will be generated from the original population of mixed adherent/non-adherent cells will be designated EPCs. Cells will be passaged up to 12 times. After the second passage, no more growth factors will be added to the media. Macrophage cell cultures will be prepared according to the Cambrex protocol. Briefly, cells will be thawed in a 37° C. water bath, and 2 ml of cell suspension will be added to a 50 ml tube in 1 ml of medium supplemented with 10% FBS. Volume will be adjusted with medium+FBS until the tube is full. Cells will then be washed twice, resuspended in 2 ml medium, and allowed to rest for 1 hour at 37° C. and 5% $CO_2$. After that, the cells are placed in culture. Medium is changed every 2 days and cells are allowed to mature for 10 days before use.

Phagocytosis assays. Epithelial precursor cells (EPCs) are grown in 24-well dishes to a density of 50,000 cells per well (about 30% confluency). Cells are incubated with a PS derivative, a phosphatidylcholine analog (as a negative control), or mock-treated in serum-free media for 30 minutes at 37° C. EPCs will are washed twice to remove residual compound and resuspended in complete media. Cells are allowed to recover for one hour at 37° C. CD14+ human peripheral blood monocytes (or macrophages) are then added. (The CD 14+ cells are grown in Teflon dishes to prevent them from adhering to the plate.) Phagocytes are added to EPCs at a ratio of 5:1. Cells are incubated for 18 hours at 37° C. in complete media. Cells are then prepared for either FACS or microscopic analysis.

For microscopic analysis, cells are grown on cover slips. After co-incubation, cells are fixed, permeabilized and stained with two fluorescently-labeled primary antibodies, one specific for CD14 (for phagocytes) and one specific for CD146 (for endothelial cells) (99). In some experiments an unlabeled anti-CD146 primary antibody is used, in which case cells are incubated with the secondary Alexafluor 596 goat anti-mouse highly cross-absorbed monoclonal antibody for 30 minutes on ice. After washing to remove residual antibody, cells are viewed by fluorescent or confocal microscopy. For FACS analysis, cells are removed from the dish after co-incubation by trypsinization or scraping. In some experiments, non-adherent cells are used, in which case the media is centrifuged, and the cells re-diluted at $10^6$ cells/ml. They are then fixed, permeabilized, and antibody-labeled as described above. Cells are analyzed on a FACScalibur (BD Bioscience).

It may be desirable to distinguish actual phagocytosis from simple adherence of the phagocyte to the target cell. Although co-localization of the phagocytic cell and the ECS markers is consistent with phagocytosis, more definitive evidence may be obtained. For example, engulfment can be confirmed by showing co-localization of the ECS cell with the lysosome-specific marker, LAMP-2 (lysosome associated membrane protein-2 (100). To do so, ECS cells are again be stained with an antibody specific for CD 146; lysosomes of the phagocytic cell are stained with a fluorescently-labeled antibody specific for LAMP-2. Co-localization of these two markers when viewed under a confocal microscope shows ECS cell engulfment.

Figure 13:
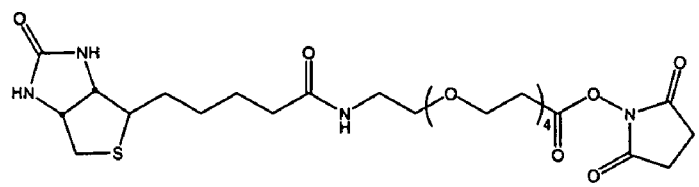
FIG. 13 shows a commercially available amine-reactive biotin derivative.

Determination of macrophage activity towards EPCs displaying MFG-E8. EPCs are biotinylated non-specifically using an N-hydroxysuccinimide ester (NHS-ester)-functionalized biotin derivative (FIG. 13). The biotin residues are coupled to extracellular membrane protein domains through available lysines. The EPCs are washed and then incubated them the MFG-SAV fusion protein produced as described in Example 2. The number of MFG-SAV fusion proteins on the surface of the EPCs is then determined using radio-labeled anti-MFG antibodies (see Example 5). EPCs are coincubated with HBD macrophages, and the phagocytotic index is computed. The level of phagocytosis relative to the number of MFG-SAV groups on the surface of the EPCs is determined. As negative controls, the level of phagocytosis of: (1) untreated EPCs and (2) EPCs that were biotinylated and treated with fluorescent SAV, followed by incubation with HBD macrophages, is determined. As positive controls, EPCs that were rendered apoptotic by 10 min of UV irradiation (254 nm) are used.

Determine macrophage activity toward EPCs in the presence of an anti(αvβ3)-biotin/MFG-SAV conjugate. An anti-integrin (αvβ3)-biotin conjugate is synthesized by biotinylating an anti-integrin (αvβ3) Mab using an N-hydroxysuccinimide ester (NHS-ester)-functionalized biotin derivative (FIG. 13). The biotin residues are coupled to the Mab through available lysines. Conjugates comprising either a single-chain, Fab', F(ab')$_2$, or complete antibody are generated. EPCs are incubated with the anti-integrin (αvβ3)-biotin conjugate and the MFG-SAV fusion protein either together or sequentially. In some experiments EPCs are first exposed to the anti-integrin (αvβ3)-biotin conjugate, and the MFG-SAV fusion protein is added after a period of time, either with or without washing away unbound anti-integrin (αvβ3)-biotin conjugate. In other experiments the two molecules are added together. In yet other experiments, the anti-integrin (αvβ3)-biotin conjugate and the MFG-SAV fusion protein are pre-incubated to allow the formation of a complex, and EPCs are exposed to the resulting conjugate. After coincubating the EPCs with HBD macrophages, the level of phagocytosis is determined as described above. The control groups are the same as those used to determine macrophage activity towards EPCs that were biotinylated directly and then treated with MFG-SAV conjugate.

Example 4

Effect of PS Derivatives on Phagocytosis

This example describes assessment of the ability of a PS derivative comprising a PS head group to enhance phagocytosis of target cells in vitro. Cells, cell culture, and phagocytosis assays, are as described in Example 3.

Determine Macrophage Activity Toward EPCs in the Presence of PS Conjugate

The PS derivative labeled as compound 9 in FIG. 11 is synthesized as described above. This conjugate possesses a thiol-reactive group that reacts readily with free sulfhydryls present on the surface of the cell. HUVECs or EPCs are incubated with compound 9 at concentrations ranging from 50 nm to 1 μm. The number of PS derivative molecules on the surface of the HUVECs or EPCs is quantified as described in Example 5, using a portion of the cells from each treatment condition. Cells from each treatment condition are coincubated with HBD macrophages or MonoMac-1 macrophages as described in Example 1 or 3, and the level of phagocytosis relative to the number of PS conjugates on the surface of the target cells is computed. As negative controls, the level of phagocytosis of: 1) untreated HUVECs or EPCs and 2) HUVECs or EPCs that were treated with a phosphatidylcholine derivative (compound 8 in FIG. 11) is assessed. As positive controls, HUVECs or EPCs that were rendered apoptotic either by exposure to UV radiation as described in Example 1 or by exposure to the pro-apoptotic molecule FasL (Fas ligand) are used.

For induction of apoptosis by FasL, HUVECs are grown in 24-well dishes to a density of 50,000 cells per well (~30% confluency). Cells are incubated in 200 ul of media containing 2 ng of FasL for 24 hours at 37° C. with humidified 95% air/5% $CO_2$. HUVECs are then washed twice to remove residual FasL. Cells are allowed to recover for one hour at 37° C.

Determine macrophage activity toward EPCs in the presence of an anti(αvβ3)—PS conjugate. The PS derivative labeled as compound 9 in FIG. 11 is synthesized as described above. This conjugate possesses a thiol-reactive group that reacts readily with free sulfhydryls present in proteins. Compound 9 is allowed to react via its thiol-reactive group with free sulfhydryls on an IgG F(ab')$_2$ (anti-integrin αvβ3) monoclonal antibody (Novus Biologicals). EPCs are incubated with the resulting integrin αvβ3-targeted/PS derivative conjugate at a range of concentrations. Cells are then washed to remove unbound conjugate and coincubated with HBD macrophages as described above. The level of phagocytosis is assessed. The control groups will be the same as those used to determine macrophage activity towards EPCs that were directly functionalized with the PS derivative compound 9 via free thiols on their surface. Additional test groups include 1) cells that do not express integrin αvβ3 and 2) cells that have been engineered to express integrin αvβ3 at higher levels than EPCs. The extent to which targeting the PS derivative to the cellular marker integrin αvβ3 enhances phagocytosis is assessed.

Example 5

Quantification of Phagocytic Marker Delivery and Levels of Cellular Marker on Cell Surface This example describes determination of the amount of PS derivative or MFG-E groups after incubation of cells in the presence of a PS derivative or MFG-E8 derivative comprising a cell-binding moiety that binds to the cellular marker. Such quantification is useful, e.g., to select desirable cell-binding moieties. The example also describes quantification of the level of cellular marker on the EPC cell surface. Such quantification is useful, e.g., to select desirable cellular markers.

The amount of PS derivative present at the surface of EPCs after functionalization is measured using Annexin V radiolabeled with $^{99m}TC$. Briefly, PS-functionalized EPCs are washed at 4° C. with Hepes buffer containing 1 mM EDTA to remove possible traces of bound Annexin V present in the culture media, and then with Hepes buffer containing 5 mM $CaCl_2$. The EPCs are incubated for 1 hour at 4° C. with different concentrations of radiolabeled Annexin V in Hepes buffer containing 5 mM $CaCl_2$ with continuous shaking. The cells are washed 3 times in Hepes buffer containing 5 mM $CaCl_2$. After removal of the supernatant the total well content is counted for radioactivity. Data points are computed as the average of three determinations. The binding constant and number of binding sites are analyzed using Scatchard plots and calculated by non-linear data fitting. This procedure is identical to that described by van Heerde et al. except for the use of $^{99m}TC$ instead of $^{125}I$ as the radiolabel (102).

Quantification of MFG and the relevant cellular marker (to which the cell-binding moiety binds) on the surface of cells is performed in the same way, except that $^{125}I$-labeled anti-MFG mAb (Novus Biologicals) and $^{125}I$-labeled mAbs that bind to the cell-binding moiety are used, respectively, following the protocol used by Heerde to label Annexin V (102). For example, a $^{125}I$-labeled anti-integrin-αvβ3 Mab (Novus Biologicals) is used to quantitate the amount of integrin-αvβ3.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the claims that follow the reference list.

REFERENCE LIST

1. Kumar, C. C. Integrin alpha v beta 3 as a therapeutic target for blocking tumor-induced angiogenesis. *Curr. Drug Targets.* 4, 123-131 (2003).
2. Eliceiri, B. P. & Cheresh, D. A. Adhesion events in angiogenesis. *Curr. Opin. Cell Biol.* 13, 563-568 (2001).
3. Rehn, M. et al. Interaction of endostatin with integrins implicated in angiogenesis. *Proc. Natl. Acad. Sci. U.S. A* 98, 1024-1029 (2001).
4. Regidor, P. A., Callies, R., Regidor, M. & Schindler, A. E. Expression of the cell adhesion molecules ICAM-1 and VCAM-1 in the cytosol of breast cancer tissue, benign breast tissue and corresponding sera. *Eur. J. Gynaecol. Oncol.* 19, 377-383 (1998).
5. Jiang, Z., Woda, B. A., Savas, L. & Fraire, A. E. Expression of ICAM-1, VCAM-1, and LFA-1 in adenocarcinoma of the lung with observations on the expression of these adhesion molecules in non-neoplastic lung tissue. *Mod. Pathol.* 11, 1189-1192 (1998).
6. Verkarre, V. et al. ICAM-3 and E-selectin endothelial cell expression differentiate two phases of angiogenesis in infantile hemangiomas. *J. Cutan. Pathol.* 26, 17-24 (1999).
7. Etoh, T. et al. Angiopoietin-2 is related to tumor angiogenesis in gastric carcinoma: possible in vivo regulation via induction of proteases. *Cancer Res.* 61, 2145-2153 (2001).

8. Stoeltzing, O. et al. Angiopoietin-1 inhibits vascular permeability, angiogenesis, and growth of hepatic colon cancer tumors. *Cancer Res.* 63, 3370-3377 (2003).
9. Jain, R. K. Tumor angiogenesis and accessibility: role of vascular endothelial growth factor. *Semin. Oncol.* 29, 3-9 (2002).
10. Ogawa, K. et al. The ephrin-A1 ligand and its receptor, EphA2, are expressed during tumor neovascularization. *Oncogene* 19, 6043-6052 (2000).
11. Cheng, N., Brantley, D. M. & Chen, J. The ephrins and Eph receptors in angiogenesis. *Cytokine Growth Factor Rev.* 13, 75-85 (2002).
12. Patarroyo, M., Tryggvason, K. & Virtanen, I. Laminin isoforms in tumor invasion, angiogenesis and metastasis. *Semin. Cancer Biol.* 12, 197-207 (2002).
13. CD 31: marker of angiogenesis and a prognostic factor in adult soft tissue sarcomas. *Expert. Rev. Mol. Diagn.* 2, 526 (2002).
14. Liao, F. et al. Selective targeting of angiogenic tumor vasculature by vascular endothelial-cadherin antibody inhibits tumor growth without affecting vascular permeability. *Cancer Res.* 62, 2567-2575 (2002).
15. Corada, M. et al. A monoclonal antibody to vascular endothelial-cadherin inhibits tumor angiogenesis without side effects on endothelial permeability. *Blood* 100, 905-911 (2002).
16. Breier, G. et al. Regulators of angiogenesis as targets for anti-angiogenic tumor therapy. *Ann. Hematol.* 81 Suppl 2, S71-S72 (2002).
17. Beckner, M. E. Factors promoting tumor angiogenesis. *Cancer Invest* 17, 594-623 (1999).
18. Compagni, A., Wilgenbus, P., Impagnatiello, M. A., Cotten, M. & Christofori, G. Fibroblast growth factors are required for efficient tumor angiogenesis. *Cancer Res.* 60, 7163-7169 (2000).
19. Tanaka, F. et al. Correlation between apoptotic index and angiogenesis in non-small cell lung cancer: comparison between CD105 and CD34 as a marker of angiogenesis. *Lung Cancer* 39, 289-296 (2003).
20. Lenczewski, A. et al. Prognostic significance of CD34 expression in early cervical squamous cell carcinoma. *Folia Histochem. Cytobiol.* 40, 205-206 (2002).
21. Xiao, M. & Dooley, D. C. Cellular and molecular aspects of human CD34+. *Leuk. Lymphoma* 38, 489-497 (2000).
22. Donnelly, D. S. & Krause, D. S. Hematopoietic stem cells can be CD34+ or CD34−. *Leuk. Lymphoma* 40, 221-234 (2001).
23. Hajjar, D. P. & Gotto, A. M. Targeting CD36: modulating inflammation and atherogenesis. *Curr. Atheroscler. Rep.* 5, 155-156 (2003).
24. Febbraio, M., Hajjar, D. P. & Silverstein, R. L. CD36: a class B scavenger receptor involved in angiogenesis, atherosclerosis, inflammation, and lipid metabolism. *J. Clin. Invest* 108, 785-791 (2001).
25. Silverstein, R. L. & Febbraio, M. CD36 and atherosclerosis. *Curr. Opin. Lipidol.* 11, 483-491 (2000).
26. Corbeil, D., Roper, K., Fargeas, C. A., Joester, A. & Huttner, W. B. Prominin: a story of cholesterol, plasma membrane protrusions and human pathology. *Traffic.* 2, 82-91 (2001).
27. Yu, Y., Flint, A., Dvorin, E. L. & Bischoff, J. AC133-2, a novel isoform of human AC133 stem cell antigen. *J. Biol. Chem.* 277, 20711-20716 (2002).
28. Filmus, J. Glypicans in growth control and cancer. *Glycobiology* 11, 19R-23R (2001).
29. Fransson, L. A. Glypicans. *Int. J. Biochem. Cell Biol.* 35, 125-129 (2003).
30. George, D. Platelet-derived growth factor receptors: a therapeutic target in solid tumors. *Semin. Oncol.* 28, 27-33 (2001).
31. Chiellini C. et al., Identification of cathepsin K as a novel marker of adiposity in white adipose tissue. *J. Cell Physiol.* 195(2):309-21 (2003).
32. Bora, P. S., et al., Immunotherapy for choroidal neovascularization in a laser-induced mouse model simulating exudative (wet) macular degeneration. *Proc. Natl. Acad. Sci.* 100(5): 2679-2684 (2003).
33. Moodley Y, et al. Macrophage recognition and phagocytosis of apoptotic fibroblasts is critically dependent on fibroblast-derived thrombospondin 1 and CD36. *Am J Pathol.;* 162(3):771-9 (2003).
34. Fadok, V., et al. Loss of phospholipid asymmetry and surface exposure of phosphatidylserine is required for phagocytosis of apoptotic cells by macrophages and fibroblasts. *J. Biol. Chem.;* 276: 1071-1077 (2001).
35. Anderson, H. A., et al. Serum-derived protein S binds to phosphatidylserine and stimulates the phagocytosis of apoptotic cells. *Nat Immunol.* 4(1):87-91 (2003).
36. Ishimoto, Y, et al., Promotion of the uptake of PS liposomes and apoptotic cells by a product of growth arrest-specific gene, gas6. *J Biochem (Tokyo).* 127(3):411-7.
37. Mevorach, D., et al. Complement-dependent clearance of apoptotic cells by human macrophages. *J Exp Med.* 188 (12):2313-20 (1998).
38. Roviezzo F, The annexin-1 knockout mouse: what it tells us about the inflammatory response. *J Physiol Pharmacol.* 2002 December; 53(4 Pt 1):541-53.
39. Fadok, V. A. and Henson, P. M., Apoptosis: giving phosphatidylserine recognition an assist—with a twist. *Curr Biol.* 13(16):R655-7 (2003).
40. Arur, S., et al., Annexin I is an endogenous ligand that mediates apoptotic cell engulfment. *Dev Cell.* 4(4):587-98 (2003).
41. Kamal A. M., et al. An annexin 1 (ANXA-1)-derived peptide inhibits prototype antigen-deriven human T cell Th1 and Th2 responses in vitro. *Clin. Exp. Allergy* 31, 1116-1125 (2001).
42. Perretti M., et al. Involvement of the receptor for formylated peptides in the in vivo anti-migratory actions of annexin 1 and its mimetics. *Am. J. Pathol.* 158, 1969-1973 (2001).
43. La M, et al. Annexin 1 peptides protect against experimental myocardial ischemia-reperfusion: analysis of their mechanism of action. *FASEB J* 15, 2247-2256 (2001).
44. Simantov R and Silverstein R L, CD36: a critical anti-angiogenic receptor. *Front Biosci* 8:s874-82 (2003).
45. St. Croix, B., et al., Genes expressed in human tumor endothelium. *Science,* 289(5482):1197-202 (2000).
46. Carson-Walter, E. B., et al., Cell surface tumor endothelial markers are conserved in mice and humans. *Cancer Res.* 61(18):6649-55 (2001).
47. Schroit, A. J. Methods and compositions for inducing autoimmunity in the treatment of cancers. Board of Regents, The University of Texas System. (U.S. Pat. No. 6,300,308). 11-9-2001. TX, US.
48. Schroit, A. J. & Madsen, J. W. Synthesis and properties of radioiodinated phospholipid analogues that spontaneously undergo vesicle-vesicle and vesicle-cell transfer. *Biochemistry* 22, 3617-3623 (1983).
49. American Cancer Society. Cancer Facts and Figures. 2003.
50. Moser, T. L. et al. Angiostatin binds ATP synthase on the surface of human endothelial cells. *Proc. Natl. Acad. Sci. U.S.A* 96, 2811-2816 (1999).

51. Troyanovsky, B., Levchenko, T., Mansson, G., Matvijenko, O. & Holmgren, L. Angiomotin: an angiostatin binding protein that regulates endothelial cell migration and tube formation. *J. Cell Biol.* 152, 1247-1254 (2001).
52. O'Reilly, M. S. et al. Angiostatin: a novel angiogenesis inhibitor that mediates the suppression of metastases by a Lewis lung carcinoma. *Cell* 79, 315-328 (1994).
53. Colorado, P. C. et al. Anti-angiogenic cues from vascular basement membrane collagen. *Cancer Res.* 60, 2520-2526 (2000).
54. Kamphaus, G. D. et al. Canstatin, a novel matrix-derived inhibitor of angiogenesis and tumor growth. *J. Biol. Chem.* 275, 1209-1215 (2000).
55. Dixelius, J. et al. Endostatin-induced tyrosine kinase signaling through the Shb adaptor protein regulates endothelial cell apoptosis. *Blood* 95, 3403-3411 (2000).
56. O'Reilly, M. S. et al. Endostatin: an endogenous inhibitor of angiogenesis and tumor growth. *Cell* 88, 277-285 (1997).
57. Maeshima, Y. et al. Identification of the anti-angiogenic site within vascular basement membrane-derived tumstatin. *J. Biol. Chem.* 276, 15240-15248 (2001).
58. Maeshima, Y. et al. Tumstatin, an endothelial cell-specific inhibitor of protein synthesis. *Science* 295, 140-143 (2002).
59. Adding a humanized antibody to vascular endothelial growth factor (Bevacizumab, Avastin) to chemotherapy improves survival in metastatic colorectal cancer [In Process Citation]. *Clin Colorectal Cancer* 3, 85-88 (2003).
60. Folkman, J., Hahnfeldt, P. & Hlatky, L. Cancer: looking outside the genome. *Nat. Rev. Mol. Cell Biol.* 1, 76-79 (2000).
61. Bamias A, Dimopoulos M A. Angiogenesis in human cancer: implications in cancer therapy. *Eur J Intern Med.* 14(8):459-469 (2003).
62. Bartlett J B, Dredge K, Dalgleish A G. The evolution of thalidomide and its IMiD derivatives as anticancer agents. *Nat Rev Cancer.* 4(4):314-22 (2004).
63. Dormond, O., Foletti, A., Paroz, C. & Ruegg, C. NSAIDs inhibit alpha V beta 3 integrin-mediated and Cdc42/Rac-dependent endothelial-cell spreading, migration and angiogenesis. *Nat. Med.* 7, 1041-1047 (2001).
64. Carmeliet, P. Angiogenesis in health and disease. *Nat. Med.* 9, 653-660 (2003).
65. Cathomas, G. Kaposi's sarcoma-associated herpesvirus (KSHV)/human herpesvirus 8 (HHV-8) as a tumor virus. *Herpes,* 10(3): 72-7 (2003).
66. Moses, A V, et al., A functional genomics approach to Kaposi's sarcoma. *Ann NY Acad Sci,* 975:180-91 (2002).
67. Lee, B S, et al., Structural analysis of the Kaposi's sarcoma-associated herpesvirus KI protein, *J. Virol.,* 77(14): 8072-86 (2003).
68. Hanayama, R. et al. Identification of a factor that links apoptotic cells to phagocytes. *Nature* 417, 182-187 (2002).
69. Soker S, Takashima S, Miao H Q, Neufeld G, Klagsbrun M., Neuropilin-1 is expressed by endothelial and tumor cells as an isoform-specific receptor for vascular endothelial growth factor. *Cell.,* 92(6):735-45 (1998).
70. Oh P, Li Y, Yu J, Durr E, Krasinska K M, Carver L A, Testa J E, Schnitzer J E., Subtractive proteomic mapping of the endothelial surface in lung and solid tumours for tissue-specific therapy, *Nature,* 429:629-35 (2004).
71. Veronese, F. M. & Harris, J. M. Introduction and overview of peptide and protein pegylation. Adv. Drug Deliv. Rev. 54, 453-456 (2002).
72. Davis, F. F. The origin of pegnology. Adv. Drug Deliv. Rev. 54, 457-458 (2002).
73. Hinds, K. D. & Kim, S. W. Effects of PEG conjugation on insulin properties. Adv. Drug Deliv. Rev. 54, 505-530 (2002).
74. Roberts, M. J., Bentley, M. D. & Harris, J. M. Chemistry for peptide and protein PEGylation. Adv. Drug Deliv. Rev. 54, 459-476 (2002).
75. Wang, Y. S. et al. Structural and biological characterization of pegylated recombinant interferon alpha-2b and its therapeutic implications. Adv. Drug Deliv. Rev. 54, 547-570 (2002).
76. Toumaire R, Simon M P, le Noble F, Eichmann A, England P, Pouyssegur J., A short synthetic peptide inhibits signal transduction, migration and angiogenesis mediated by Tie2 receptor. *EMBO Rep.,* 5(3):262-7. (2004).
77. Wu X, Zhao R, Li Z, Yao M, Wang H, Han J, Qu S, Chen X, Qian L, Sun Y, Xu Y, Gu J A novel small peptide as a targeting ligand for receptor tyrosine kinase Tie2, *Biochem Biophys Res Commun.* 315(4):1004-10 (2004).
78. Klagsbrun M, Takashima S, Mamluk R., The role of neuropilin in vascular and tumor biology. *Adv Exp Med Biol.,* 515:33-48 (2002).
79. Ho M, Yang E, Matcuk G, Deng D, Sampas N, Tsalenko A, Tabibiazar R, Zhang Y, Chen M, Talbi S, Ho Y D, Wang J, Tsao P S, Ben-Dor A, Yakhini Z, Bruhn L, Quertermous T. Identification of endothelial cell genes by combined database mining and microarray analysis. *Physiol Genomics* 13(3):249-62 (2003).
80. Pasqualini, R. & Ruoslahti, E. Organ targeting in vivo using phage display peptide libraries. *Nature* 380, 364-366 (1996).
81. Pasqualini, R., Arap, W. & McDonald, D. M. Probing the structural and molecular diversity of tumor vasculature. *Trends Mol. Med.* 8, 563-571 (2002).
82. Soff, G A. Angiostatin and angiostatin-related proteins. *Cancer Metastasis Rev.* 19(1-2): 97-107 (2000).
83. Cao Y, Cao R, Veitonmaki N. Kringle structures and antiangiogenesis. *Curr Med Chem Anti-Canc Agents.* 2(6): 667-81 (2002).
84. Kim J S, Yu H K, Ahn J H, Lee H J, Hong S W, Jung K H, Chang S I, Hong Y K, Joe Y A, Byun S M, Lee S K, Chung S I, Yoon Y. Human apolipoprotein(a) kringle V inhibits angiogenesis in vitro and in vivo by interfering with the activation of focal adhesion kinases. *Biochem Biophys Res Commun.* 313(3):534-40 (2004).
85. Fadok, V. A., Warner, M. L., Bratton, D. L. & Henson, P. M. CD36 is required for phagocytosis of apoptotic cells by human macrophages that use either a phosphatidylserine receptor or the vitronectin receptor (alpha v beta 3). *J. Immunol.* 161, 6250-6257 (1998).
86. Savill, J., Hogg, N., Ren, Y. & Haslett, C. Thrombospondin cooperates with CD36 and the vitronectin receptor in macrophage recognition of neutrophils undergoing apoptosis. *J. Clin Invest* 90, 1513-1522 (1992).
87. Sambrano, G. R. & Steinberg, D. Recognition of oxidatively damaged and apoptotic cells by an oxidized low density lipoprotein receptor on mouse peritoneal macrophages: role of membrane phosphatidylserine. *Proc. Natl. Acad. Sci. U.S.A* 92, 1396-1400 (1995).
88. Devitt, A. et al. Human CD14 mediates recognition and phagocytosis of apoptotic cells. *Nature* 392, 505-509 (1998).
89. Oka, K. et al. Lectin-like oxidized low-density lipoprotein receptor 1 mediates phagocytosis of aged/apoptotic cells in endothelial cells. *Proc. Natl. Acad. Sci. U.S.A* 95, 9535-9540 (1998).

90. Fadok, V. A. et al. A receptor for phosphatidylserine-specific clearance of apoptotic cells. *Nature* 405, 85-90 (2000).
91. Allen, T. M., Ligand-targeted therapeutics in anticancer therapy. *Nature Reviews Cancer,* 2, 750-763 (2002).
92. Hansen C B, Kao G Y, Moase E H, Zalipsky S, Allen T M., Attachment of antibodies to sterically stabilized liposomes: evaluation, comparison and optimization of coupling procedures. *Biochim Biophys Acta.* 1239(2): 133-44 (1995).
93. Torchilin V P, Levchenko T S, Lukyanov A N, Khaw B A, Klibanov A L, Rammohan R, Samokhin G P, Whiteman K R. p-Nitrophenylcarbonyl-PEG-PE-liposomes: fast and simple attachment of specific ligands, including monoclonal antibodies, to distal ends of PEG chains via p-nitrophenylcarbonyl groups. *Biochim Biophys Acta,* 1511(2): 397-411 (2001).
94. Ishida T, Iden D L, Allen T M. A combinatorial approach to producing sterically stabilized (Stealth) immunoliposomal drugs. *FEBS Lett.* 460(1):129-33 (1999).
95. Bacigalupo A, Palandri F., Management of acute graft versus host disease (GvHD). *Hematol J* 5(3):189-96. (2004).
96. Kagan, V E, et al., A role for oxidative stress in apoptosis: oxidation and externalization of phosphatidylserine is required for macrophage clearance of cells undergoing Fas-mediated apoptosis. *J. Immunol.* 169: 487-499 (2002).
97. Tanaka Y, Schroit A J. Insertion of fluorescent phosphatidylserine into the plasma membrane of red blood cells. Recognition by autologous macrophages. *J. Biol. Chem.* 258(18):11335-43 (1983).
98. Schroit A J, Madsen J W, Tanaka Y. In vivo recognition and clearance of red blood cells containing phosphatidylserine in their plasma membranes. *J. Biol. Chem.* 260 (8):5131-8 (1985).
99. Jakab, F., A medical nutriment has supportive value in the treatment of colorectal cancer. *British J of Cancer,* 89: 465-469 (2003).
100. Mutin, M., Dignat-George, F. & Sampol, J. Immunologic phenotype of cultured endothelial cells: quantitative analysis of cell surface molecules. *Tissue Antigens* 50, 449-458 (1997).
101. Granger, B. L. et al. Characterization and cloning of lgp1 10, a lysosomal membrane glycoprotein from mouse and rat cells. *J. Biol. Chem.* 265, 12036-12043 (1990).
102. Bagley, R. G. et al. Endothelial precursor cells as a model of tumor endothelium: characterization and comparison with mature endothelial cells. *Cancer Res.* 63, 5866-5873 (2003).
103. van Heerde, W. L., Poort, S., van,'., V, Reutelingsperger, C. P. & de Groot, P. G. Binding of recombinant annexin V to endothelial cells: effect of annexin V binding on endothelial-cell-mediated thrombin formation. *Biochem. J.* 302 (Pt 1), 305-312 (1994).
104. Ingber D, Fujita T, Kishimoto S, Sudo K, Kanamaru T, Brem H, Folkman J. Synthetic analogues of fumagillin that inhibit angiogenesis and suppress tumour growth. *Nature* 348(6301):555-7 (1990).
105. Adams B K, Ferstl E M, Davis M C, Herold M, Kurtkaya S, Camalier R F, Hollingshead M G, Kaur G, Sausville E A, Rickles F R, Snyder J P, Liotta D C, Shoji M. Synthesis and biological evaluation of novel curcumin analogs as anti-cancer and anti-angiogenesis agents. *Bioorg Med Chem.* 12(14):3871-83 (2004).
106. Panigrahy D, Singer S, Shen L Q, Butterfield C E, Freedman D A, Chen E J, Moses M A, Kilroy S, Duensing S, Fletcher C, Fletcher J A, Hlatky L, Hahnfeldt P, Folkman J, Kaipainen A. PPARgamma ligands inhibit primary tumor growth and metastasis by inhibiting angiogenesis. *J Clin Invest.* 110(7):923-32 (2000).
107. O'Reilly M S, Holmgren L, Shing Y, Chen C, Rosenthal R A, Moses M, Lane W S, Cao Y, Sage E H, Folkman J. Angiostatin: a novel angiogenesis inhibitor that mediates the suppression of metastases by a Lewis lung carcinoma. *Cell* 79(2):315-28.
108. O'Reilly M S, Holmgren L, Chen C, Folkman J. Angiostatin induces and sustains dormancy of human primary tumors in mice. 2(6):689-92 (1996).
109. Denis F, Colas S, Chami L, Louisot P, Le Floch 0, Tranquart F, Bougnoux P. Changes in tumor vascularization after irradiation, anthracyclin, or antiangiogenic treatment in nitrosomethyl ureas-induced rat mammary tumors. *Clin Cancer Res.* 9(12):4546-52 (2003).
110. Liekens S, Verbeken E, Vandeputte M, De Clercq E, Neyts J. A novel animal model for hemangiomas: inhibition of hemangioma development by the angiogenesis inhibitor TNP-470. *Cancer Res.* 59(10):2376-83 (1999).
111. Ambati J, Anand A, Fernandez S, Sakurai E, Lynn B C, Kuziel W A, Rollins B J, Ambati B K. An animal model of age-related macular degeneration in senescent Ccl-2- or Ccr-2-deficient mice. *Nat Med.* 9(11): 1390-7 (2003).
112. Quinones M P, Ahuja S K, Jimenez F, Schaefer J, Garavito E, Rao A, Chenaux G, Reddick R L, Kuziel W A, Ahuja S S. Experimental arthritis in CC chemokine receptor 2-null mice closely mimics severe human rheumatoid arthritis. *J Clin Invest.* 113(6):856-66 (2004).
113. David C S, Taneja V. Role of major histocompatibility complex genes in murine collagen-induced arthritis: a model for human rheumatoid arthritis. *Am J Med Sci.* 327 (4): 180-7 (2004).
114. Igarashi T, Miyake K, Kato K, Watanabe A, Ishizaki M, Ohara K, Shimada T. *Lentivirus*-mediated expression of angiostatin efficiently inhibits neovascularization in a murine proliferative retinopathy model. *Gene Ther.* 10(3): 219-26 (2003).
115. Roberts R L, Lin P C. Structural and functional optical imaging of angiogenesis in animal models. *Methods Enzymol.* 386:105-22 (2004).
116. Reimer C L, Agata N, Tammam J G, Bamberg M, Dickerson W M, Kamphaus G D, Rook S L, Milhollen M, Fram R, Kalluri R, Kufe D, Kharbanda S. Antineoplastic effects of chemotherapeutic agents are potentiated by NM-3, an inhibitor of angiogenesis. *Cancer Res.* 62(3):789-95 (2002).
117. Kerbel, R. and Folkman, J. Clinical translation of angiogenesis inhitors. *Nature Reviews Cancer.* 2: 727-739 (2002).
118. Ciardiello, F. et al. Inhibition of growth factor production and angiogenesis in human cancer cells by ZD 1839 (Iressa), a selective epidermal growth factor receptor tyrosine kinase inhibitor. *Clin Cancer Res.* 7, 1459-1465 (2001).
119. Tille, J. C. et al. Vascular endothelial growth factor (VEGF) receptor-2 antagonists inhibit. *J. Pharmacol. Exp. Ther.* 299, 1073-1085 (2001).
120. Hoekman, K. SU6668, a multitargeted angiogenesis inhibitor. *Cancer J* 7 Suppl 3, S134-S138 (2001).
121. Izumi, Y., Xu, L., di Tomaso, E., Fukumura, D. & Jain, R. K. Tumour biology: herceptin acts as an anti-angiogenic cocktail. *Nature* 416, 279-280 (2002).
122. Kerbel, R. S., Viloria-Petit, A., Okada, F. & Rak, J. Establishing a link between oncogenes and tumor angiogenesis. *Mol. Med.* 4, 286-295 (1998).

123. Kanthou, C. & Tozer, G. M. The tumor vascular targeting agent combretastatin A-4-phosphate induces reorganization of the actin cytoskeleton and early membrane blebbing in human endothelial cells. *Blood* 99, 2060-2069 (2002).
124. Dameron, K. M., Volpert, O. V., Tainsky, M. A. & Bouck, N. Control of angiogenesis in fibroblasts by p53 regulation of thrombospondin-1. *Science* 265, 1582-1584 (1994).
125. Garcia-Barros, M. et al. Tumor response to radiotherapy regulated by endothelial cell apoptosis. *Science* 300, 1155-1159 (2003).
126. Maj, J. G. et al. Microvascular function regulates intestinal crypt response to radiation. *Cancer Res.* 63, 4338-4341 (2003).
127. Trepel, M., et al. In vivo phage display and vascular heterogeneity: implications for targeted medicine. *Curr. Op. Chem. Biol.* 6: 399-404.
128. Bray G A. Medical consequences of obesity. *Clin Endocrinol Metab.* 89(6):2583-9 (2004).
129. Moore L L, Bradlee M L, Singer M R, Splansky G L, Proctor M H, Ellison R C, Kreger B E. MI and waist circumference as predictors of lifetime colon cancer risk in Framingham Study adults. *Int J Obes Relat Metab Disord.* 28(4):559-67 (2004).
130. Franklin, C. L., et al. Design, synthesis, and evaluation of water-soluble phospholipid analogues as inhibitors of phospholipase C from *Bacillus cereus*. *J. Org. Chem.* 68: 7298-7307 (2003).
131. Taylor, M. E., et al. Contribution to ligand binding by multiple carbohydrate-recognition domains in the macrophage mannose receptor. *J. Biol. Chem.* 267: 1719-1726 (1992).
132. de Freitas Balanco, J M. et al. Apoptotic mimicry by an obligate intracellular parasite downregulates macrophage microbicidal activity. *Current Biology*, 11(23): 1870-1873 (2001)
133. Vanlandschoot et al, Viral apoptotic mimicry: an immune evasion strategy developed by the hepatitis B virus. *Trends in Immunology*, 24(3): 144-147 (2003).
134. Thorstensen, K. & Romslo, I. The transferrin receptor: its diagnostic value and its potential as therapeutic target. *Scand. J. Clin. Lab Invest Suppl* 215, 113-120 (1993).
135. Bellocq, N. C., Pun, S. H., Jensen, G. S. & Davis, M. E. Transferrin-containing, cyclodextrin polymer-based particles for tumor-targeted gene delivery. *Bioconjug Chem.* 14(6):1122-32 (2003).
136. Apostolopoulos, V. & McKenzie, I. F. C. Cellular mucins: Targets for immunotherapy. Critical Reviews in Immunology 14, 293-309 (1994).
137. Finn, O. J. Tumor-specific immune responses and opportunities for tumor vaccines. *Clin. Immunol. Immunopathol.* 71, 260-262 (1994).
138. Barratt-Boyes, S. M. Making the most of mucin: A novel target for tumor immunotherapy. *Cancer Immunol. Immunother.* 43, 142-151 (1996).
139. Hinsch E, Groeger S, Oehninger S, Hinsch K D. Localization and functional importance of a conserved zona pellucida 2 protein domain in the human and bovine ovary using monoclonal anti-ZP2 peptide antibodies. *Theriogenology.* 2003 Oct. 15; 60(7):1331-44 (2003).
140. Huang, Z., Structural chemistry and therapeutic intervention of protein-protein interactions in immune response, human deficiency virus entry, and apoptosis. *Pharm. & Ther.* 86: 201-215 (2000).
141. Shukla, R., et al., Identification of synthetic phosphatidylserine translocases from a combinatorial library prepared by directed split-and-pool synthesis. *J Comb. Chem.* (2004)
142. Koivunen E, Arap W, Valtanen H, Rainisalo A, Medina O P, Heikkila P, Kantor, C, Gahmberg C G, Salo T, Konttinen Y T, Sorsa T, Ruoslahti E, Pasqualini R., Tumor targeting with a selective gelatinase inhibitor. *Nat Biotechnol.*, 17(8):768-74 (1999).
143. An P, Lei H, Zhang J, Song S, He L, Jin G, Liu X, Wu J, Meng L, Liu M, Shou C. Suppression of tumor growth and metastasis by a VEGFR-1 antagonizing peptide identified from a phage display library. *Int J Cancer.* 111(2): 165-73 (2004).
144. Arap W, Kolonin M G, Trepel M, Lahdenranta J, Cardo-Vila M, Giordano R J, Mintz P J, Ardelt P U, Yao V J, Vidal C I, Chen L, Flamm A, Valtanen H, Weavind L M, Hicks M E, Pollock R E, Botz G H, Bucana C D, Koivunen E, Cahill D, Troncoso P, Baggerly K A, Pentz R D, Do K A, Logothetis C J, Pasqualini R. Steps toward mapping the human vasculature by phage display. 8(2): 121-7 (2002).
145. Zurita A J, Arap W, Pasqualini R. Mapping tumor vascular diversity by screening phage display libraries. *J Control Release*, 91(1-2): 183-6 (2003).
146. Aderem A, Ulevitch R J. Toll-like receptors in the induction of the innate immune response. *Nature.* 406(6797): 782-7 (2000).
147. Neal J. Green, Jason Xianga, Jing Chena, Lihren Chena, Audrey M. Daviesa, †, Dave Erbeb, Steve Tama and James F. Tobinb, Structure-activity studies of a series of dipyrazolo[3,4-b:3',4'-d]pyridin-3-ones binding to the immune regulatory protein B7.1 *Bioorganic & Medicinal Chemistry.* 11(13): 2991-3013 (2003).
148. Li L, Wartchow C A, Danthi S N, Shen Z, Dechene N, Pease J, Choi H S, Doede T, Chu P, Ning S, Lee D Y, Bednarski M D, Knox S J., "A novel antiangiogenesis therapy using an integrin antagonist or anti-Flk-1 antibody coated 90Y-labeled nanoparticles", *Int J Radiat Oncol Biol Phys.* 58(4):1215-27 (2004).
149. De Jong A, Ziboh V, Robbins D. Antiphospholipid antibodies and platelets. *Curr Rheumatol Rep.* 2(3):238-45 (2000).
150. Cohen S A, Trikha M, Mascelli M A. Potential future clinical applications for the GPIIb/IIIa antagonist, abciximab in thrombosis, vascular and oncological indications. *Pathol Oncol Res.* 6(3): 163-74 (2000).

We claim:

1. A method of selecting a compound that enhances phagocytosis of target cells, comprising steps of:
   contacting a population of target cells with a candidate compound not found in nature, the candidate compound comprising (i) a cell-binding moiety and (ii) a phagocytic marker, wherein the cell-binding moiety and phagocytic marker are linked;
   contacting the target cells with a population of phagocytic cells;
   comparing the degree of phagocytosis of the target cells by the phagocytic cells with the degree of phagocytosis of a comparable population of target cells that were not exposed to the candidate compound but were also exposed to phagocytic cells under similar conditions; and
   selecting the candidate compound as a compound that enhances phagocytosis of target cells if the degree of phagocytosis of target cells that were contacted with the candidate compound is greater than the degree of phagocytosis of target cells that were not contacted with the candidate compound, wherein the cell-binding moiety is an antibody and the phagocytic marker is linked to the Fc domain of the antibody.

2. The method of claim 1, wherein the phagocytic marker comprises a phosphatidylserine head group.

3. The method of claim 1, wherein the population of phagocytic cells comprises macrophages.

4. The method of claim 1, wherein the cell-binding moiety binds to a tumor marker.

5. The method of claim 1, wherein the cell-binding moiety binds to an endothelial cell marker.

6. The method of claim 1, wherein the target cells comprise endothelial cells.

7. The method of claim 1, wherein the target cells comprise tumor cells.

8. The method of claim 1, wherein the target cells comprise cells infected with a path 9. The method of claim 1, wherein the target cells comprise eukaryotic cells.

10. The method of claim 1, wherein the phagocytic marker comprises a moiety that is naturally displayed by apoptotic or pre-apoptotic cells and enhances recognition of apoptotic or pre-apoptotic cells by phagocytic cells.

11. The method of claim 1, wherein the phagocytic marker and the cell-binding moiety are covalently linked.

12. The method of claim 1, wherein the phagocytic marker and the cell-binding moiety are linked via a linking moiety.

13. The method of claim 1, wherein the phagocytic marker and the cell-binding moiety are covalently linked via a bifunctional crosslinking reagent.

14. The method of claim 1, wherein the phagocytic marker and the cell-binding moiety are linked to first and second linking moieties, and the first and second linking moieties are linked to each other.

15. The method of claim 14, wherein the first and second linking moieties are linked by a biotin-avidin or biotin-streptavidin interaction.

16. The method of claim 1, wherein the cell-binding moiety binds to an integrin or to a Tie receptor.

17. The method of claim 1, wherein the cell-binding moiety binds to integrin alpha(v)beta(3).

18. The method of claim 1, wherein the compound comprises a lipid-containing vesicle comprising lipids, a cell-binding moiety, and a phagocytic marker.

19. The method of claim 1, further comprising comparing the ability of a compound comprising a naturally occurring phagocytic marker to enhance phagocytosis with the ability of a compound comprising a variant or fragment of a naturally occurring phagocytic marker to enhance phagocytosis.

20. The method of claim 1, further comprising comparing the degree of phagocytosis of the target cells by the phagocytic cells with the degree of phagocytosis of a population of target cells that have been induced to undergo apoptosis and exposed to phagocytic cells under similar conditions.

21. The method of claim 1, further comprising administering the compound to an animal model of disease.

22. A method of selecting a compound that enhances phagocytosis of target cells, comprising steps of:
contacting a population of target cells with a candidate compound not found in nature, the candidate compound comprising (i) a cell-binding moiety and (ii) a phagocytic marker, wherein the cell-binding moiety and phagocytic marker are linked;
contacting the target cells with a population of phagocytic cells;
comparing the degree of phagocytosis of the target cells by the phagocytic cells with the degree of phagocytosis of a comparable population of target cells that were not exposed to the candidate compound but were also exposed to phagocytic cells under similar conditions; and
selecting the candidate compound as a compound that enhances phagocytosis of target cells if the degree of phagocytosis of target cells that were contacted with the candidate compound is greater than the degree of phagocytosis of target cells that were not contacted with the candidate compound, wherein the compound is a fusion protein comprising a cell-binding moiety and a phagocytic marker, wherein if the cell-binding moiety comprises an antibody, the antibody is a single-chain antibody.

23. The method of claim 22, wherein the compound is a fusion protein comprising a cell-binding moiety and a phagocytic marker, wherein the cell-binding moiety is a single-chain antibody.

24. The method of claim 22, wherein the phagocytic marker comprises a phosphatidylserine head group.

25. The method of claim 22, wherein the population of phagocytic cells comprises macrophages.

26. The method of claim 22, wherein the cell-binding moiety binds to a tumor marker.

27. The method of claim 22, wherein the cell-binding moiety binds to an endothelial cell marker.

28. The method of claim 22, wherein the target cells comprise endothelial cells.

29. The method of claim 22, wherein the target cells comprise tumor cells.

30. The method of claim 22, wherein the target cells comprise cells infected with a pathogen.

31. The method of claim 22, wherein the target cells comprise eukaryotic cells.

32. The method of claim 22, wherein the phagocytic marker comprises a moiety that is naturally displayed by apoptotic or pre-apoptotic cells and enhances recognition of apoptotic or pre-apoptotic cells by phagocytic cells.

33. The method of claim 22, wherein the phagocytic marker and the cell-binding moiety are covalently linked.

34. The method of claim 22, wherein the phagocytic marker and the cell-binding moiety are linked via a linking moiety.

35. The method of claim 22, wherein the phagocytic marker and the cell-binding moiety are covalently linked via a bifunctional crosslinking reagent.

36. The method of claim 22, wherein the phagocytic marker and the cell-binding moiety are linked to first and second linking moieties, and the first and second linking moieties are linked to each other.

37. The method of claim 36, wherein the first and second linking moieties are linked by a biotin-avidin or biotin-streptavidin interaction.

38. The method of claim 22, wherein the cell-binding moiety binds to an integrin or to a Tie receptor.

39. The method of claim 22, wherein the cell-binding moiety binds to integrin alpha(v)beta(3).

40. The method of claim 22, wherein the compound comprises a lipid-containing vesicle comprising lipids, a cell-binding moiety, and a phagocytic marker.

41. The method of claim 22, further comprising comparing the ability of a compound comprising a naturally occurring phagocytic marker to enhance phagocytosis with the ability of a compound comprising a variant or fragment of a naturally occurring phagocytic marker to enhance phagocytosis.

42. The method of claim 22, further comprising comparing the degree of phagocytosis of the target cells by the phagocytic cells with the degree of phagocytosis of a population of target cells that have been induced to undergo apoptosis and exposed to phagocytic cells under similar conditions.

43. The method of claim 22, further comprising administering the compound to an animal model of disease.

44. A method of selecting a compound that enhances phagocytosis of target cells, comprising steps of:
contacting a population of target cells with a candidate compound not found in nature, the candidate compound comprising (i) a cell-binding moiety and (ii) a phagocytic marker, wherein the cell-binding moiety and phagocytic marker are linked;
contacting the target cells with a population of phagocytic cells;

comparing the degree of phagocytosis of the target cells by the phagocytic cells with the degree of phagocytosis of a comparable population of target cells that were not exposed to the candidate compound but were also exposed to phagocytic cells under similar conditions; and selecting the candidate compound as a compound that enhances phagocytosis of target cells if the degree of phagocytosis of target cells that were contacted with the candidate compound is greater than the degree of phagocytosis of target cells that were not contacted with the candidate compound, wherein the cell-binding moiety comprises an antibody fragment lacking an Fc domain.

45. The method of claim 44, wherein the phagocytic marker comprises a phosphatidylserine head group.

46. The method of claim 44, wherein the population of phagocytic cells comprises macrophages.

47. The method of claim 44, wherein the target cells comprise endothelial cells.

48. The method of claim 44, wherein the target cells comprise tumor cells.

49. The method of claim 44, wherein the target cells comprise eukaryotic cells.

50. The method of claim 44, wherein the phagocytic marker comprises a moiety that is naturally displayed by apoptotic or pre-apoptotic cells and enhances recognition of apoptotic or pre-apoptotic cells by phagocytic cells.

51. The method of claim 44, wherein the phagocytic marker and the cell-binding moiety are covalently linked.

52. The method of claim 44, wherein the phagocytic marker and the cell-binding moiety are linked via a linking moiety.

53. The method of claim 44, wherein the phagocytic marker and the cell-binding moiety are covalently linked via a bifunctional crosslinking reagent.

54. The method of claim 44, wherein the phagocytic marker and the cell-binding moiety are linked to first and second linking moieties, and the first and second linking moieties are linked to each other.

55. The method of claim 44, wherein the first and second linking moieties are linked by a biotin-avidin or biotin-streptavidin interaction.

56. The method of claim 44, wherein the compound comprises a lipid-containing vesicle comprising lipids, a cell-binding moiety, and a phagocytic marker.

57. The method of claim 44, further comprising comparing the ability of a compound comprising a naturally occurring phagocytic marker to enhance phagocytosis with the ability of a compound comprising a variant or fragment of a naturally occurring phagocytic marker to enhance phagocytosis.

58. The method of claim 44, further comprising comparing the degree of phagocytosis of the target cells by the phagocytic cells with the degree of phagocytosis of a population of target cells that have been induced to undergo apoptosis and exposed to phagocytic cells under similar conditions.

59. The method of claim 44, further comprising administering the compound to an animal model of disease.

* * * * *

SEQUENCE LISTING

```
<160> NUMBER OF SEQ ID NOS: 26

<210> SEQ ID NO 1
<211> LENGTH: 56
<212> TYPE: PRT
<213> ORGANISM: Artificial Sequence
<220> FEATURE:
<223> OTHER INFORMATION: Source organism: Homo sapiens
```

```
<400> SEQUENCE: 1

Cys Gly Ala Leu Leu Cys Ala Pro Ser Leu Val Ala Leu Asp Ile
1               5                   10                  15

Cys Ser Lys Asn Pro Cys His Asn Gly Gly Leu Cys Glu Glu Ile Ser
            20                  25                  30

Gln Glu Val Arg Gly Asp Val Phe Pro Ser Tyr Thr Cys Thr Cys Leu
        35                  40                  45

Lys Gly Tyr Ala Gly Asn His Cys
    50                  55

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide: illustrates concept of
      gaps in sequence

<400> SEQUENCE: 2

Ala Lys Leu Ser Ile Gly
1               5

<210> SEQ ID NO 3
<211> LENGTH: 11
<212> TYPE: PRT
<213> ORGANISM: Artificial Sequence
<220> FEATURE:
<223> OTHER INFORMATION: Source organism: Homo sapiens

<400> SEQUENCE: 3

Ala Met Val Ser Glu Phe Leu Lys Gln Ala Trp
1               5                   10

<210> SEQ ID NO 4
<211> LENGTH: 25
<212> TYPE: PRT
<213> ORGANISM: Artificial Sequence
<220> FEATURE:
<223> OTHER INFORMATION: Source organism: Homo sapiens

<400> SEQUENCE: 4

Ala Met Val Ser Glu Phe Leu Lys Gln Ala Trp Phe Ile Glu Asn Glu
1               5                   10                  15

Glu Gln Glu Tyr Val Gln Thr Val Lys
            20                  25

<210> SEQ ID NO 5
<211> LENGTH: 22
<212> TYPE: PRT
<213> ORGANISM: Artificial Sequence
<220> FEATURE:
<223> OTHER INFORMATION: Source organism: Homo sapiens

<400> SEQUENCE: 5

Trp Thr Ile Ile Gln Arg Arg Glu Asp Gly Ser Val Asp Phe Gln Arg
1               5                   10                  15

Thr Trp Lys Glu Tyr Lys
            20

<210> SEQ ID NO 6
<211> LENGTH: 7
<212> TYPE: PRT
<213> ORGANISM: Artificial Sequence
<220> FEATURE:
```

```
<223> OTHER INFORMATION: Synthetic peptide: identified by phage display

<400> SEQUENCE: 6

Asn Leu Leu Met Ala Ala Ser
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide: identified by phage display

<400> SEQUENCE: 7

Cys Thr Thr His Trp Gly Phe Thr Leu Cys
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide: identified by phage display

<400> SEQUENCE: 8

Cys Leu Arg Ser Gly Arg Gly Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide: identified by phage display

<400> SEQUENCE: 9

Cys Leu Arg Ser Gly Lys Gly Cys
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide: identified by phage display

<400> SEQUENCE: 10

Cys Leu Arg Ser Gly His Gly Cys
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide: identified by phage display

<400> SEQUENCE: 11

Cys Leu Arg Ser Gly Thr Gly Cys
1               5

<210> SEQ ID NO 12
<211> LENGTH: 13
<212> TYPE: PRT
<213> ORGANISM: Artificial Sequence
<220> FEATURE:
<223> OTHER INFORMATION: Synthetic peptide: identified by phage display
<220> FEATURE:
```

```
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 12

Cys Xaa Xaa Xaa Cys Xaa Tyr Gly Phe Cys Xaa Xaa Cys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic peptide: identified by phage display
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 13

Cys Xaa Xaa Xaa Cys Xaa Trp Gly Phe Cys Xaa Xaa Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide: identified by phage display

<400> SEQUENCE: 14

Trp His Ser Asp Met Glu Trp Trp Tyr Leu Leu Gly
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide: identified by phage display

<400> SEQUENCE: 15

Arg Arg Ala Gly Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide: identified by phage display

<400> SEQUENCE: 16

Arg Arg Ala Gly Gly Ser
1               5
```

```
<210> SEQ ID NO 17
<211> LENGTH: 4
<212> TYPE: PRT
<213> ORGANISM: Artificial Sequence
<220> FEATURE:
<223> OTHER INFORMATION: Synthetic peptide: identified by phage display

<400> SEQUENCE: 17

Pro Gly Gly Gly
1

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide: identified by phage display

<400> SEQUENCE: 18

Glu Gly Gly Thr
1

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide: identified by phage display

<400> SEQUENCE: 19

Thr Gly Gly Glu
1

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide: identified by phage display

<400> SEQUENCE: 20

Gly Pro Ser Leu His
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide: identified by phage display

<400> SEQUENCE: 21

Gly Gly Ser Val Leu
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide: identified by phage display

<400> SEQUENCE: 22

Leu Val Ser Gly Tyr
1               5
```

```
<210> SEQ ID NO 23
<211> LENGTH: 4
<212> TYPE: PRT
<213> ORGANISM: Artificial Sequence
<220> FEATURE:
<223> OTHER INFORMATION: Synthetic peptide: identified by phage display

<400> SEQUENCE: 23

Gly Arg Arg Gly
1

<210> SEQ ID NO 24
<211> LENGTH: 4
<212> TYPE: PRT
<213> ORGANISM: Artificial Sequence
<220> FEATURE:
<223> OTHER INFORMATION: Synthetic peptide: identified by phage display

<400> SEQUENCE: 24

His Gly Gly Gly
1

<210> SEQ ID NO 25
<211> LENGTH: 4
<212> TYPE: PRT
<213> ORGANISM: Artificial Sequence
<220> FEATURE:
<223> OTHER INFORMATION: Synthetic peptide: identified by phage display

<400> SEQUENCE: 25

Pro His Gly Gly
1

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide: identified by phage display
<220> FEATURE:
<221> NAME/KEY: misc_feature
<222> LOCATION: (4)..(4)
<223> OTHER INFORMATION: Xaa can be any naturally occurring amino acid

<400> SEQUENCE: 26

Val Thr Gly Xaa Ser Gly
1               5
```